United States Patent
Sasaki et al.

(10) Patent No.: US 7,692,795 B2
(45) Date of Patent: Apr. 6, 2010

(54) OPTICAL COMPONENT, OPTICAL SENSOR, SURFACE PLASMON SENSOR AND FINGERPRINT RECOGNITION DEVICE

(75) Inventors: Syo Sasaki, Nara (JP); Tomohiko Matsushita, Hirakata (JP); Takeo Nishikawa, Kyotanabe (JP); Natsuko Horiguchi, Kyoto (JP); Hidetoshi Kotera, Toyonaka (JP); Hiroo Iwata, Osaka (JP)

(73) Assignee: OMRON Corporation, Kyoto (JP)

( * ) Notice: Subject to any disclaimer, the term of this patent is extended or adjusted under 35 U.S.C. 154(b) by 462 days.

(21) Appl. No.: 11/724,681

(22) Filed: Mar. 15, 2007

(65) Prior Publication Data

US 2007/0222998 A1 Sep. 27, 2007

(30) Foreign Application Priority Data

Mar. 15, 2006 (JP) .............................. 2006-071793

(51) Int. Cl.
    *G01N 21/55* (2006.01)
(52) U.S. Cl. ..................................... 356/445
(58) Field of Classification Search ......... 356/317–318, 356/445, 450, 448; 422/52, 82.05, 164, 172; 436/172, 524, 526, 536–537; 204/400, 403, 204/298.16
    See application file for complete search history.

(56) References Cited

U.S. PATENT DOCUMENTS

| 5,822,073 | A | 10/1998 | Yee et al. |
| 2002/0044285 | A1* | 4/2002 | Pedersen et al. ............ 356/445 |
| 2003/0113231 | A1 | 6/2003 | Karube et al. |
| 2004/0090631 | A1 | 5/2004 | Elkind et al. |
| 2005/0018194 | A1 | 1/2005 | Thirstrup et al. |
| 2005/0179901 | A1 | 8/2005 | Ostlin et al. |

FOREIGN PATENT DOCUMENTS

| DE | 103 24 973 A1 | 12/2004 |
| EP | 0 341 927 A1 | 11/1989 |
| EP | 0 797 090 A2 | 9/1997 |
| EP | 0 965 835 A2 | 12/1999 |
| JP | 10-38800 | 2/1998 |
| WO | WO-00/46589 A1 | 8/2000 |

OTHER PUBLICATIONS

European Office Action dated Apr. 15, 2008 issued in corresponding Application No. 07104262.6-1524, 5 pages.
European Search Report issued in European Application No. EP 07 10 4262 mailed on Jun. 22, 2007, 8 pages.

* cited by examiner

*Primary Examiner*—Tarifur Chowdhury
*Assistant Examiner*—Michael Lapage
(74) *Attorney, Agent, or Firm*—Osha • Liang LLP

(57) ABSTRACT

A surface plasmon sensor includes a light guide reflection plate, a surface plasmon resonance layer formed on a first surface of the light guide reflection plate, a light emitting unit having a light source disposed on an end surface of the light guide reflection plate, and a light receiving element. The surface plasmon resonance layer includes a metal layer. The light guide reflection plate includes at least one first reflection surface inclined against the first surface. The light guide reflection plate is configured to transmit light emitted by the light source. The at least one first reflection surface is configured reflect the light to the surface plasmon resonance layer. The metal layer is configured to reflect the light reflected by the at least one first reflection surface. The light receiving element is configured to receive the light reflected by the metal layer.

16 Claims, 64 Drawing Sheets

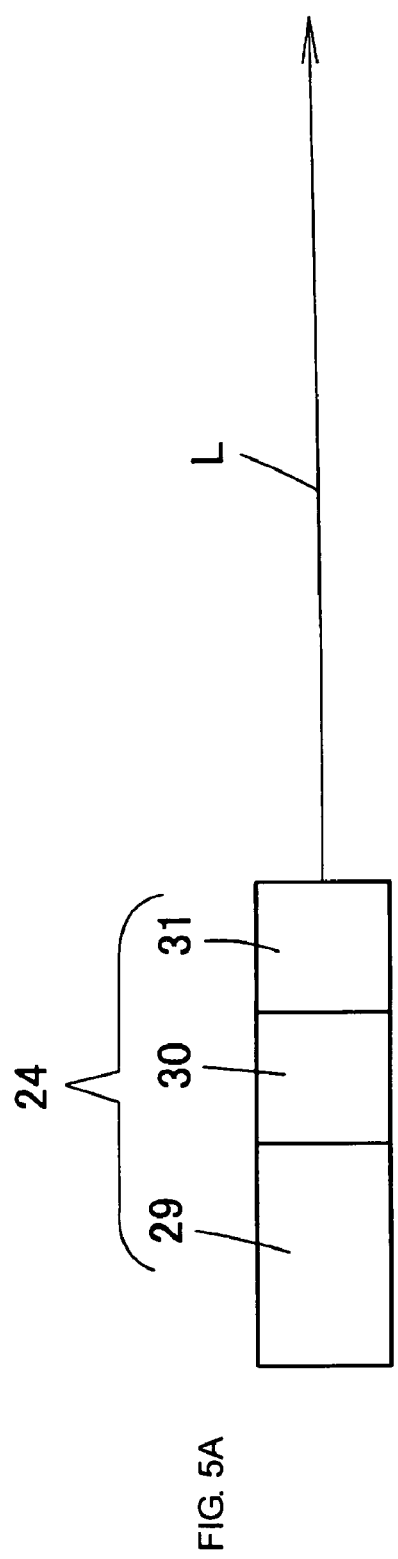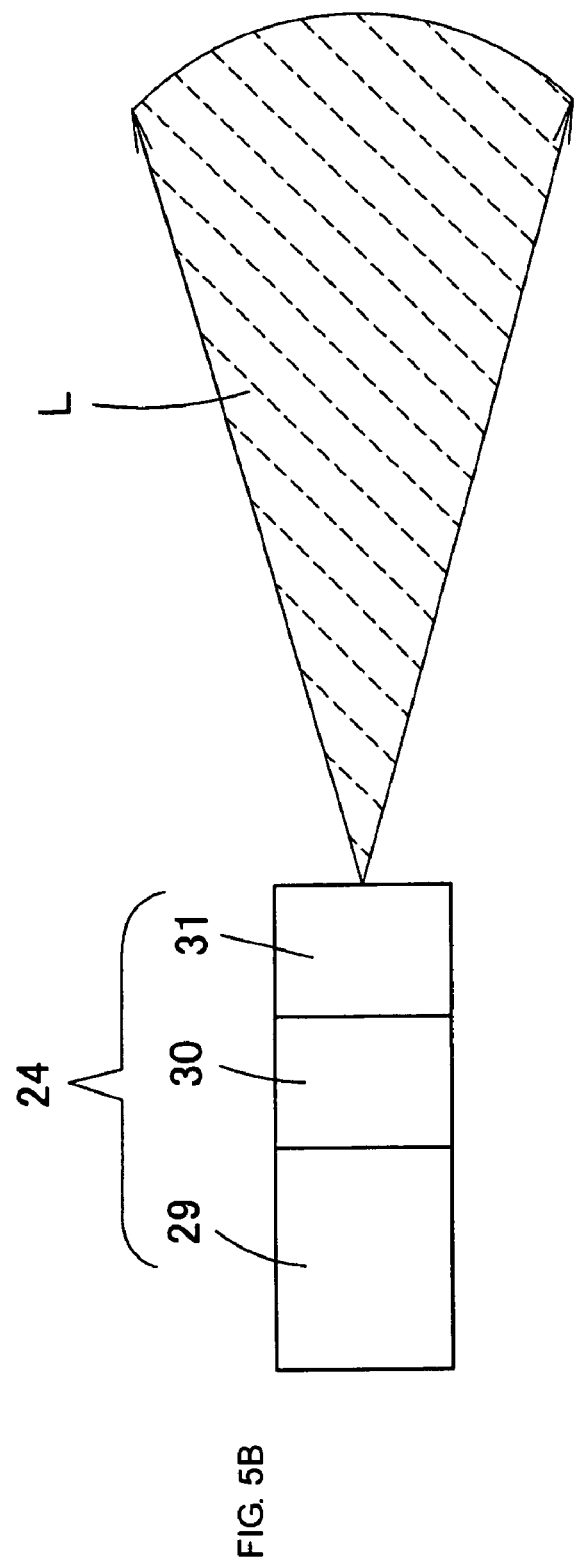
FIG. 5A
FIG. 5B

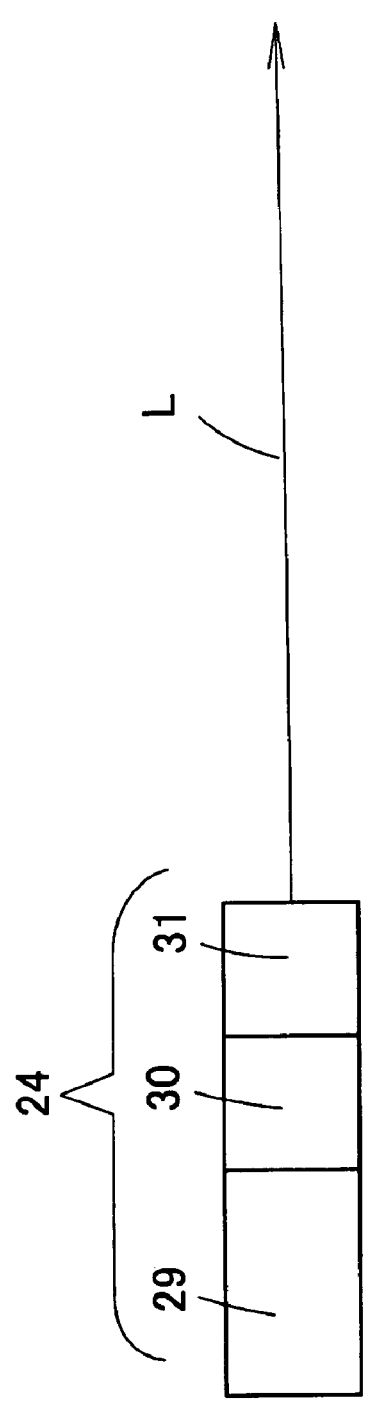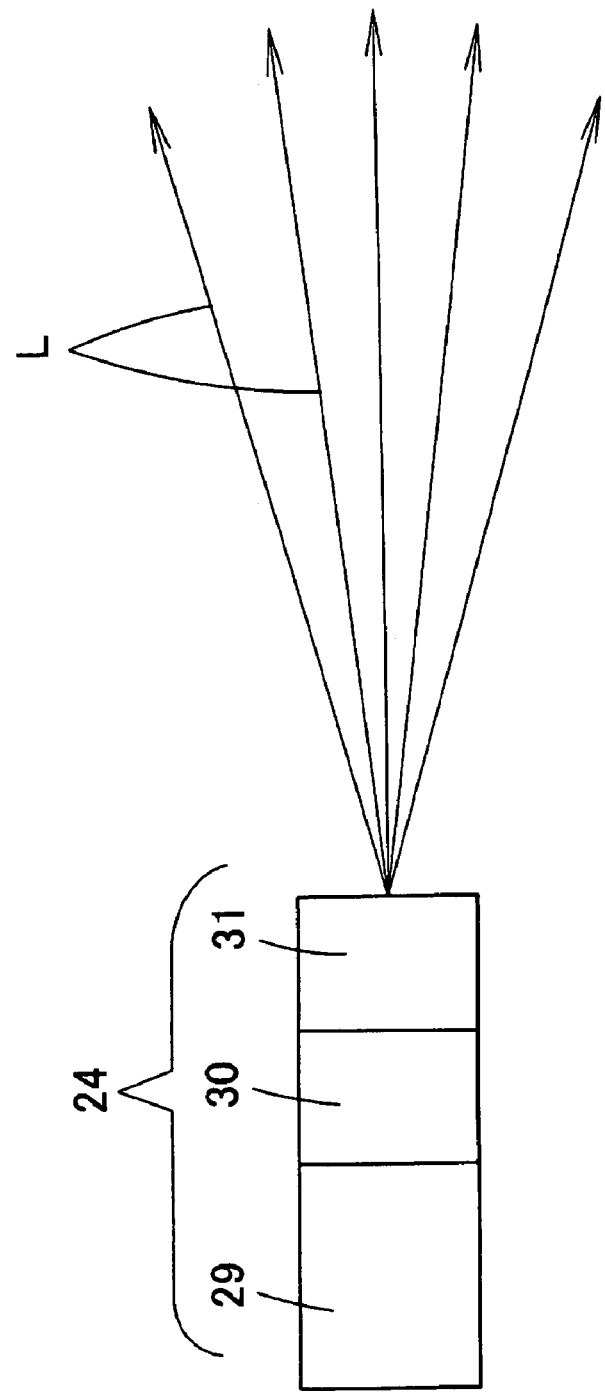

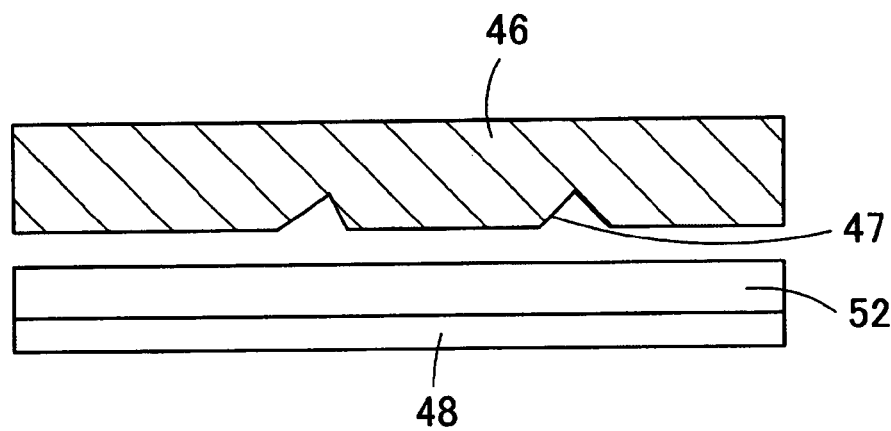
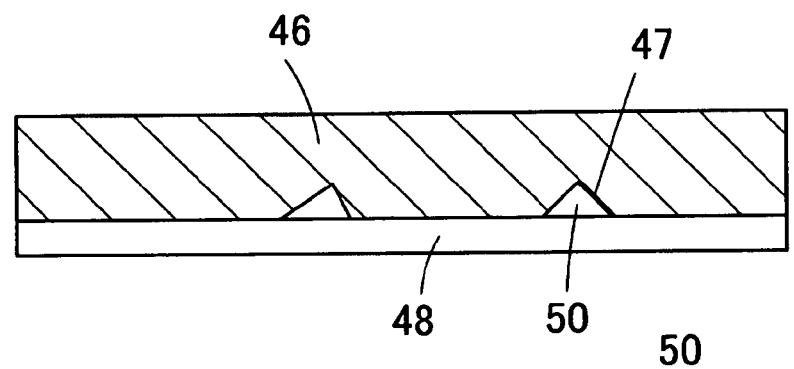
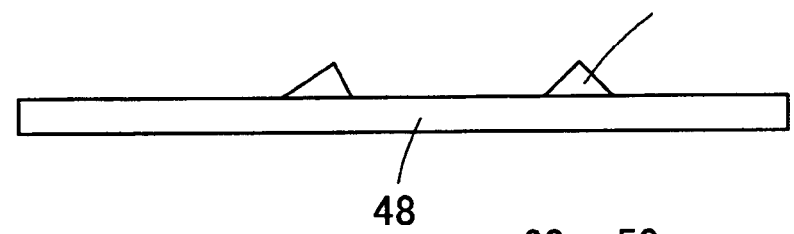
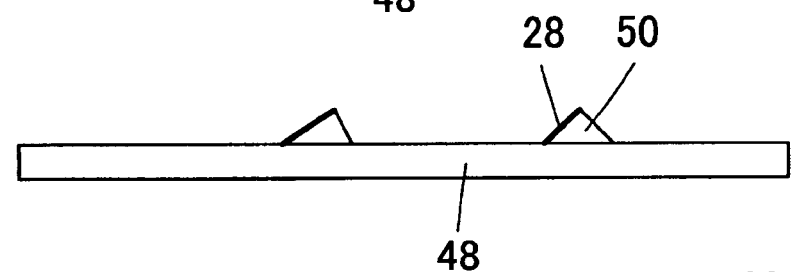
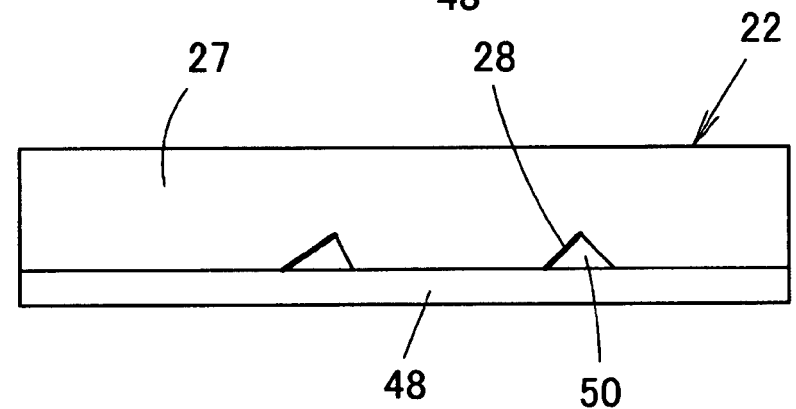
FIG. 11A
FIG. 11B
FIG. 11C
FIG. 11D
FIG. 11E

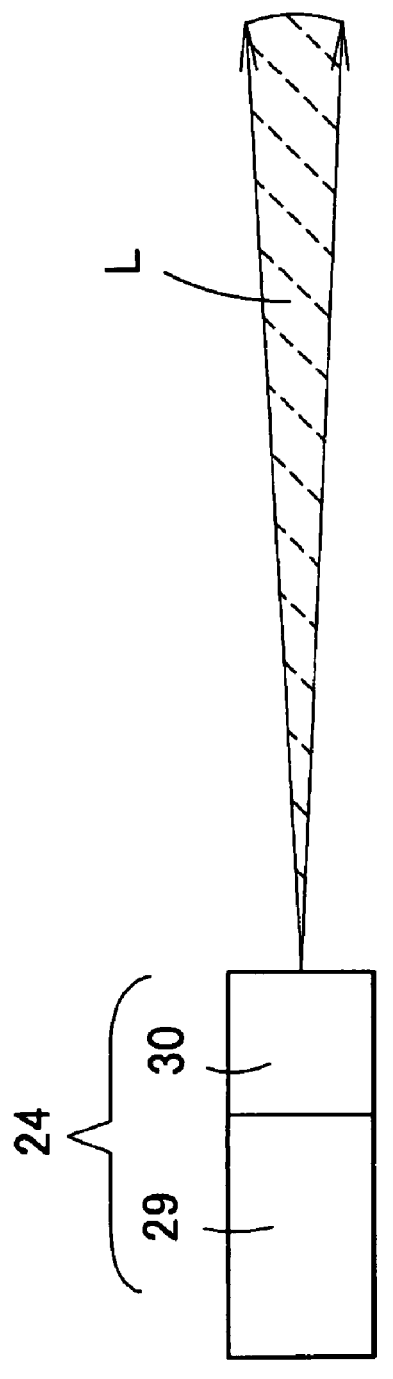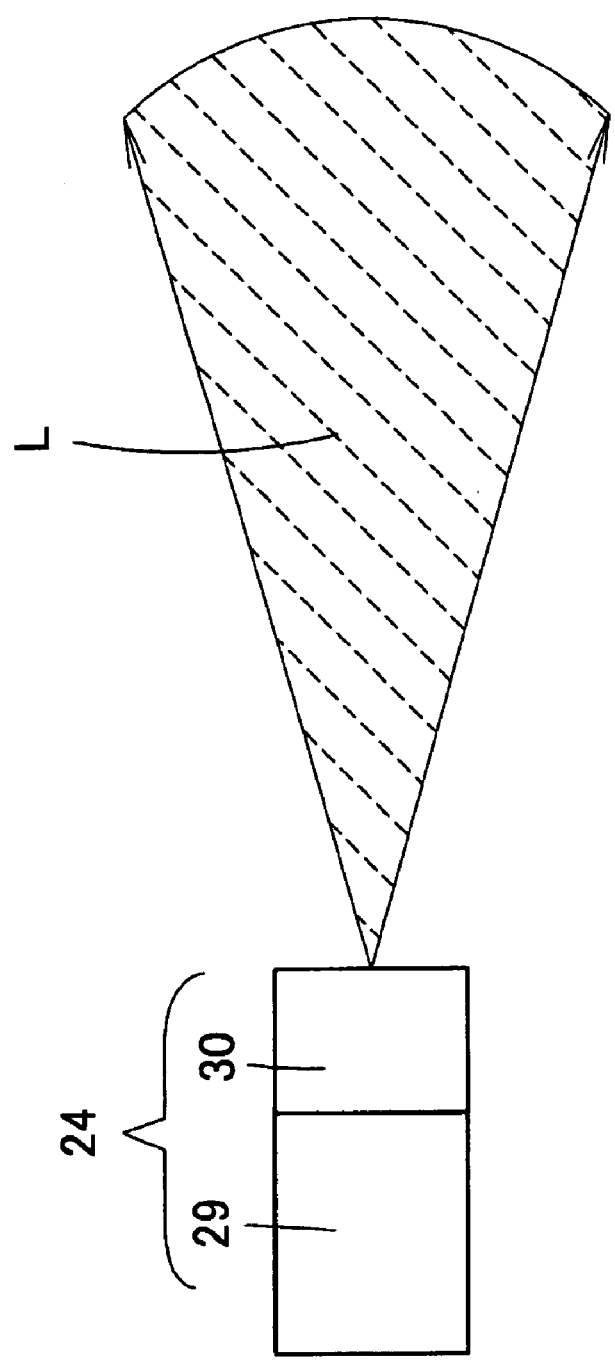
FIG. 29A
FIG. 29B

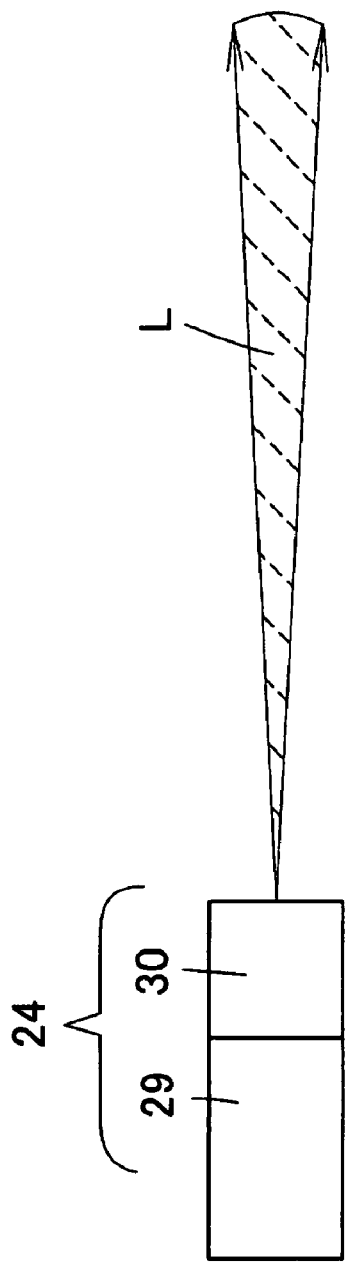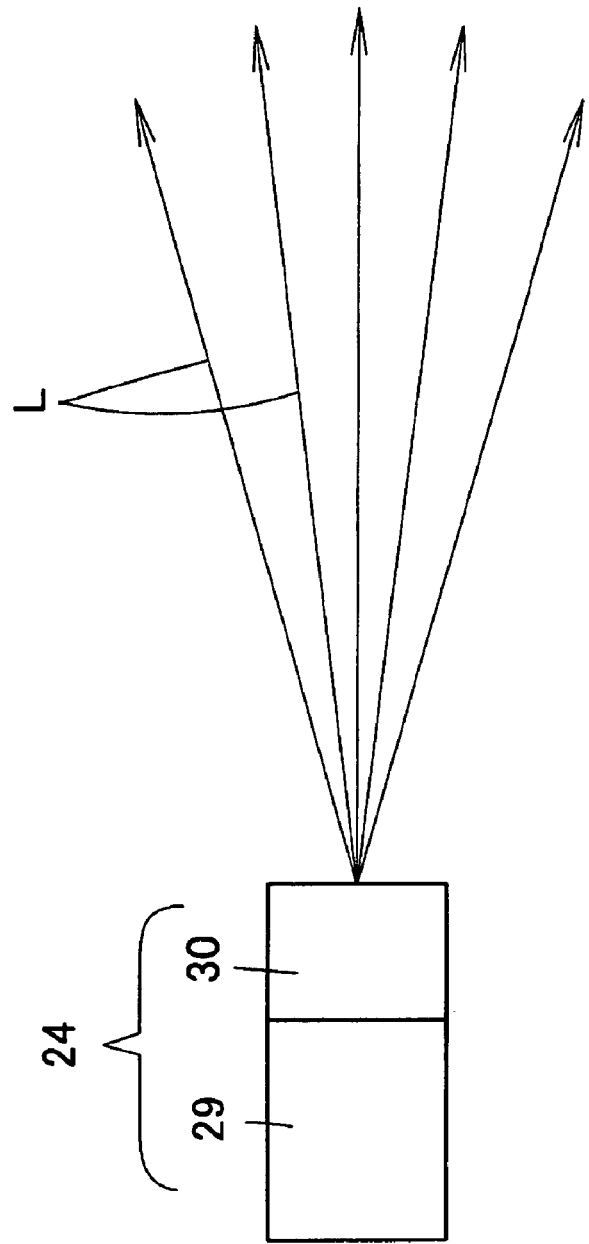

OPTICAL COMPONENT, OPTICAL SENSOR, SURFACE PLASMON SENSOR AND FINGERPRINT RECOGNITION DEVICE

BACKGROUND OF THE RELATED ART

1. Field of the Invention

The present invention relates to an optical component, an optical sensor, a surface plasmon sensor and more particularly, to a surface plasmon sensor for measurement and for fingerprint matching, and an optical component and an optical sensor, etc., used in the above surface plasmon sensor.

2. Description of the Related Art

A surface plasmon sensor using a surface plasmon resonance (SPR) is a sensor that can measure a small amount of antigen, etc with high accuracy in a nondestructive manner. As human DNA sequencing has advanced, a study for using its development has been advancing. Thus, there is a need for a biosensor that can detect protein, DNA, the reaction between an antigen and an antibody at high speed and sensitivity, and thus the surface plasmon sensor has also been used as a biosensor.

FIG. 1 shows a sectional view of the structure of a surface plasmon sensor disclosed in Japanese Patent Application Laid-Open No. 10-38800. According to this surface plasmon sensor, a transparent optical housing 12 is detachably put on a transparent substrate housing 11. The substrate housing 11 is provided with a light source unit 13 and a plurality of photoelectric detectors 14 arranged in a row. The optical housing 12 has a pentagonal or trapezoidal sectional configuration when viewed from the side thereof. A flat mirror 15 and a surface plasmon resonance layer 16 comprising an Au thin film, etc is provided on adjacent surfaces of the outer surfaces of the optical housing 12. Reference numeral 17 designates a spectrum filter.

Thus, according to the surface plasmon sensor, divergent light (polarized light) emitted from the light source unit 13 upward is reflected by the flat mirror 15 and falls onto the surface plasmon resonance layer 16; and the light reflected by the surface plasmon resonance layer 16 passes through the spectrum filter 17 and is received by the photoelectric detector 14. Here, since the divergent light falls on the surface plasmon resonance layer 16, each photoelectric detector 14 detects the intensity of the light inputted to the surface plasmon resonance layer 16 at different incident angles.

This surface plasmon sensor can be used as the biosensor as follows. On the condition that an antibody is fixed to the surface of the surface plasmon resonance layer 16, when an inspection sample solution containing an antigen that is specifically coupled to the antibody on the surface plasmon resonance layer 16 comes in contact with the antibody, the antigen is coupled to the antibody on the surface plasmon resonance layer 16. As a result, the refractive index at the interface of the surface plasmon resonance layer 16 varies and the intensity of the light received by the photoelectric detector 14 varies. Thus, when the variation of the light intensity is analyzed, it can be detected whether or not the inspection sample solution contains the antigen that is specifically coupled to the antibody on the surface plasmon resonance layer 16, or the density of the antigen can be measured.

SUMMARY

One or more embodiments of the present invention includes a small or thin high-accuracy surface plasmon sensor and fingerprint recognition device, and an optical component and an optical sensor, etc used in the surface plasmon sensor.

In one or more embodiments of the present invention, a surface plasmon sensor includes a light guide reflection plate, a surface plasmon resonance layer formed on a first surface of the light guide reflection plate, a light emitting unit having a light source disposed on an end surface of the light guide reflection plate, and a light receiving element. The surface plasmon resonance layer includes a metal layer. The light guide reflection plate includes at least one first reflection surface inclined against the first surface. The light guide reflection plate is configured to transmit light emitted by the light source. The at least one first reflection surface is configured reflect the light to the surface plasmon resonance layer. The metal layer is configured to reflect the light reflected by the at least one first reflection surface. The light receiving element is configured to receive the light reflected by the metal layer.

In one or more embodiments of the present invention, a surface plasmon sensor includes a light guide reflection plate, a surface plasmon resonance layer formed on a first surface of the light guide reflection plate, a light emitting unit having a light source disposed in a center of the light guide reflection plate, and a light receiving element. The surface plasmon resonance layer includes a metal layer. The light guide reflection plate includes at least one first reflection surface inclined against the first surface. The light guide reflection plate is configured to transmit light emitted by the light source. The at least one first reflection surface is configured reflect the light to the surface plasmon resonance layer. The metal layer is configured to reflect the light reflected by the at least one first reflection surface. The light receiving element is configured to receive the light reflected by the metal layer.

In one or more embodiments of the present invention, a flow-type analyzer includes a surface plasmon sensor, a flow path, and a sample supply path and a pump for flowing an inspection sample solution to the flow path. The surface plasmon sensor includes a light guide reflection plate, a surface plasmon resonance layer formed on a first surface of the light guide reflection plate, a light emitting unit having a light source disposed on an end surface of the light guide reflection plate, and a light receiving element disposed on a second surface of the light guide reflection plate opposite the first surface. The surface plasmon resonance layer includes a metal layer. The light guide reflection plate includes at least one first reflection surface inclined against the first surface. The light guide reflection plate is configured to transmit light emitted by the light source. The at least one first reflection surface is configured reflect the light to the surface plasmon resonance layer. The metal layer is configured to reflect the light reflected by the at least one first reflection surface. The light receiving element is configured to receive the light reflected by the metal layer. The flow path is formed on a surface of the surface plasmon layer opposite to the light guide reflection plate.

Other aspects and advantages of the invention will be apparent from the following description and the appended claims.

BRIEF DESCRIPTION OF THE DRAWINGS

FIG. 5A shows a view of light emitted from a light emitting unit in the embodiment 1 when viewed from a side direction, and FIG. 5B shows a view of the light emitted from the light emitting unit in the embodiment 1 when viewed from above;

FIG. 6A shows a view of light emitted from another light emitting unit in the embodiment 1 when viewed from a side direction, and FIG. 6B shows a view of the light emitted from another light emitting unit in the embodiment 1 when viewed from above;

FIGS. 11A to 11E show process charts showing exemplary manufacturing steps of a light guide reflection plate according to several embodiments using an embossing method;

FIG. 29A shows a view of light emitted from a light emitting unit in the embodiment 5 when viewed from a side direction, and FIG. 29B shows a view of the light emitted from the light emitting unit in the embodiment 5 when viewed from above;

FIG. 30A shows a view of light emitted from another light emitting unit in the embodiment 5 when viewed from a side direction, and FIG. 30B shows a view of the light emitted from another light emitting unit in the embodiment 5 when viewed from above;

DETAILED DESCRIPTION

Figure 1:
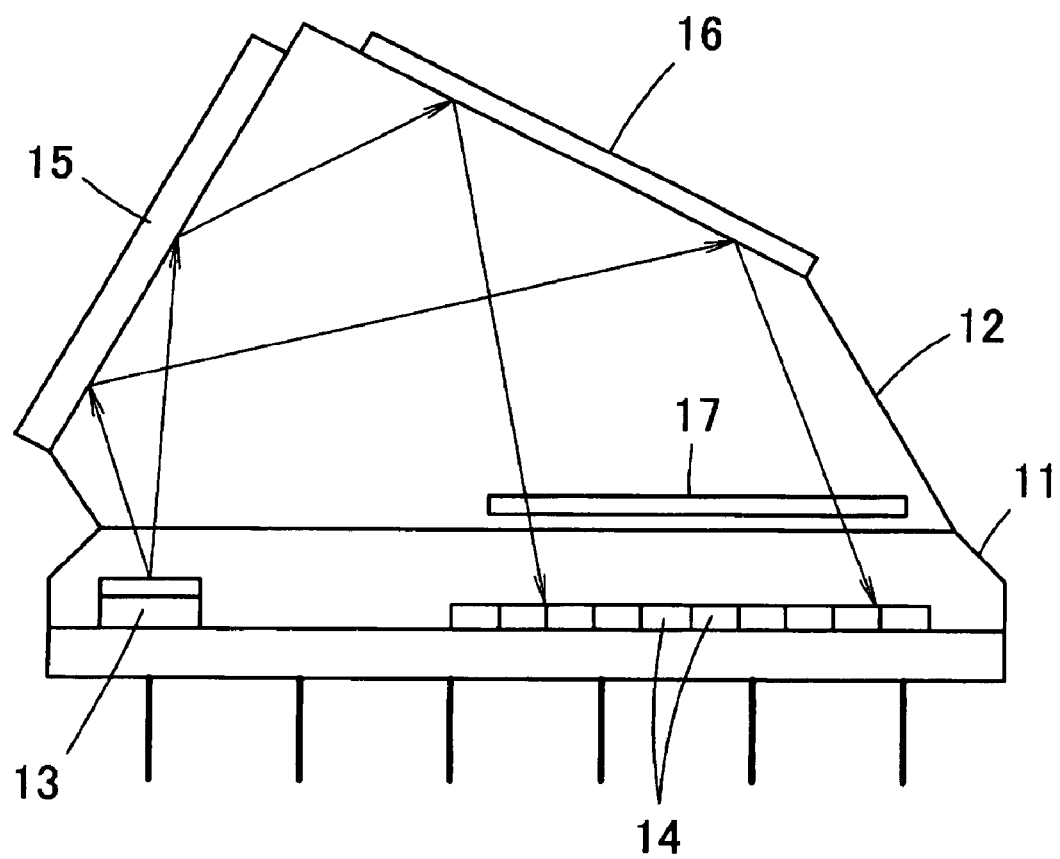
FIG. 1 shows a sectional view of the structure of a conventional surface plasmon sensor.

As shown in FIG. 1 in a conventional surface plasmon sensor, the pentagonal or trapezoidal optical housing 12 is set on the substrate housing 11, the external size becomes large and it is difficult to miniaturize it (an actual product has a size of 41.5 mm in length, 13.5 mm in width and 28.3 mm in height).

In addition, according to the above surface plasmon sensor, since the surface plasmon resonance layer 16 has a thin strip shape and only one surface plasmon resonance layer 16 exists, a plurality of inspections cannot be performed at the same time by fixing the several kinds of the antibodies. If the plurality of inspections are to be performed at the same time, the plurality of surface plasmon resonance layers 16 have to be arranged in the width direction (depth direction of the sheet surface in FIG. 1), which further increases the outer size of the surface plasmon sensor.

Embodiment 1

Figure 2:
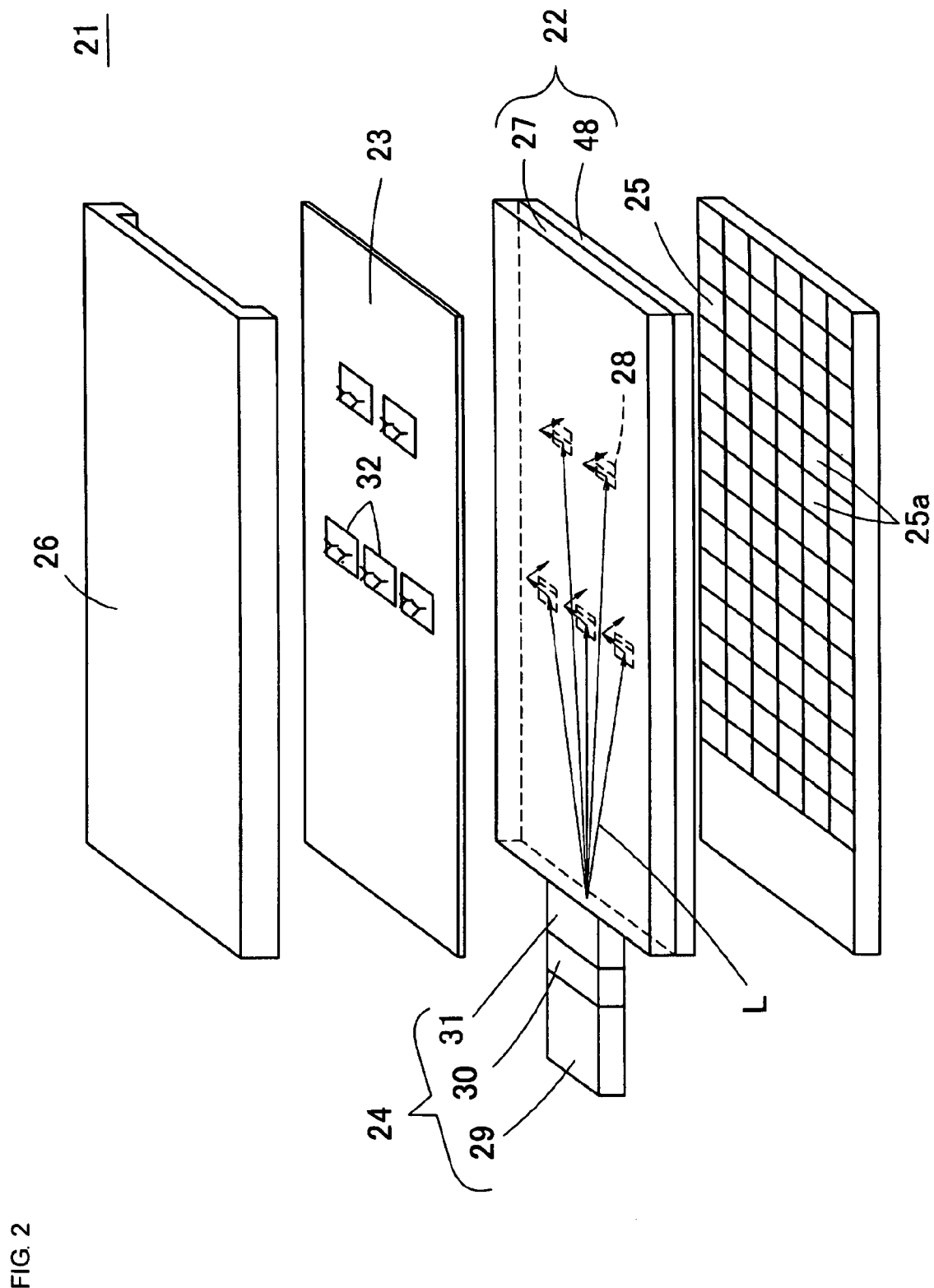
FIG. 2 shows an exploded perspective view of a surface plasmon sensor according to an embodiment 1 of the present invention.
Figure 3:
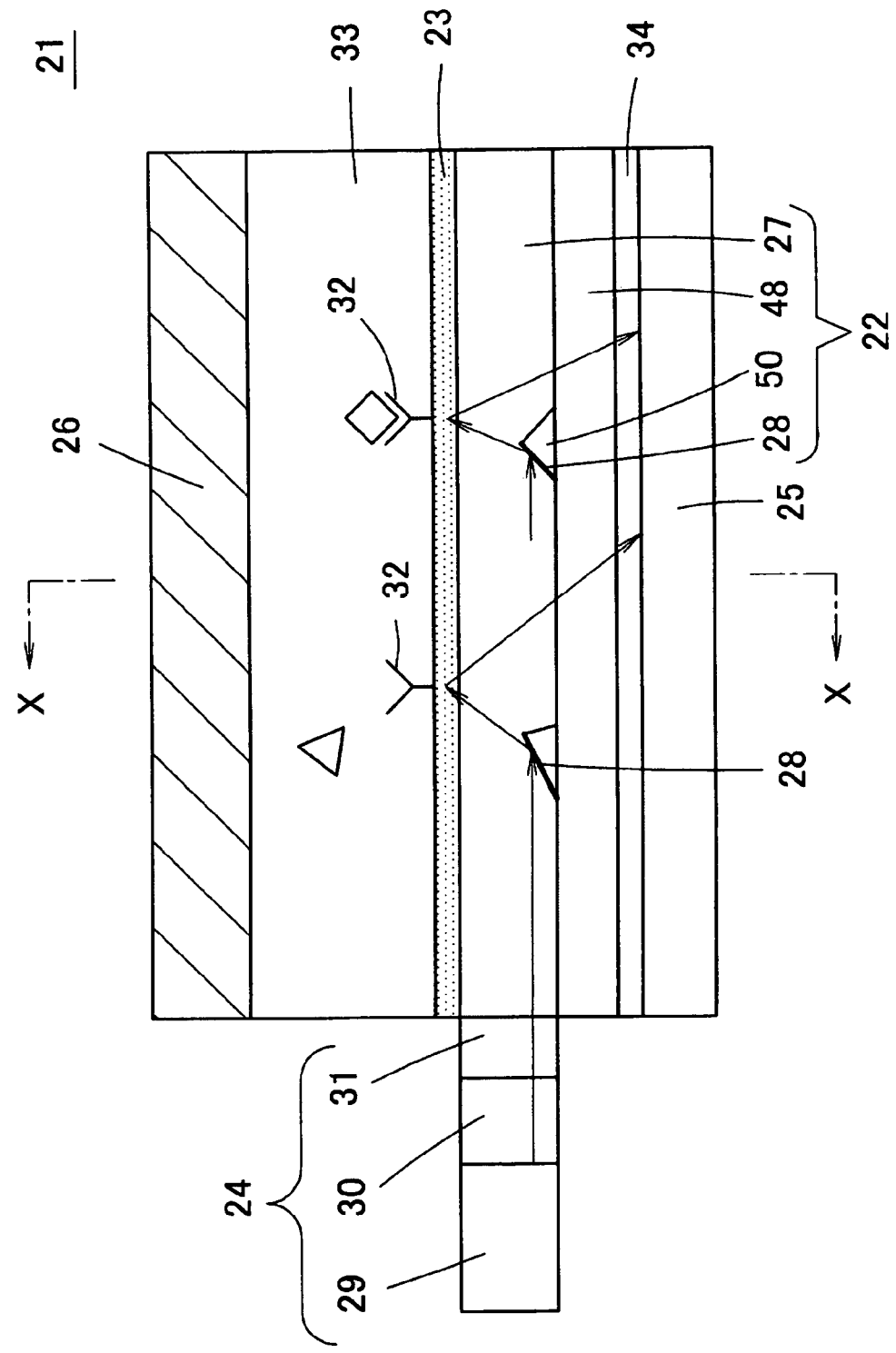
FIG. 3 shows a sectional view of the structure of the surface plasmon sensor according to the embodiment 1 of the present invention.
Figure 4:
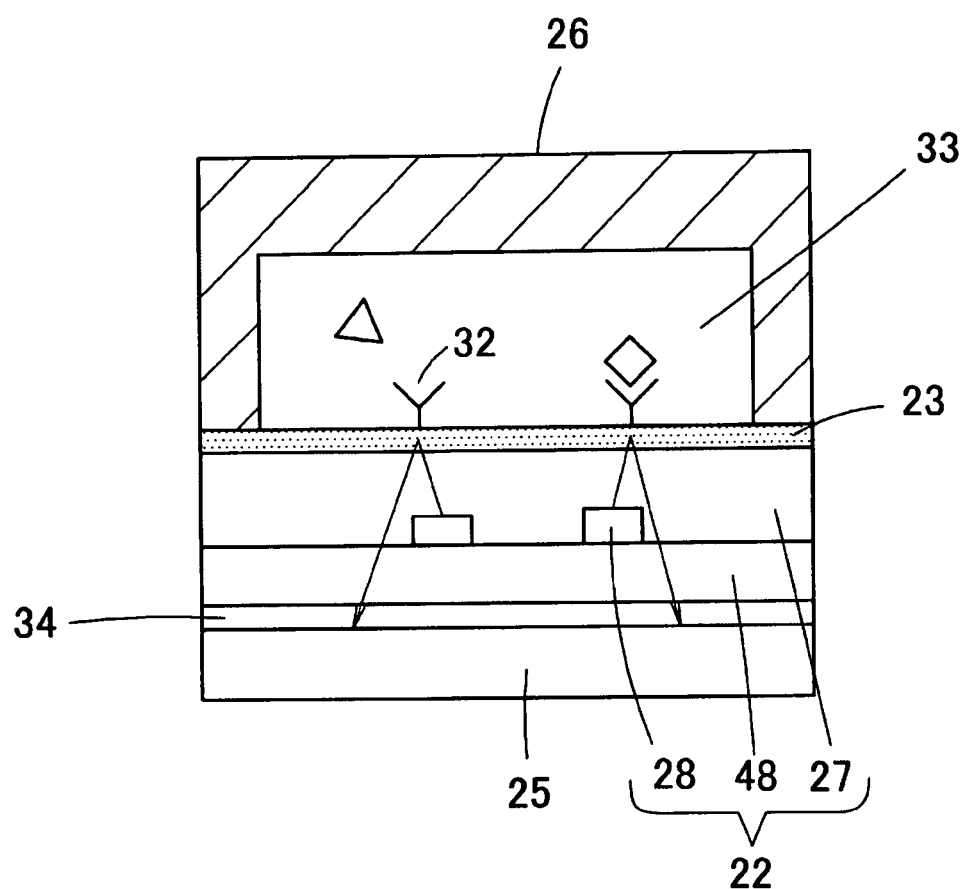
FIG. 4 shows a sectional view taken along an X-X line of FIG. 3.

FIG. 2 shows an exploded perspective view of a surface plasmon sensor 21 according to an embodiment 1 of the present invention, FIG. 3 shows a sectional view of the structure of the surface plasmon sensor 21 according to the embodiment 1, and FIG. 4 shows a sectional view taken along a X-X line of FIG. 3.

The surface plasmon sensor 21 includes a transparent light guide reflection plate 22 on which a metal layer 23 (surface plasmon resonance layer) is formed, a light emitting unit 24, a light receiving element 25, and a channel cover 26. According to this embodiment, the light guide reflection plate 22 includes a transparent substrate 48, a light guide plate 27, a projection 50, and a reflection surface 28. The transparent substrate 48 includes a transparent glass substrate or a transparent resin substrate and the light guide plate 27 positioned on the transparent substrate 48 is formed of a transparent resin such as a polycarbonate resin or a methacrylic resin having the same refractive index as that of the transparent substrate 48 into the shape of a plate. The plurality of projections 50 are sandwiched between the transparent substrate 48 and the light guide plate 27, and the reflection surface 28 having a predetermined inclined angle is provided on one inclined surface of the projection 50 by depositing a metal layer.

Figure 64A:
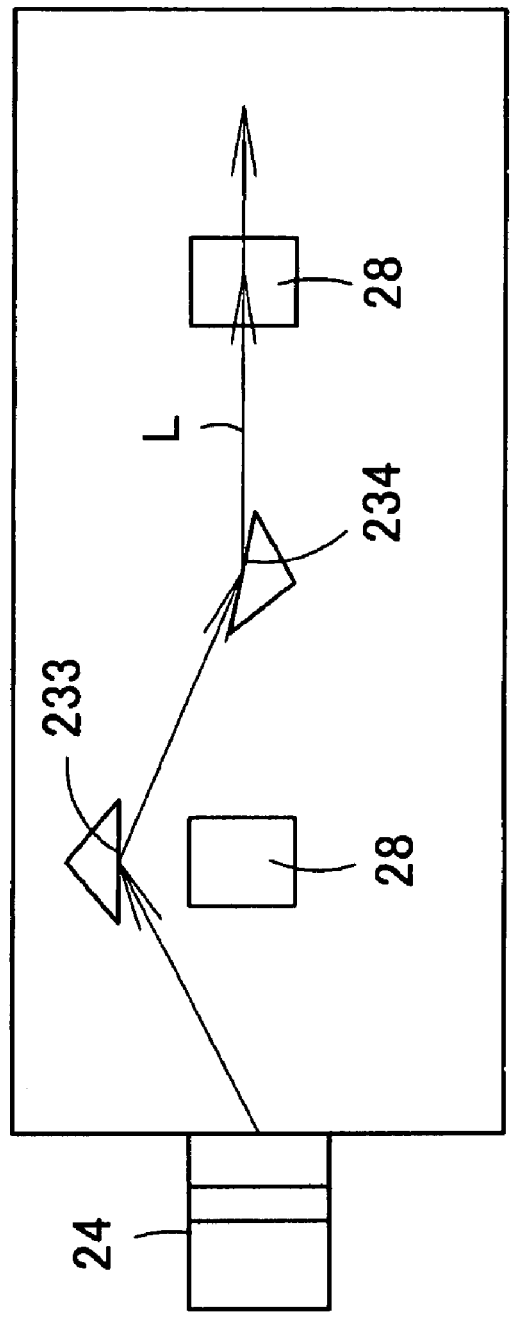
FIGS. 64A and 64B show schematic views showing a method by which light bypasses a reflection surface and reaches a rear reflection surface in the above fingerprint recognition device according to embodiment 17.

Although the plurality of reflection surfaces 28 are positioned in the same horizontal plane, the position of each reflection surface 28 is not particularly limited. However, it is desirable that light L emitted from the light emitting unit 24 toward a certain reflection surface 28 is not interrupted by the reflection surface 28 positioned closer to the light emitting unit 24 than the certain reflection surface 28. However, even when another reflection surface 28 is positioned between the light emitting unit 24 and the certain reflection surface 28, since the light emitted toward the direction out of the other reflection surface 28 (the direction in which the reflection surface 28 does not exist) can be guided to the certain reflection surface 28 by being reflected by a light guiding reflection surface (refer to FIG. 64A), it is not always that the reflection surfaces 28 must not be overlapped as viewed from the light emitting unit 24. Particularly, as the density of the reflection surfaces 28 becomes high, since the reflection surfaces 28 are likely to be overlapped, the method using the light guiding reflection surface is effective.

The light emitting unit 24 is arranged so as to be opposed to the end surface of the light guide reflection plate 22. The light emitting unit 24 includes a light source 29 such as a light emitting diode (LED) or a laser device (LD), a polarizing element 30, and a collimator 31. The polarizing element 30 polarizes the light L emitted from the light source 29 and only passes linearly polarized light in which its polarizing surface is parallel or vertical to the upper surface of the light guide reflection plate 22. This is because a variation in measurement is to be reduced by using the linearly polarized light in measurement since the reflectance characteristics are different depending on the polarizing direction. In addition, the collimator 31 is provided for collimating and narrowing a light flux in the direction perpendicular to the upper surface of the light guide reflection plate 22. While the light L emitted from the light emitting unit 24 is finely narrowed and collimated light as shown in FIG. 5A when viewed from the side direction of the light guide reflection plate 22, it spreads out in a fan-like form as shown in FIG. 5B when viewed from the direction perpendicular to the upper surface of the light guide reflection plate 22. As the collimator 31 in this case, a slit long in the horizontal direction may be used. Alternatively, it may be such that after the light L from the light source 29 has been made to be point-like light by passing through a pin hole having a size so as not to diffract, the light is narrowed and collimated by a collimating lens and spreads in the fan-like form in a horizontal plane by for example, a cylindrical lens.

Furthermore, according to another light emitting unit 24, while the emitted light L is finely narrowed and collimated light as shown in FIG. 6A when viewed from the side direction of the light guide reflection plate 22, it is emitted toward each reflection surface 28 discretely as shown in FIG. 6B when viewed from the direction perpendicular to the upper surface of the light guide reflection plate 22. In this case, the light source 29 emits pulses of light and after the light L emitted from the light source 29 has been made to be finely narrowed and collimated light, it is scanned in the horizontal direction with, for example, a small scanner.

The above-described light emitting unit 24 is set such that its light emitting position may be at the same level as that of the reflection surface 28, so that the light L emitted from the light emitting unit 24 enters the reflection surface 28 in the horizontal direction.

The metal layer 23 is formed of Au, Ag, Cu, etc on the whole upper surface of the light guide reflection plate 22 by vacuum deposition or sputtering. An antibody 32 is fixed to the upper surface of the metal layer 23 in accordance with an inspection purpose as an element for recognizing a specific molecule and coupling it specifically (referred to as the molecule recognition substance hereinafter). The antibody 32 is fixed in a region including a position in which the light L reflected from the reflection surface 28 enters the metal layer 23.

The channel cover 26 having a tunnel-shaped recessed lower surface is bonded to the upper surface of the metal layer 23. The antibody 32 is covered with the channel cover 26, and a channel 33 is formed between the channel cover 26 and the metal layer 23 to pass an inspection sample solution such as blood or body fluid.

The light receiving element 25 is a two-dimensional light receiving element such as a CCD on which a plurality of small light receiving cells 25a are arranged, and it is detachably adhered to the lower surface of the light guide reflection plate 22 with a matching oil 34 for enhancing the optical adherence thereof to prevent the reflection of the light L, sandwiched between them. In addition, the light guide reflection plate 22 and the light receiving element 25 are positioned to each other by positioning means using coupling of a projection and a hole and the like.

Figure 7:
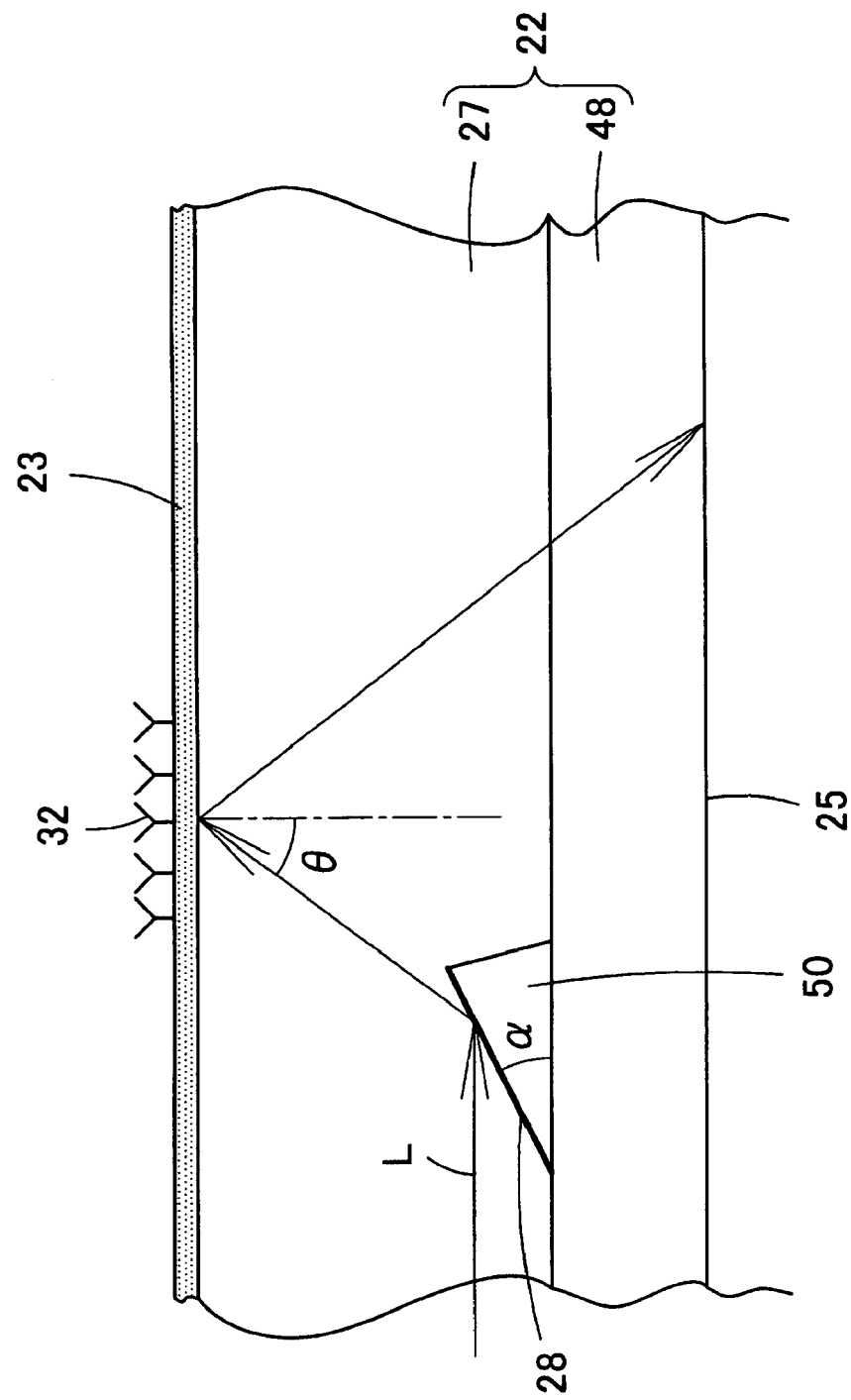
FIG. 7 shows a view of the relation between an inclined angle α of a reflection surface and an incident angle θ of light inputted to a metal layer.

In this surface plasmon sensor 21, an inspection can be executed as will be described below. As shown in FIG. 3, when the light L (polarized light) is emitted from the light emitting unit 24, the light L collimated in the vertical direction proceeds to in the horizontal direction, spreading in the light guide reflection plate 22 in the horizontal direction. After the light L has reached the reflection surface 28 and been regularly reflected by the reflection surface 28, it reaches the metal layer 23. Here, when it is assumed that an inclined angle of the reflection surface 28 is α, as shown in FIG. 7, the light L reflected from the reflection surface 28 enters the metal layer 23 at an incident angle of θ (=90−2α) with respect to a perpendicular line to the metal layer 23. The light L incident the metal layer 23 is totally reflected by the interface between the metal layer 23 and the light guide plate 27 and then received by the light receiving cell 25a at a predetermined region in the light emitting element 25 through the light guide plate 27 and the matching oil 34. Since the upper surface and the lower surface of the light guide reflection plate 22 are parallel and the light L is totally reflected by the upper surface of the light guide reflection plate 22, when the lower surface of the light guide reflection plate 22 is in contact with air, it could be totally reflected by the lower surface of the light guide reflection plate 22. Thus, the matching oil 34 having a refractive index smaller than those of the transparent substrate 48 and the light guide plate 27 is applied to the lower surface of the light guide reflection plate 22 so that the light L is easily emitted from the lower surface of the light guide reflection plate 22.

Thus, when the change in light amount in the light receiving cell 25a is detected, a physical change in a light receiving point of the metal layer 23 is measured. In addition, when the light L reaching the peripheral surface of the light guide reflection plate 22 is reflected by the peripheral surface of the light guide reflection plate 22, since this could become noise light or stray light and be detected at the light receiving element 25 a light absorbing member such as a black plate may be applied to the peripheral surface of the light guide reflection plate 22.

Figure 8:
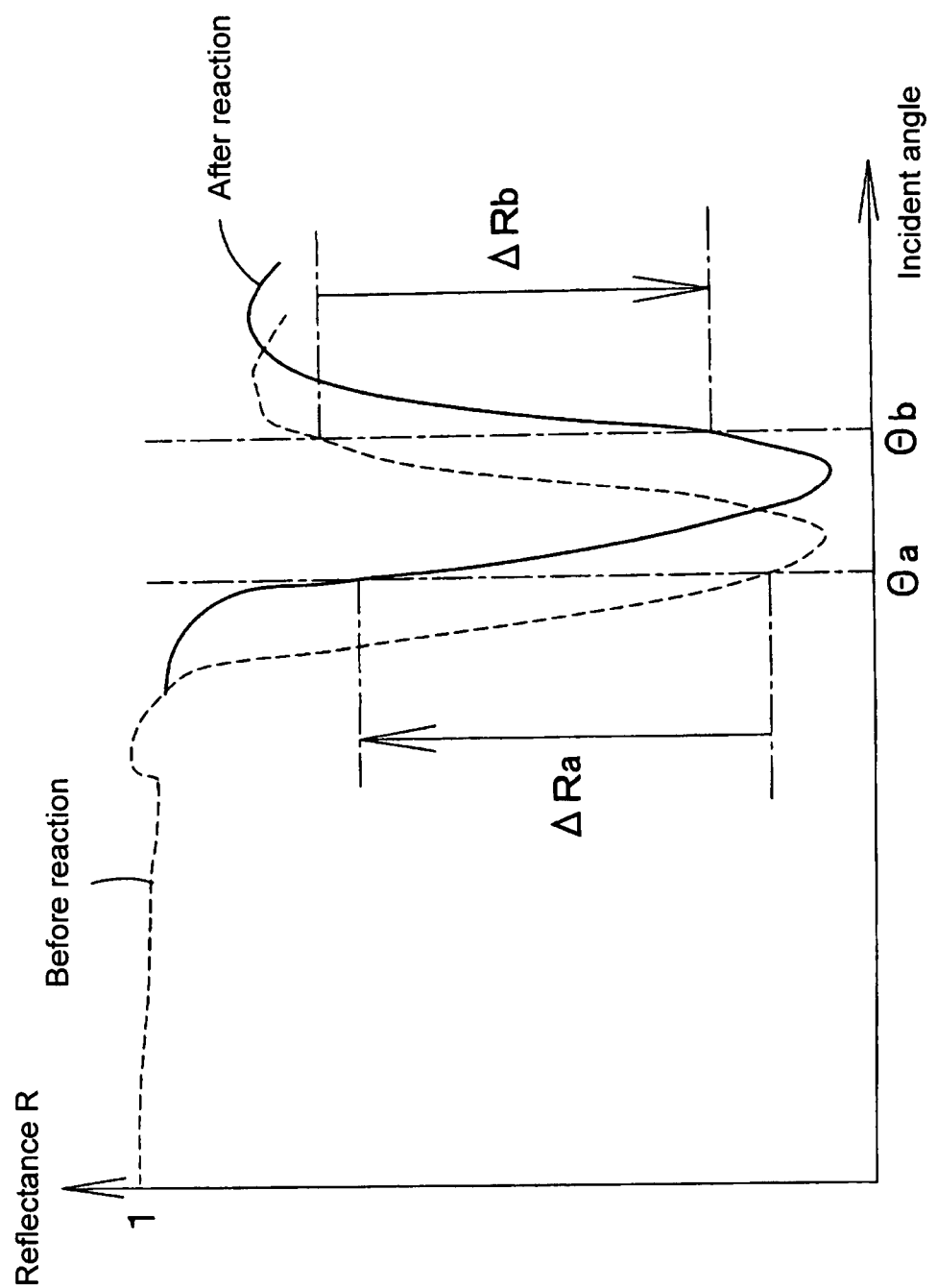
FIG. 8 shows a view to explain the measurement principle of a general surface plasmon sensor.

FIG. 8 shows a view for explaining the measurement principle of a general surface plasmon sensor (biosensor). The broken line in FIG. 8 indicates the relationship between the incident angle and the reflectance of the light L on the metal layer when the antibody and an antigen are not coupled (before reaction), and the solid line therein designates the relation between the incident angle and the reflectance when the antigen is coupled to the antibody (after reaction). The horizontal axis of FIG. 8 indicates the incident angle θ of the light L to the metal layer on which the antibody is fixed, and the vertical axis thereof indicates a reflectance R of the light L reflected by the metal layer.

When an antigen that will specifically couple to the antibody on the metal layer is contained in the inspection sample solution, the antigen is coupled to the antibody, and captured in the region in which evanescent light exists. As a result, the refractive index at the interface of the metal layer varies and the reflectance characteristics of the light L is shifted to the right as shown by the characteristic curve of the solid line in FIG. 8 after the reaction, and as the amount of the specifically coupled antigen is increased, the amount of shift to the right increases. Therefore, when the incident angle of the light L to the metal layer is fixed and the variation in the reflectance before and after the antigen is coupled is measured, it can be determined whether or not there is an antigen that was specifically coupled to the antibody and the amount of the antigen that was specifically coupled can be measured. According to such principle, it is well known that even a minute amount of antigen can be detected. Furthermore, by observing the variation in the reflectance continuously in terms of time, the temporal variation in the amount of antigen specifically coupled can be found.

Thus, according to the surface plasmon sensor 21 in the embodiment 1, when the inspection sample solution containing blood or body fluid is supplied to the channel 33 and the change in the light amount received in the predetermined light receiving cell 25a in the light receiving element 25 is detected, it can be determined whether or not the antigen that was specifically coupled to the antibody 32 exists in the inspection sample solution, the amount of antigen specifically coupled can be measured, and the temporal variation of that amount can be observed.

Furthermore, according to the surface plasmon sensor 21, the inclined angle of the reflection surface 28 and the kinds of the antibody 32 fixed to the metal layer 23 may be combined whereby various kinds of inspection methods can be implemented. For example, when a plurality of kinds of reflection surfaces 28 having different inclined angles α are provided in the light guide reflection plate 22 and the same antigen is fixed to a position in which the light L reflected by the reflection surface 28 is incident, the amount of light received at the plurality of incident angles can be measured at the same time, so that measurement precision can be improved.

In addition, by combining the reflection surfaces 28 having the different inclined angles and the same antibody 32, it can be easily detected whether there is the reaction between the antigen and the antibody. This reason will be described with reference to FIG. 8. Two kinds of reflection surfaces having different inclined angles are provided so that the light L is inputted to the metal layer 23 at the incident angles θa and θb sandwiching the minimum value of the characteristic curve before the reaction, and the reflectance of the light L inputted at the incident angle of θa is set smaller than that of the light inputted at the incident angle of θb before the reaction. Since the reflectance of the light L inputted to the metal layer 23 at the incident angle of θa is increased by ΔRa after the reaction, and the reflectance of the light L inputted to the metal layer 23 at the incident angle of θb is decreased by ΔRb after the reaction, after the reaction has been progressed to some extent, the reflectance of the light L inputted at the incident angle of θa becomes higher than the reflectance of the light L inputted to the metal layer at the incident angle of θb. While the amount of the light L at the incident angle of θa received at the light receiving cell 25a is smaller than the amount of the light L at the incident angle of θb received at the light receiving cell 25a in the light receiving element 25 before the reaction, the amount of the light L at the incident angle of θa received at the light receiving cell 25a is larger than the amount of the light L at the incident angle of θb received at the light receiving cell 25a in the light receiving element 25 after the reaction. Thus, the fact that the reaction between the antigen and the antibody is generated can be easily detected when the both light receiving amounts are inverted. In addition, by branching and leading a part of the light L inputted to the light receiving element 25 to the outside, when the reaction between the antigen and the antibody is produced, since the brightness of the two signals (reflected light) are inverted, the reaction can be easily observed visually.

Furthermore, when the plurality of reflection surfaces 28 having the same inclined angle of α are arranged along the direction in which the inspection sample solution flows in the channel 33, and the same kind of antibodies 32 are fixed to the entire metal layer 23, the behavior (temporal variation) of the antigen in which for example the antigen is specifically coupled to the antibody 32 and separated from the antibody 32 and then coupled to the antibody 32 downstream can be observed.

In addition, when the plurality of reflection surfaces 28 having the same inclined angle of α are provided in the light guide reflection plate 22, and different antibodies 32 are fixed to different positions on the metal layer 23 to which the light L reflected by the reflection surfaces 28 are incident, the plurality of kinds of antigens that are specifically coupled to the antibodies 32 can be inspected at the same time, so that the inspection operation can be more efficiently carried out.

Furthermore, when a plurality of reflection surfaces 28 having the same inclined angle of α are provided in the light guide reflection plate 22, the same kind of antibodies 32 are fixed to the entire metal layer 23, and the channel 33 is divided so that different inspection sample solutions flow in the divided areas, a plurality of kinds of the antigens that are specifically coupled to the antibodies can be inspected at the same time, so that the inspection operation can be more efficiently carried out.

In addition, any of the above-mentioned inspection methods may be combined.

According to the above surface plasmon sensor 21, since the plate-shaped light guide reflection plate 22 and light receiving element 25 are used, the surface plasmon sensor 21 can be miniaturized and thinned. Especially, even when the number of reflection surfaces 28 is increased and the inspections are performed at the plurality of positions; its external size is substantially the same. In addition, since the reflection surface 28 may have any inclined angle and it may be set at any position, the channel in which the inspection sample solution flows can be designed in a plane, so that the degree of freedom of the fixed positions of the channel and the antibody is increased and a plurality of kinds of antibodies can be fixed or the antibodies can be fixed to the plurality of positions.

Thus, the surface plasmon sensor 21 can be miniaturized and thinned keeping high inspection efficiency and high inspection accuracy.

FIGS. 9A to 9D show process charts for explaining exemplary steps for manufacturing the stamper for mass-production by Photo-Polymerization (2P) method, and FIGS. 10A to 10D show process charts for explaining exemplary steps for mass-producing a light guide reflection plate 22 using the stamper.

Figure 9A:
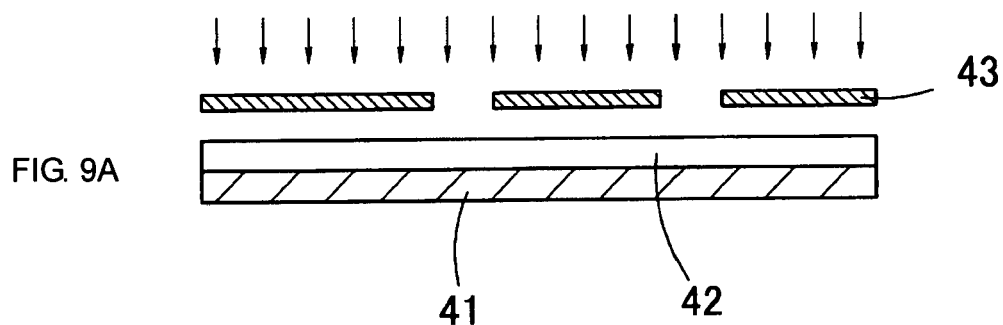
FIGS. 9A to 9D show process charts for explaining exemplary manufacturing steps of a stamper for mass production by 2P (Photo-Polymerization) method.
Figure 9B:
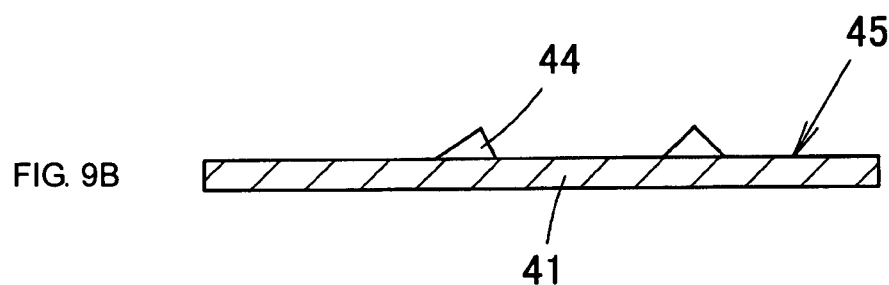

A substrate 41 is prepared and an electron beam resist 42 is applied thereon. Then, as shown in FIG. 9A, the resist 42 is microfabricated by applying the electron beam over a mask 43, and as shown in FIG. 9B, a model 44 of the projection 50 on which the reflection surface 28 is formed is manufactured with the resist 42 on the substrate 41.

Figure 9C:
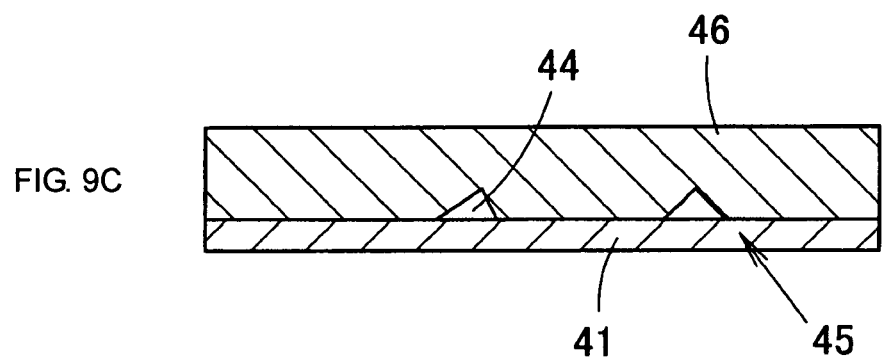
Figure 9D:
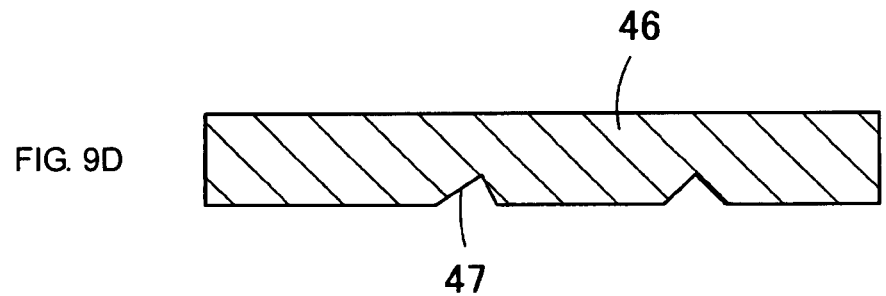

After a matrix 45 having the model 44 of the projection 50 has been manufactured, as shown in FIG. 9C, a stamper material such as nickel is deposited on the matrix 45 by an electroforming method, whereby the stamper 46 is manufactured. Then, as shown in FIG. 9D, the stamper 46 is removed from the matrix 45, and the stamper 46 is completed. According to the stamper 46, a recessed part 47 is formed corresponding to the configuration of the model 44 of the projection 50.

After the stamper 46 has been manufactured, the light guide reflection plate 22 is mass-produced using the stamper 46 by the 2P method. First, as shown in FIG. 1A, after a UV cured resin 49 has been dropped on a transparent substrate 48 which may be for example a transparent glass substrate or a transparent resin substrate, the stamper 46 is lowered onto the UV cured resin 49 so that the UV cured resin 49 is sandwiched between the transparent substrate 48 and the stamper 46 and the recessed part 47 of the stamper 46 is filled with the UV cured resin 49.

Figure 10A:
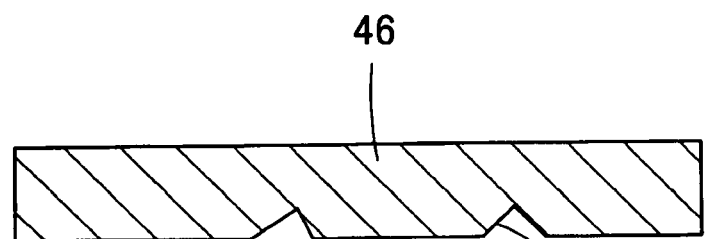
FIGS. 10A to 10D show process charts for explaining exemplary mass-producing steps of a light guide reflection plate using the stamper manufactured by the steps shown in FIG. 9.
Figure 10B:
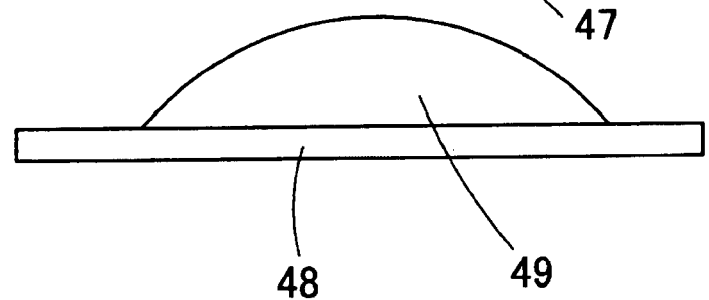

Then, the UV cured resin 49 is irradiated with UV light from the side of the transparent substrate 48. Thus, the UV cured resin 49 is cured by a light curing reaction. After the UV cured resin 49 has been cured, the stamper 46 is removed from the UV cured resin 49, whereby the triangular projection 50 including the UV cured resin 49 is formed on the transparent substrate 48 as shown in FIG. 10B.

Figure 10C:
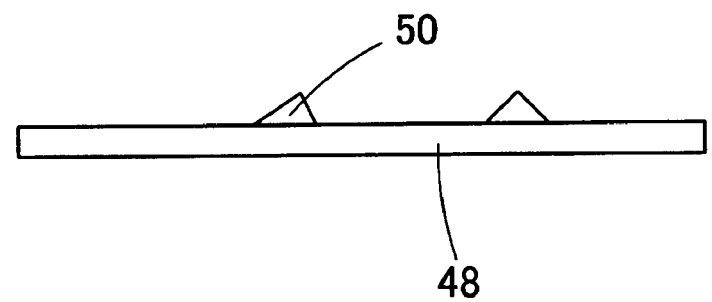
Figure 10D:
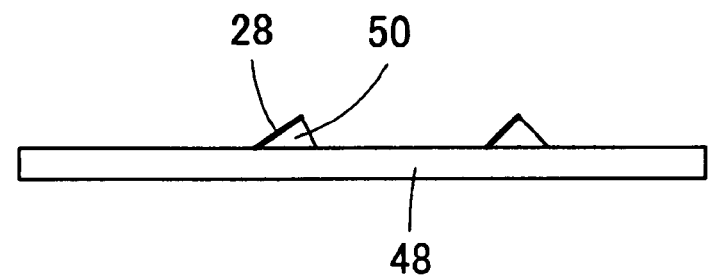

One inclined surface of the projection 50 has a predetermined inclined angle and a metal thin film formed of Ag, Al, Cu, etc is selectively deposited on the inclined surface, whereby the reflection surface 28 is formed on the inclined surface of the projection 50 as shown in FIG. 10C. The method of selectively depositing the metal thin film includes a lift-off method in which the metal thin film is deposited from above a resist having an opening at one part by sputtering and unnecessary metal thin film is removed together with the resist, a micro-molding method, a screen printing method, and an ink-jetting method. Then, the light guide plate 27 is formed of a resin having the same refractive index as that of the transparent substrate 48 on the transparent substrate 48, to complete the light guide reflection plate 22 in which the projection 50 and the reflection surface 28 are buried in the transparent substrate 48 and the light guide plate 27.

In addition, according to another method of manufacturing the light guide reflection plate 22, the light guide reflection plate 22 may be duplicated using an embossing method. FIGS. 11A to 11E show process charts of step for manufacturing a light guide reflection plate 22 using the embossing method. According to the steps, as shown in FIG. 11A, after a resin 52 such as an acrylic resin has been spin-coated on the transparent substrate 48, the stamper 46 manufactured by the steps shown in FIG. 9 is put on the transparent substrate 48, and the resin 52 is pressed by the stamper 46 as shown in FIG. 11B.

When the stamper 46 is removed, as shown in FIG. 11C, the same pattern as the model 44 of the projection 50 is transferred on the transparent substrate 48, whereby the projection 50 is formed. Then, as shown in FIG. 11D, the reflection surface 28 is formed on the inclined surface of the projection 50 and as shown in FIG. 11E, the light guide plate 27 is formed on the upper surface of the transparent substrate 48 from above the projection 50 and the reflection surface 28, whereby the light guide reflection plate 22 is manufactured.

According to the conventional example, although it is not suitable for the mass production because it is manufactured by a batch processing, according to the surface plasmon sensor 21, since it can be duplicated by a duplicating method using the stamper, they can be mass-produced, so that its manufacturing cost can be low.

Next, a description will be made of a method of reusing the above surface plasmon sensor 21. In the used surface plasmon sensor 21, after the inspection sample solution has passed through the channel 33, the antigen and a biomolecule are attached on the antibody 32 on the metal layer 23. When it is used in a laboratory, this may be cleaned to remove the antigen and the antibody attached on the metal layer from the metal layer and a desired new antibody can be fixed to the metal layer again. However, in the medical field, the above reuse method is not efficient.

Therefore, it may be desired that the surface plasmon sensor 21 is to be disposable, that is, it is to be abandoned after use. However, since the light source 29 and the light receiving element 25 used in the surface plasmon sensor 21 are expensive, when the whole surface plasmon sensor 21 is thrown away after use, the cost of the surface plasmon sensor 21 becomes high. Thus, a surface plasmon sensor 21 according to embodiment 1 may be partially disposable.

According one method, the light emitting unit 24 and the light receiving element 25 and the channel cover 26 are to be repetitively used and the light guide reflection plate 22 on which the metal layer 23 is formed is to be replaced with a replacement component 53 after each use. The replacement component 53 is provided by thinly applying the matching oil 34 on the lower surface of the light guide reflection plate 22 on which the metal layer 23 has been formed and the antibody 32 is fixed to the metal layer 23. The replacement components 53 in which various kinds of antibodies can be fixed in accordance with the purpose are to be prepared. Although a special technique has been needed to fix the antibody to the metal layer and a specialist has fixed the antibody to the metal layer at the scene it is used conventionally, since the antibody 32 has been fixed to the metal layer 23 in the replacement component 53 previously, it is not necessary to fix the antibody 32 by a user, so that the replacement component can be used without any special technique. In addition, since the light guide reflection plate 22 is adhered to the light receiving element 25 with the matching oil 34 sandwiched between them, when the matching oil 34 has been thinly applied to the lower surface of the replacement component 53, a process for applying the matching oil 34 can be omitted.

Figure 12:
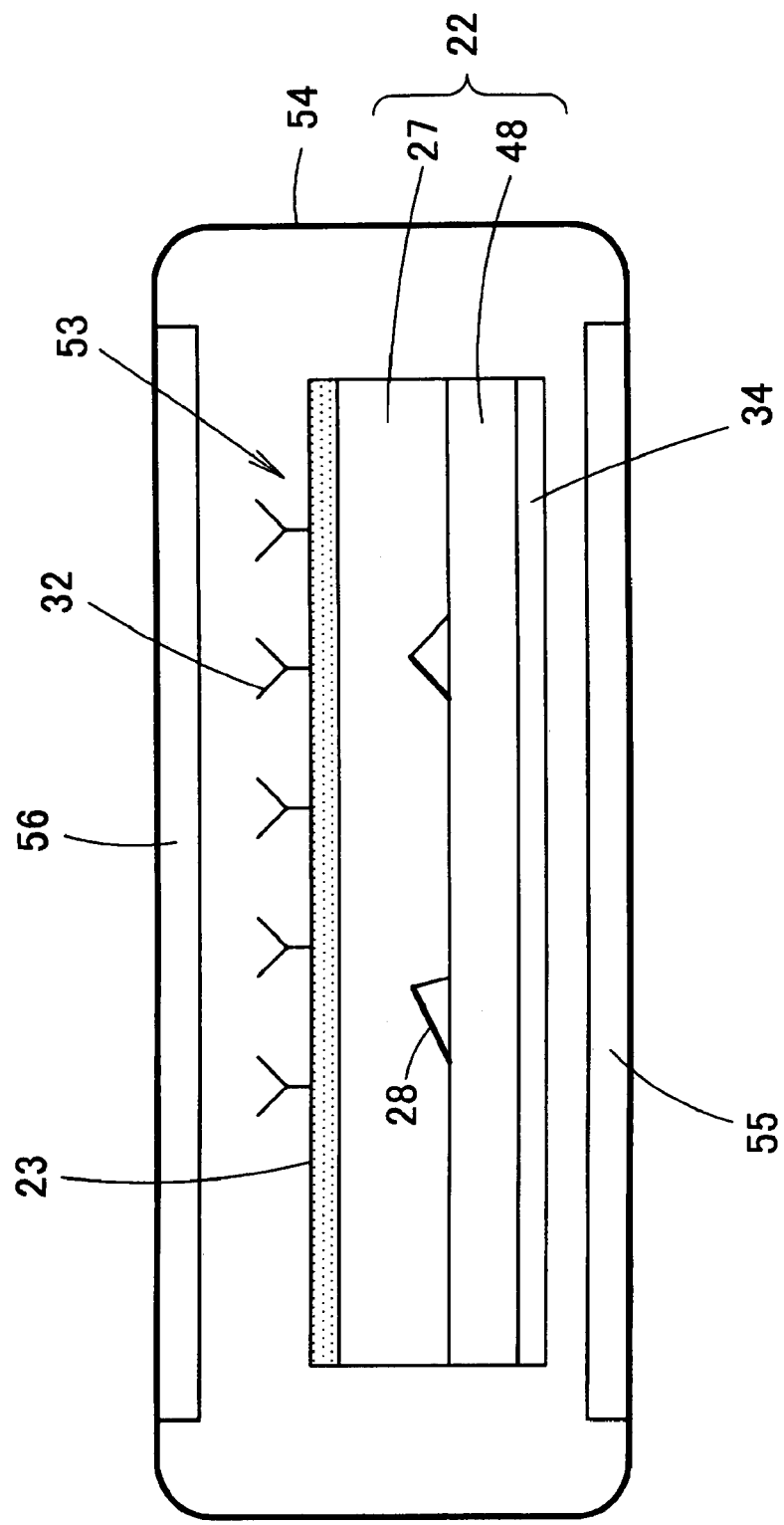
FIG. 12 shows a sectional view of a possible replacement component of the surface plasmon sensor in the embodiment 1 sealed in a moisture proof case.

The replacement component 53 is supplied to the market such that it is sealed in a moisture proof case 54 formed of a moisture proof film or plastic as shown in FIG. 12. Since the antibody 32 and the matching oil 34 could be dried and especially the antibody 32 has to be moist constantly, the replacement component 53 is sealed in the moisture proof case 54 so that the antibody 32 and the matching oil 34 are prevented from being dried. In addition, sponges 55 and 56 are attached to the bottom and top surfaces of the moisture proof case 54, and the replacement component 53 is set such that the surface on which the matching oil 34 is applied is put on the sponge 55 on the bottom. The sponge 55 contains the matching oil, so that the matching oil 34 of the replacement component 53 is prevented from being dried and the matching oil 34 of the replacement component 53 is prevented from being absorbed by the sponge 55. The sponge 56 on the top surface contains water, so that the antibody 32 fixed to the metal layer 23 is prevented from being dried and kept in the moist state.

Thus, in using the replacement component 53, it is taken out of the moisture proof case 54 and put on the light receiving element 25 and adhered onto the upper surface of the light receiving element 25 through the matching oil 34. In addition, the channel cover 26 is bonded to the metal layer 23, and the light emitting unit 24 is positioned and mounted on the end surface of the light guide reflection plate 22, to inspect the antigen, etc.

After the inspection has been completed, the channel cover 26, the light emitting unit 24 and the light receiving element 25 are removed from the replacement component 53 and the replacement component 53 is put back in the moisture proof case 54 and abandoned.

Thus, since the replacement component 53 is disposable, the surface plasmon sensor 21 can be easily used without any specialist, and since the expensive light emitting unit 24 and light receiving element 25 can be repetitively used, the cost of the surface plasmon sensor 21 can be lowered.

Figure 13:
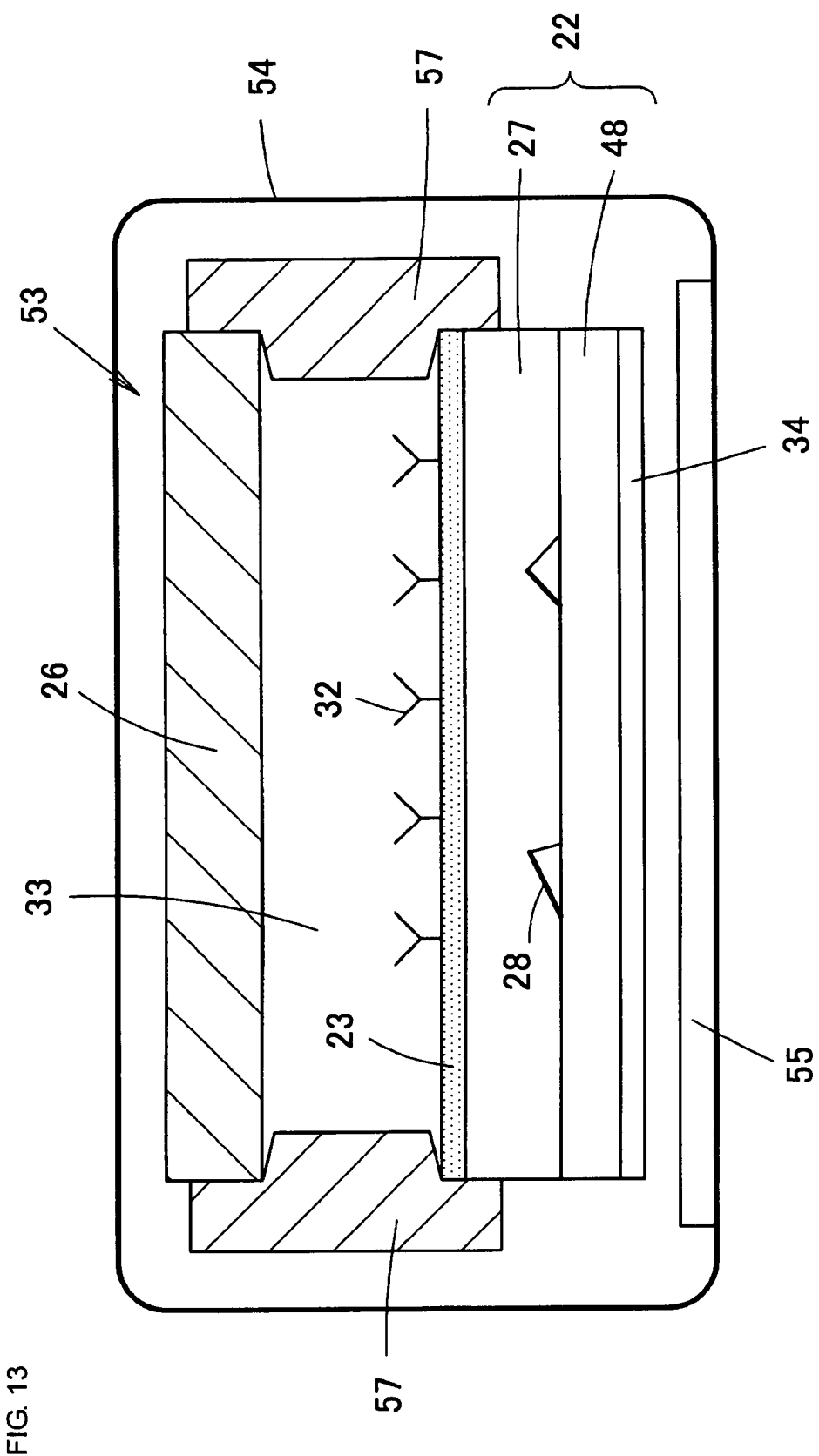
FIG. 13 shows a sectional view of another possible replacement component of the surface plasmon sensor in the embodiment 1 sealed in a moisture proof case.

In addition, as shown in FIG. 13, the replacement component 53 may include the channel cover 26. In this case, the channel cover 26 is integrally bonded to the upper surface of the metal layer 23, so that the light guide reflection plate 22 is sealed in the moisture proof case 54 with the channel cover 26 attached. In this case, since the antibody 32 is positioned in the channel 33, when an appropriate moisturizing agent such as a buffer is put in the channel 33 and both ends of the channel 33 are blocked with stoppers 57 which may be for example a rubber or flexible plastic as shown in FIG. 13, the antibody 32 is prevented from drying out. At the time of use, the replacement component 53 is taken out of the moisture proof case 54 and the stoppers 57 on both ends are removed. In this case, since the antibody 32 is not dried, it is not necessary to prepare the sponge 56 containing water (the sponge 55 containing the matching oil may be eliminated), the replacement component 53 can be stored in a case having no moisture proofing, so that its handling can be simplified.

In addition, in the case where the light guide reflection plate 22 is exchanged as the replacement component 53, although in the very least, the light receiving cell 25a in the light receiving element 25 may be provided at the position to which the light L reflected by the metal layer 23 is incident, since the position of the reflection surface 28 could be changed with respect to each replacement component 53, the light receiving cells 25a may be provided on the whole light receiving element 25.

In addition, although the reaction between the antibody and the antigen is used in the embodiment 1, the surface plasmon sensor (biosensor) according to several embodiments of the present invention may be used when various kinds of proteins and DNA are fixed to the substrate and couplings between the proteins and between the DNA and protein are used. In addition, when an appropriate material is selected as the molecule recognition substance is fixed onto the metal layer, the biosensor can be used in measuring an organic or inorganic matter instead of the biological material (the same is true of the following embodiments).

Embodiment 2

Figure 14:
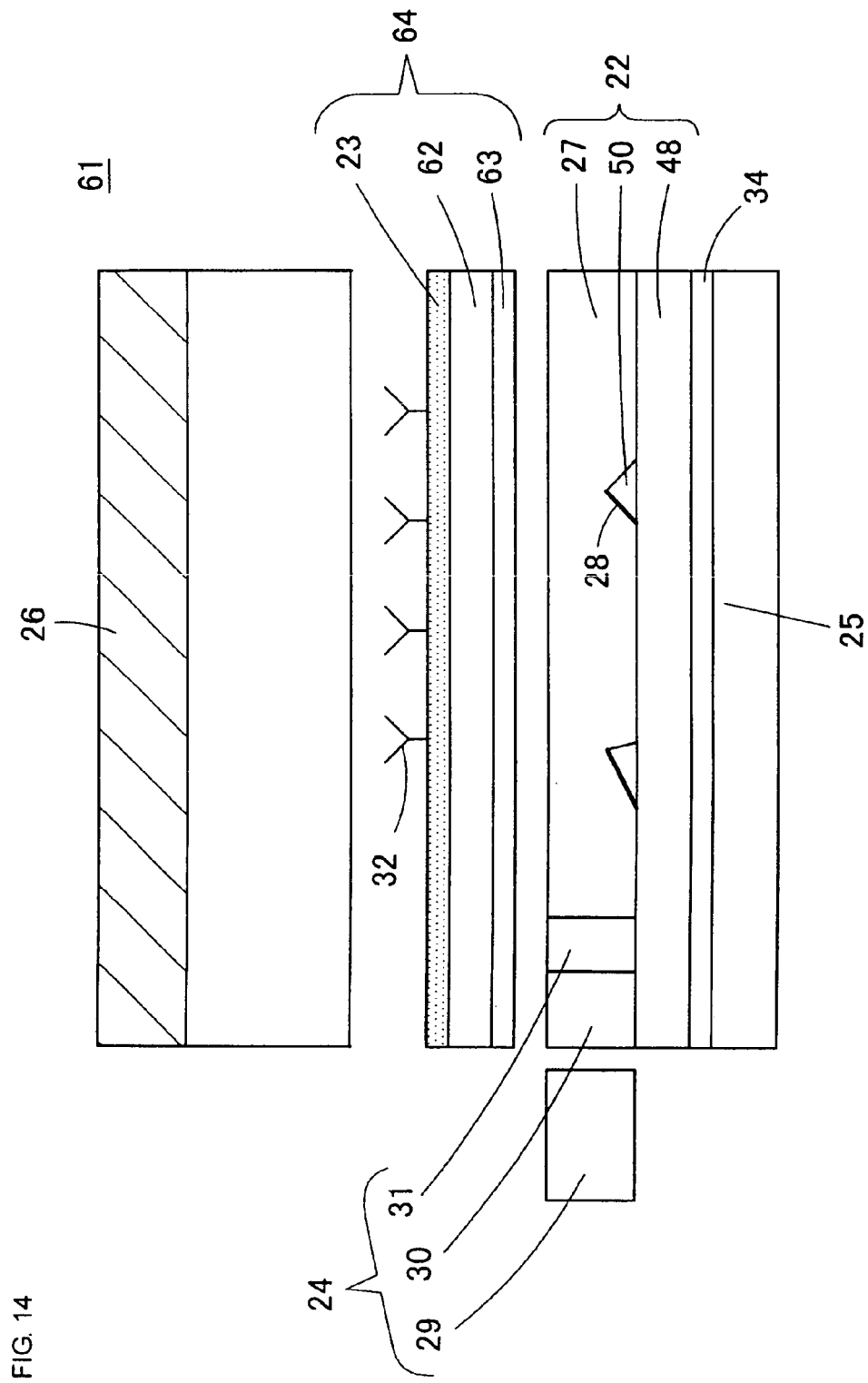
FIG. 14 shows an exploded sectional view of the structure of a surface plasmon sensor according to an embodiment 2 of the present invention.

FIG. 14 shows an exploded sectional view of the structure of a surface plasmon sensor 61 according to an embodiment 2. According to embodiment 2, a metal layer 23 is not provided directly on the upper surface of a light guide reflection plate 22, but formed on the upper surface of a relatively thin transparent auxiliary substrate 62, and a surface plasmon resonance layer includes the auxiliary substrate 62 and the metal layer 23. In the surface plasmon resonance layer according to this embodiment, the lower surface of the auxiliary substrate 62 is detachably attached to the upper surface of the light guide reflection plate 22 with a matching oil 63 sandwiched between them. The auxiliary substrate 62 includes a transparent glass substrate, a transparent resin plate, a transparent resin film, etc, and it may have the same refractive index as that of a light guide plate 27 of the light guide reflection plate 22. Although it is not shown, positioning means including a recession and a projection, etc is provided between the light guide reflection plate 22 and the auxiliary substrate 62. In addition, according to the surface plasmon sensor 61 of the embodiment 2, a polarizing element 30 and a collimator 31 that constitute a part of a light emitting unit 24 are incorporated in the light guide reflection plate 22 and a light source 29 is arranged opposite the polarizing element 30 buried in the light guide reflection plate 22.

Figure 15:
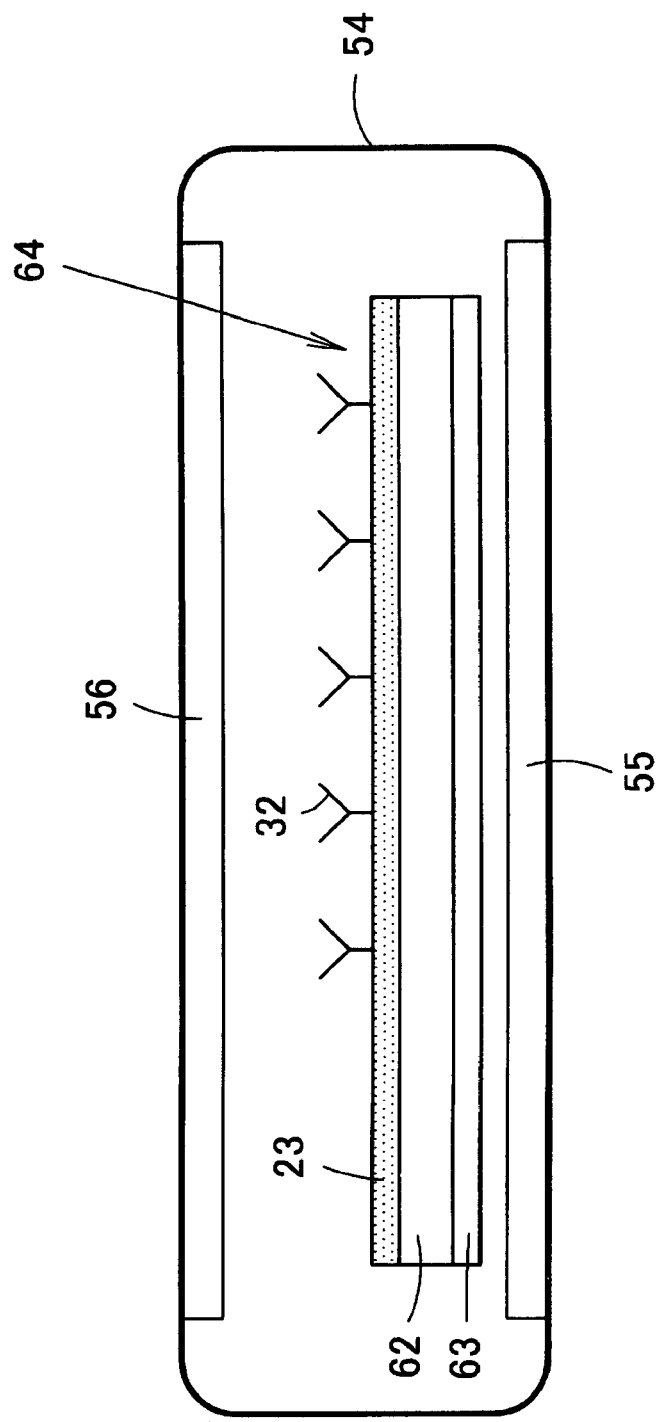
FIG. 15 shows a sectional view of a replacement component of the surface plasmon sensor of the embodiment 2 sealed in a moisture proof case.

According to this surface plasmon sensor 61, a replacement component 64 is provided such that an antibody 32 is fixed onto the metal layer 23 formed on the upper surface of the auxiliary substrate 62 and the matching oil 63 is thinly applied to the lower surface of the auxiliary substrate 62. This replacement component 64 is kept in a moisture proof case 54 as shown in FIG. 15.

According to the embodiment 2, since the light guide reflection plate 22 can be also repeatedly reused, the reusability of the surface plasmon sensor 61 is further improved. In addition, since the auxiliary substrate 62 can be manufactured at lower cost than the light guide reflection plate 22 incorporating a reflection surface 28, the replacement component 64 can be provided at lower cost than that of the embodiment 1.

In addition, the reflection surface 28 may be formed by forming a triangular recession on the lower surface of the light guide reflection plate 22 and forming a metal layer on the surface of the recession. That is, the reflection surface 28 may be formed in the recession provided in the lower surface of the light guide plate 27 and the lower surface of the light guide plate 27 becomes the lower surface of the light guide reflection plate 22 without providing a transparent substrate 48. However, in the case where the light guide reflection plate 22 is reused like in the embodiment 2, when the reflection surface 28 is sealed in the light guide reflection plate 22, the reflection surface 28 is not likely to be removed or damaged, so that high durability can be provided.

In addition, whether the polarizing element 30 and the collimator 31 are contained in the replacement component or not is determined in view of its measurement precision and cost. When the polarizing element 30 and the collimator 31 are contained in the replacement component, although it is not necessary to adjust positions between that optical system and the reflection surface 28, the number of manufacturing steps of the replacement component is increased and its manufacturing cost is also increased. Meanwhile, when they are not contained in the replacement component, although the manufacturing steps of the replacement component can be simplified and its manufacturing cost is reduced, optical adjustment could be necessary between the replacement component and the light emitting unit 24.

Figure 16:
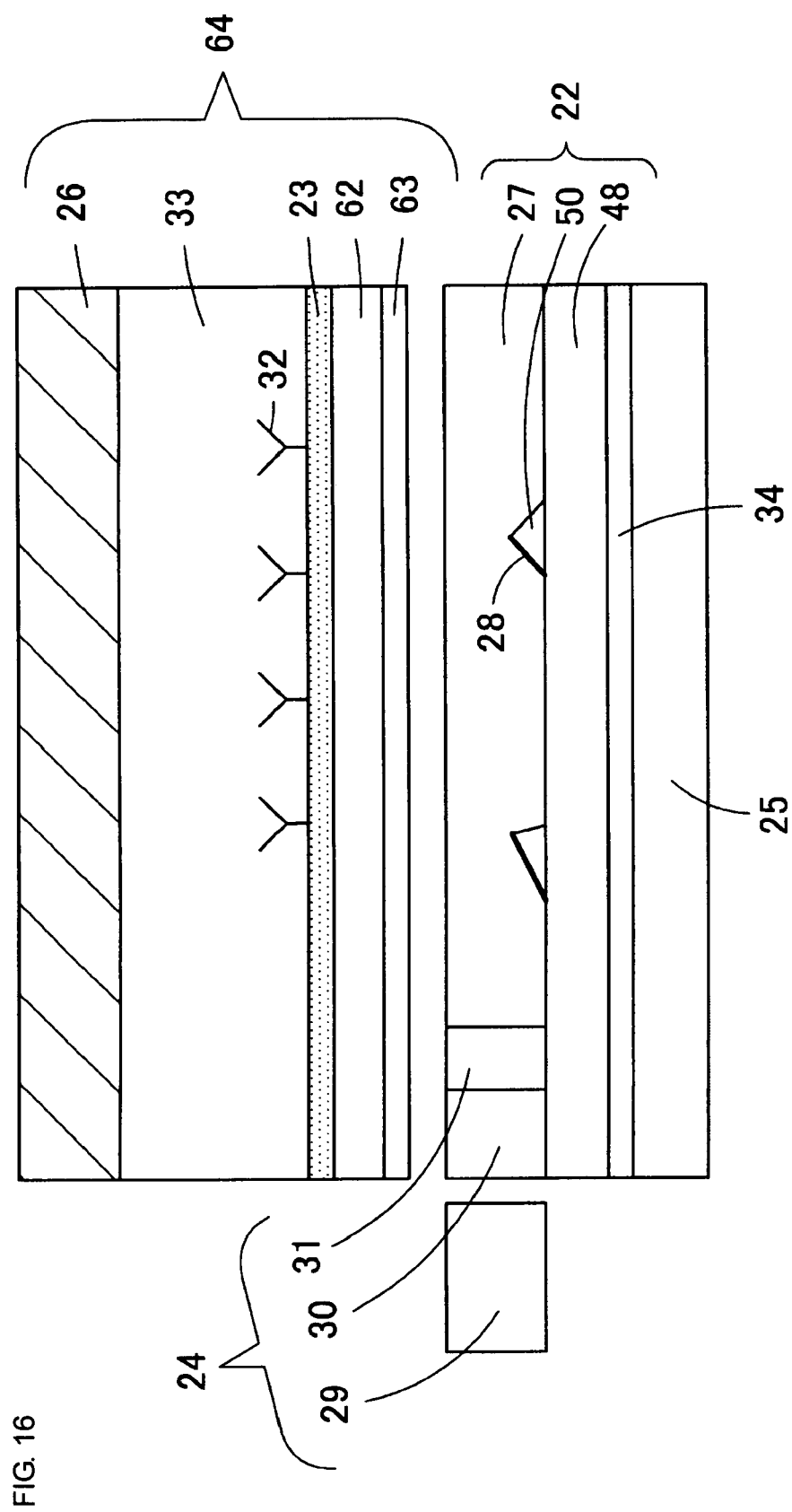
FIG. 16 shows a partially exploded sectional view of a variation of the embodiment 2.
Figure 17:
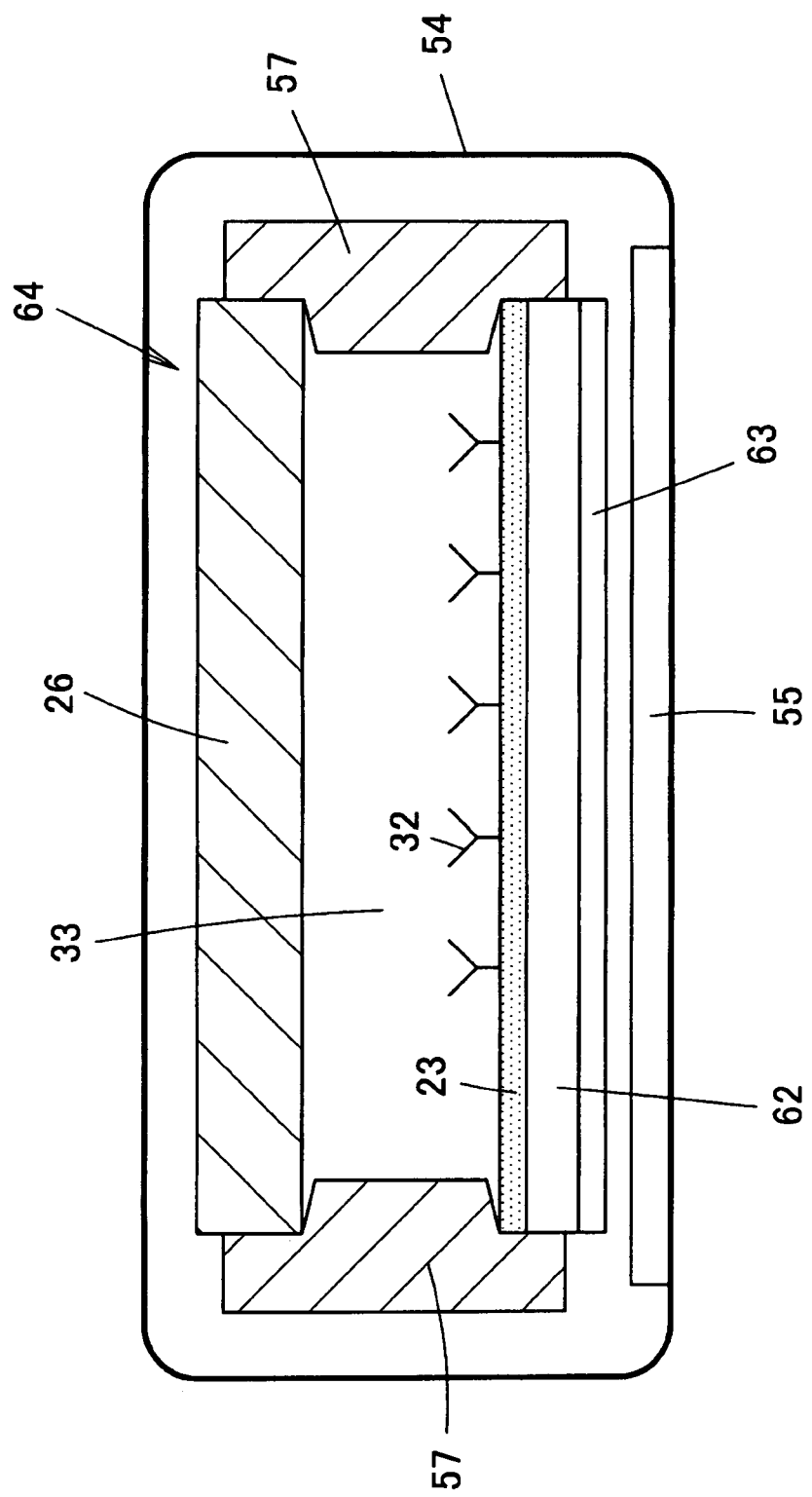
FIG. 17 shows a sectional view of a possible replacement component of the variation of the embodiment 2 sealed in a moisture proof case.

FIG. 16 shows a sectional view of a variation of the embodiment 2. According to this variation, a channel cover 26 is integrally bonded onto a metal layer 23 of an auxiliary substrate 62 and a replacement component 64 includes the auxiliary substrate 62 for forming a metal layer 23, an antibody 32, a matching oil 63 and the channel cover 26. Then, as shown in FIG. 17, an appropriate moisturizing agent such as a buffer is put in a channel 33 formed between the auxiliary substrate 62 and the channel cover 26, both ends of the channel 33 are blocked with stoppers 57, and the replacement component 64 is kept in a moisture proof case 54.

Embodiment 3

Figure 18:
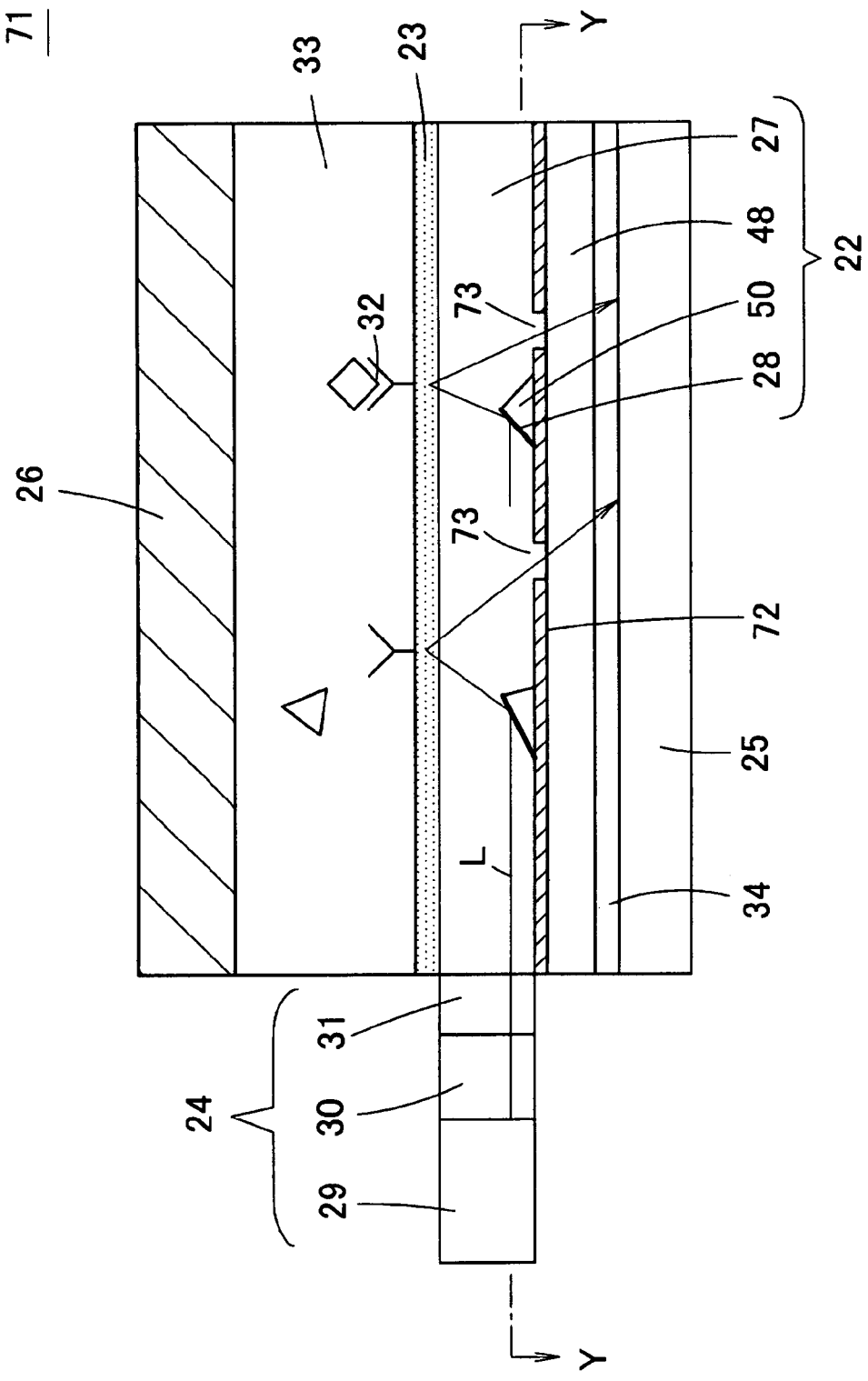
FIG. 18 shows a sectional view of a surface plasmon sensor according to an embodiment 3 of the present invention.
Figure 19:
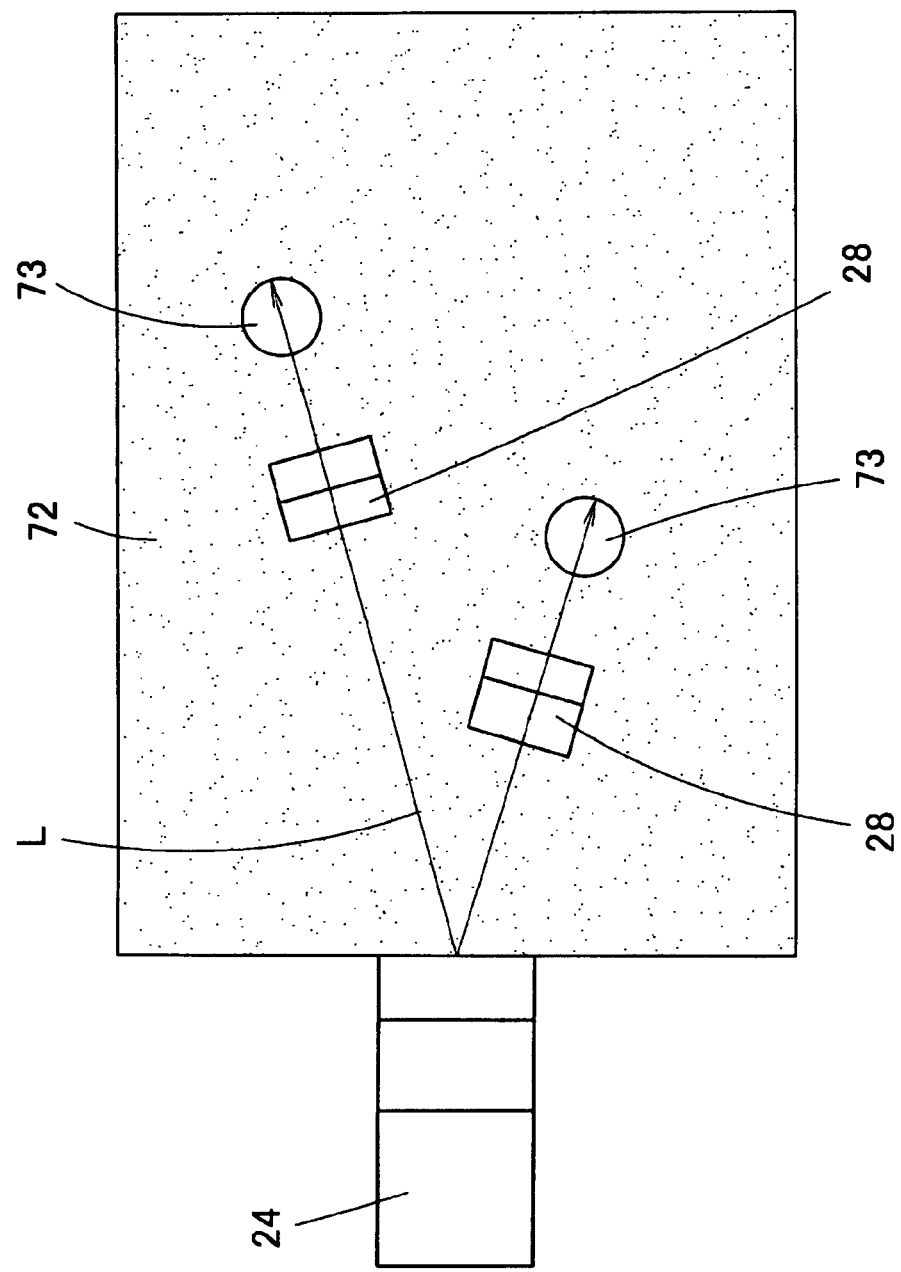
FIG. 19 shows a sectional view taken along a Y-Y line of FIG. 18.

FIG. 18 shows a sectional view of a surface plasmon sensor 71 according to an embodiment 3, and FIG. 19 shows a sectional view of a section (taken along a Y-Y line of FIG. 18) in a horizontal plane a reflection surface 28 is arranged. According to the surface plasmon sensor 71 of the embodiment 3, a light shielding part 72 impenetrable to light L is provided almost entirely between the upper surface of a transparent substrate 48 and the lower surface of a light guide plate 27 so as to almost correspond to a horizontal plane passing the lower end of a reflection surface 28. A transparent hole 73 is provided at a position through which the light L reflected by the reflection surface 28 and a metal layer 23 passes, in the light shielding part 72. The light shielding part 72 is preferably formed of a light-absorbing material such as a black film. The light shielding part 72 may be provided on the upper surface of the transparent substrate 48 by sputtering at the step shown in FIG. 10B or FIG. 10C. In addition, the transparent hole 73 is formed in the light shielding part 72 by partial sputtering when the light shielding part 72 is formed on the transparent substrate 48, or the transparent hole 73 is formed by etching or lift-off method after the whole-surface sputtering. A light emitting unit 24 emits light collimated in the vertical direction only so as to spread it out in a fan-like form in a horizontal plane.

According to the embodiment 3, since the light L except for the light needed in measurement can be prevented from entering a light receiving element 25 by the light shielding part 72, unnecessary light such as noise light and stray light reflecting diffusely in the light guide reflection plate 22 can be prevented from entering the light receiving element 25, and only the reflected light having a predetermined angle enters the light receiving element 25, so that measurement precision can be enhanced.

Figure 20:
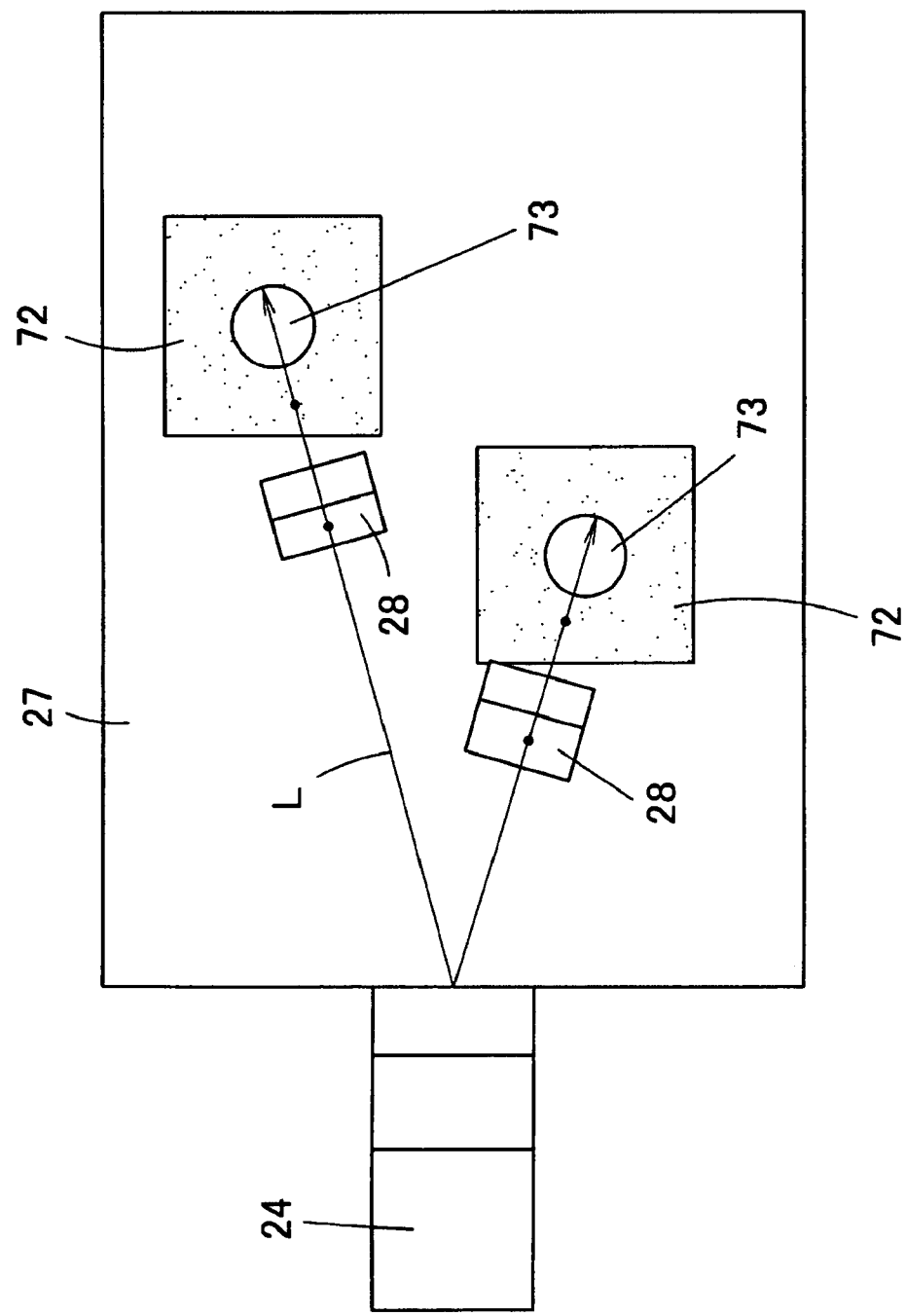
FIG. 20 shows a sectional view of a possible variation of the embodiment 3, corresponding to a sectional view taken along the Y-Y line of FIG. 18.

In addition, since the light L entering a light receiving cell 25a sufficiently apart from a light receiving cell 25a to which the reflected light having the predetermined angle is inputted does not affect the measurement precision, the light shielding part 72 may be provided only around the transparent hole 73 as shown in FIG. 20.

Figure 21:
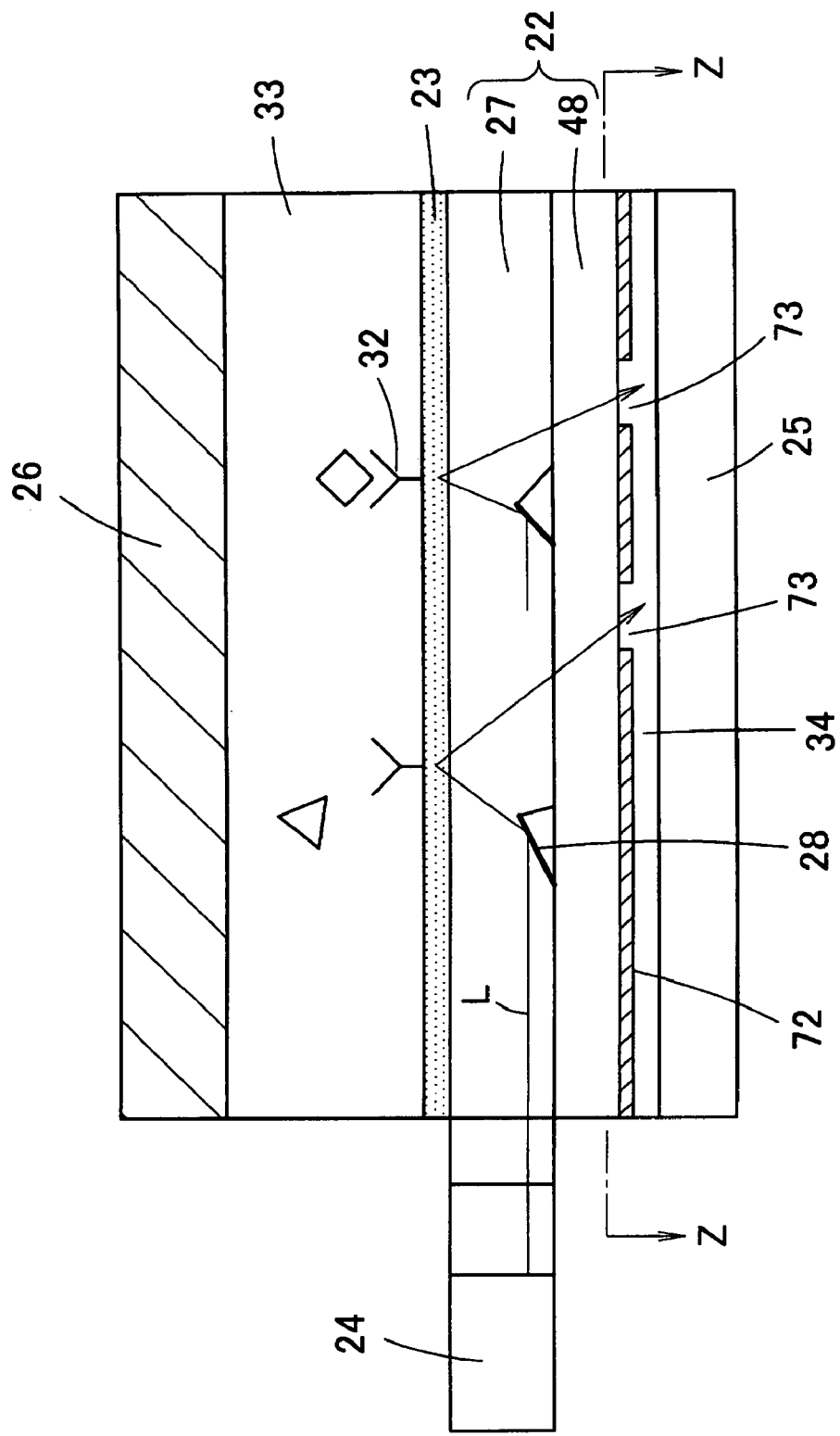
FIG. 21 shows a sectional view of another possible variation of the embodiment 3.
Figure 22:
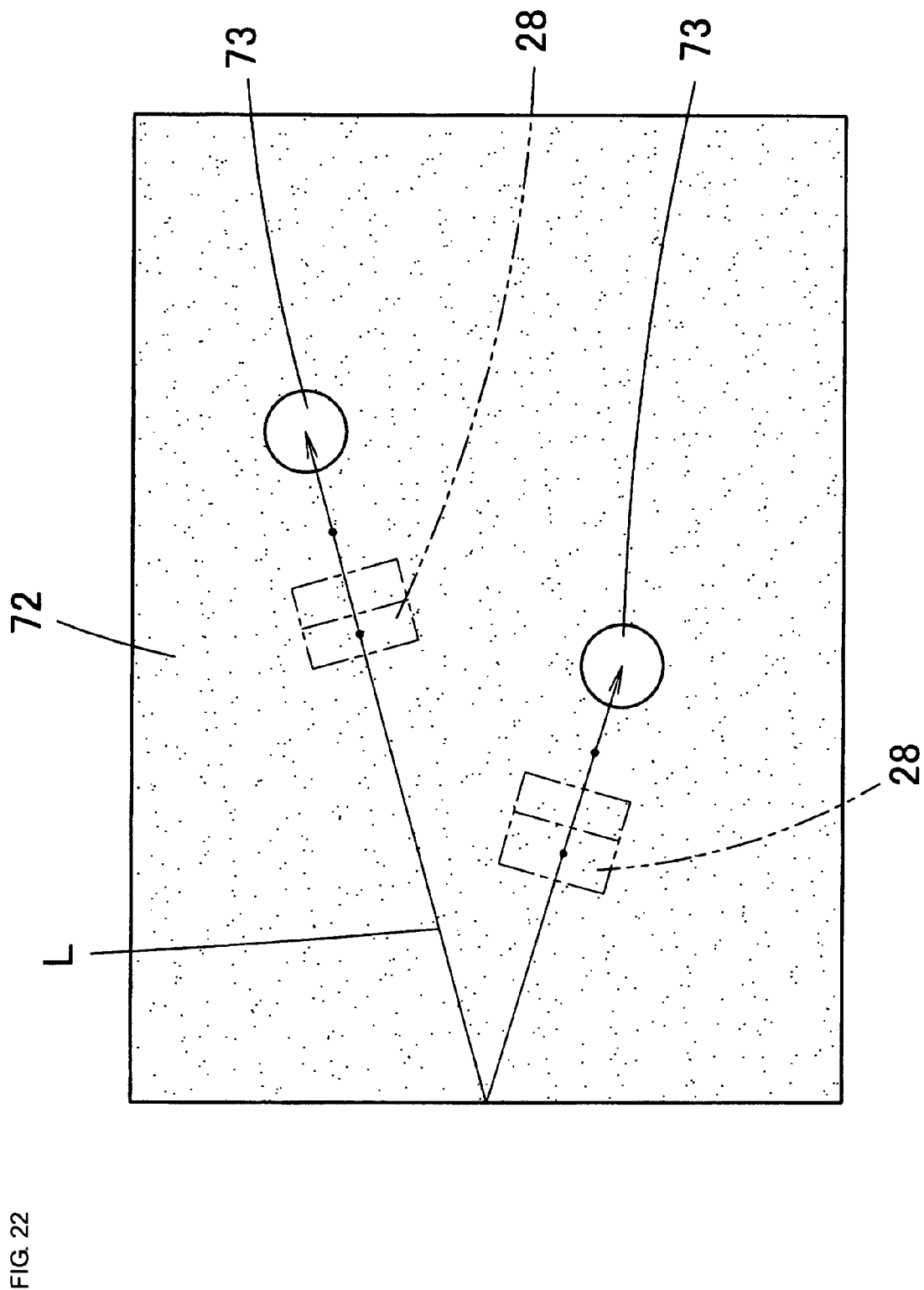
FIG. 22 shows a sectional view taken along a Z-Z line of FIG. 21.
Figure 23:
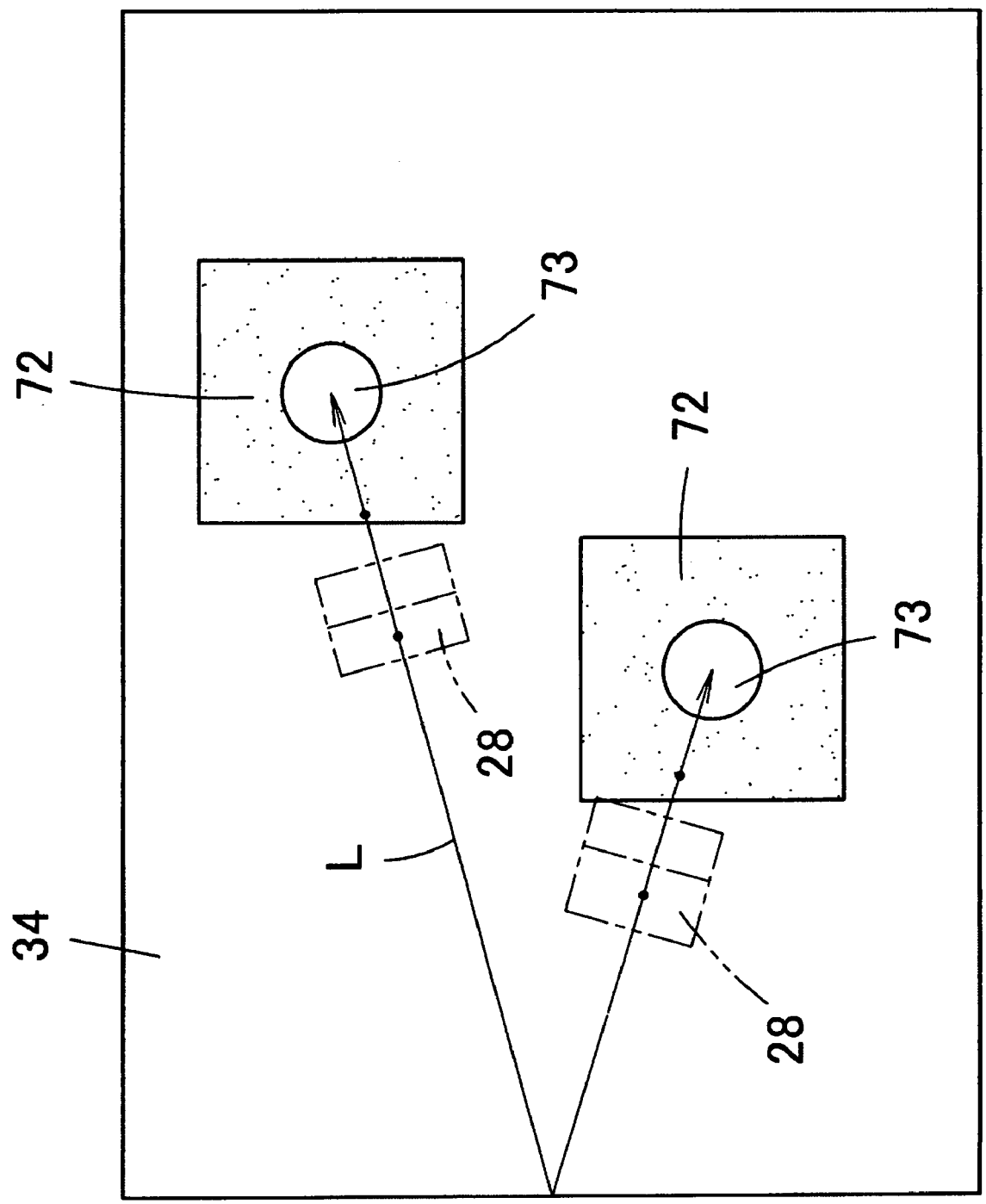
FIG. 23 shows a sectional view of yet another possible variation of the embodiment 3, corresponding to the sectional view taken along the Z-Z line of FIG. 21.

In addition, the light shielding part 72 may be positioned on any surface. For example, as shown in FIGS. 21 and 22, the light shielding part 72 is entirely provided on the lower surface of the light guide reflection plate 22 except for the transparent hole 73 to prevent the noise light and the stray light from entering the light receiving element 25. The light shielding part 72 may be formed on the lower surface of the light guide reflection plate 22 by partial sputtering at the manufacturing steps of the light guide reflection plate 22. In this case also, the light shielding part 72 may be provided only around the transparent hole 73 as shown in FIG. 23.

Figure 24:
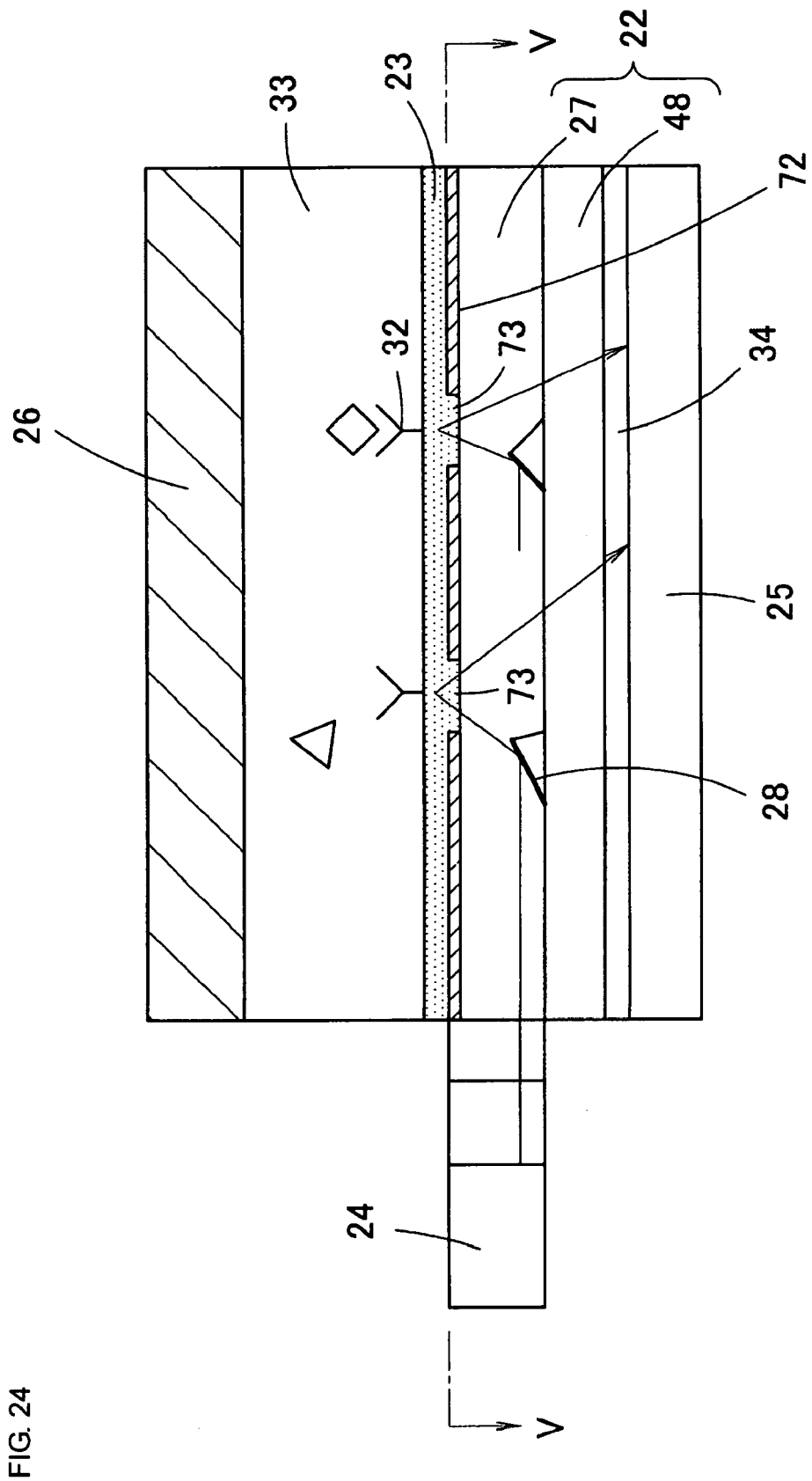
FIG. 24 shows a sectional view of yet another possible variation of the embodiment 3.
Figure 25:
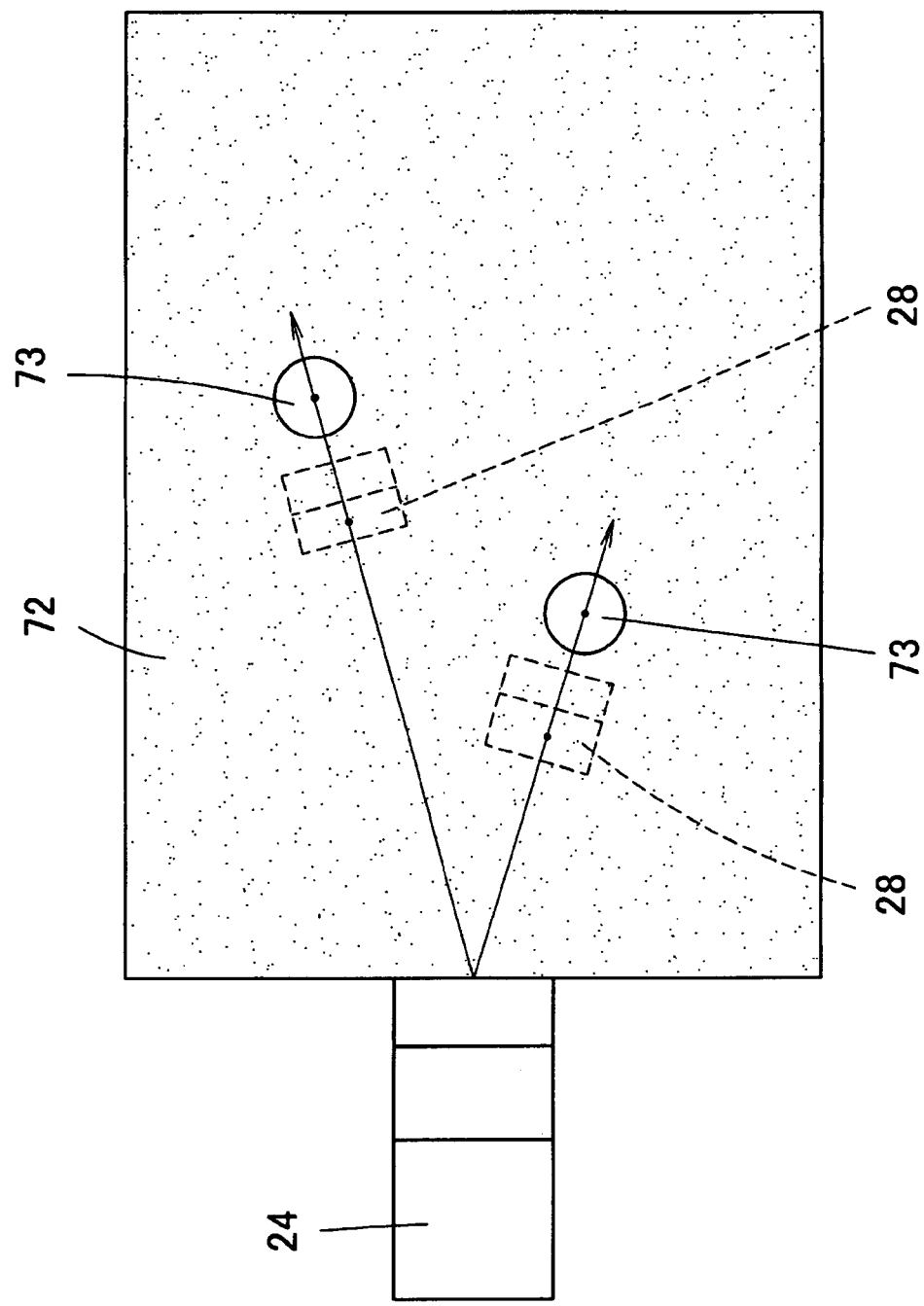
FIG. 25 shows a sectional view taken along a V-V line of FIG. 24.
Figure 26:
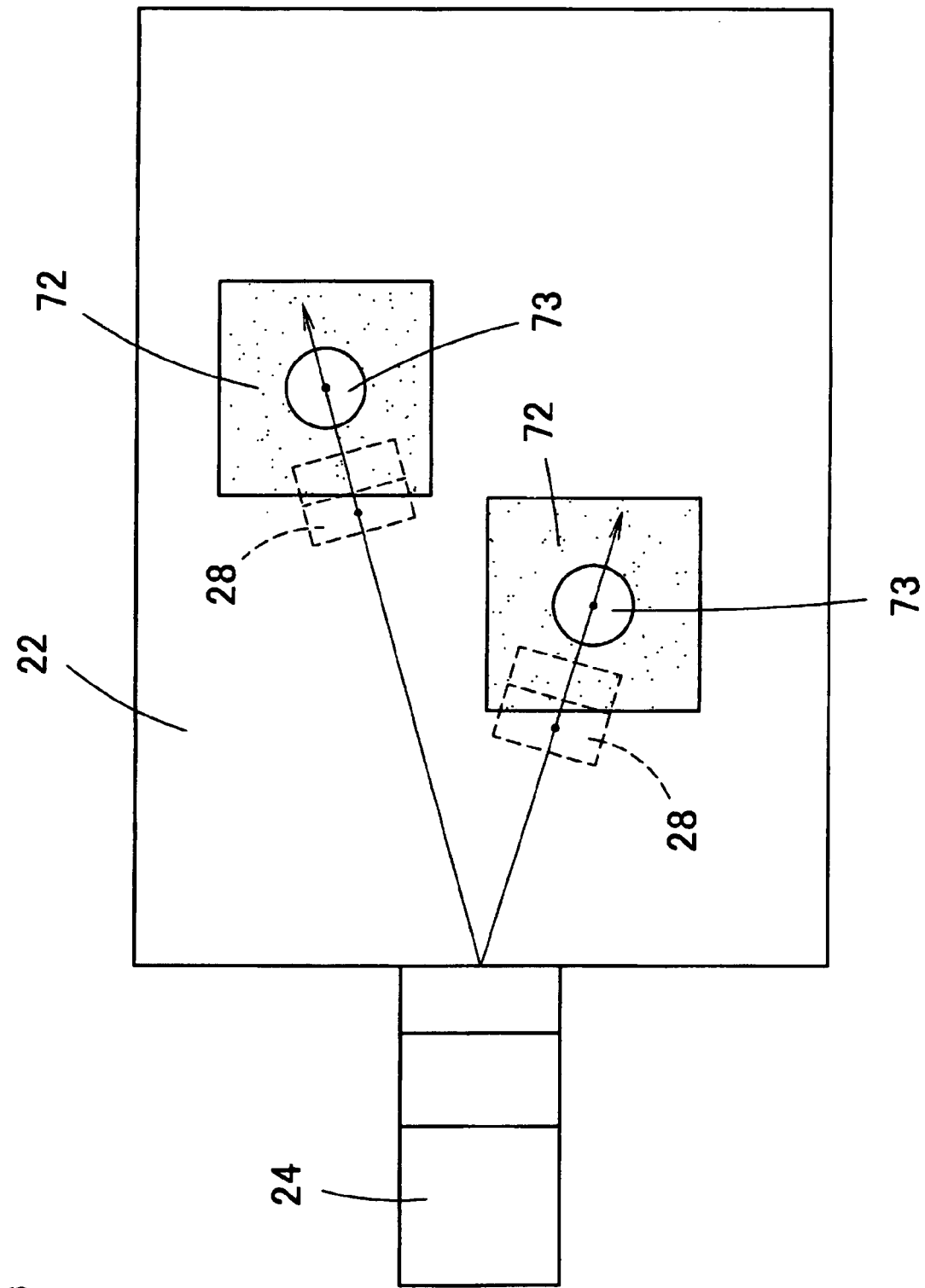
FIG. 26 shows a sectional view of yet another possible variation of the embodiment 3, corresponding to the sectional view taken along the V-V line of FIG. 24.

FIG. 24 shows a sectional view of a variation of the embodiment 3, and FIG. 25 shows a sectional view taken along a V-V line in FIG. 24. According to this variation, a light-absorbing light shielding part 72 is provided on the upper surface of a light guide reflection plate 22, and a transparent hole 73 is provided at the position in which light L reflected by a reflection surface 28 is reflected by the metal layer 23. According to this variation, since noise light and stray light in the light guide reflection plate 22 are reflected at the position in the metal layer 23 in which the reflected light from the reflection surface 28 is not inputted and can be prevented from entering the light receiving cell 25a used in measurement, the measurement precision of the surface plasmon sensor can be improved. The light shielding part 72 may be formed on the upper surface of the light guide reflection plate 22 by partial sputtering at the manufacturing step of the light guide reflection plate 22. In this case also, the light shielding part 72 may be provided only around the transparent hole 73 as shown in FIG. 26.

Embodiment 4

Figure 27:
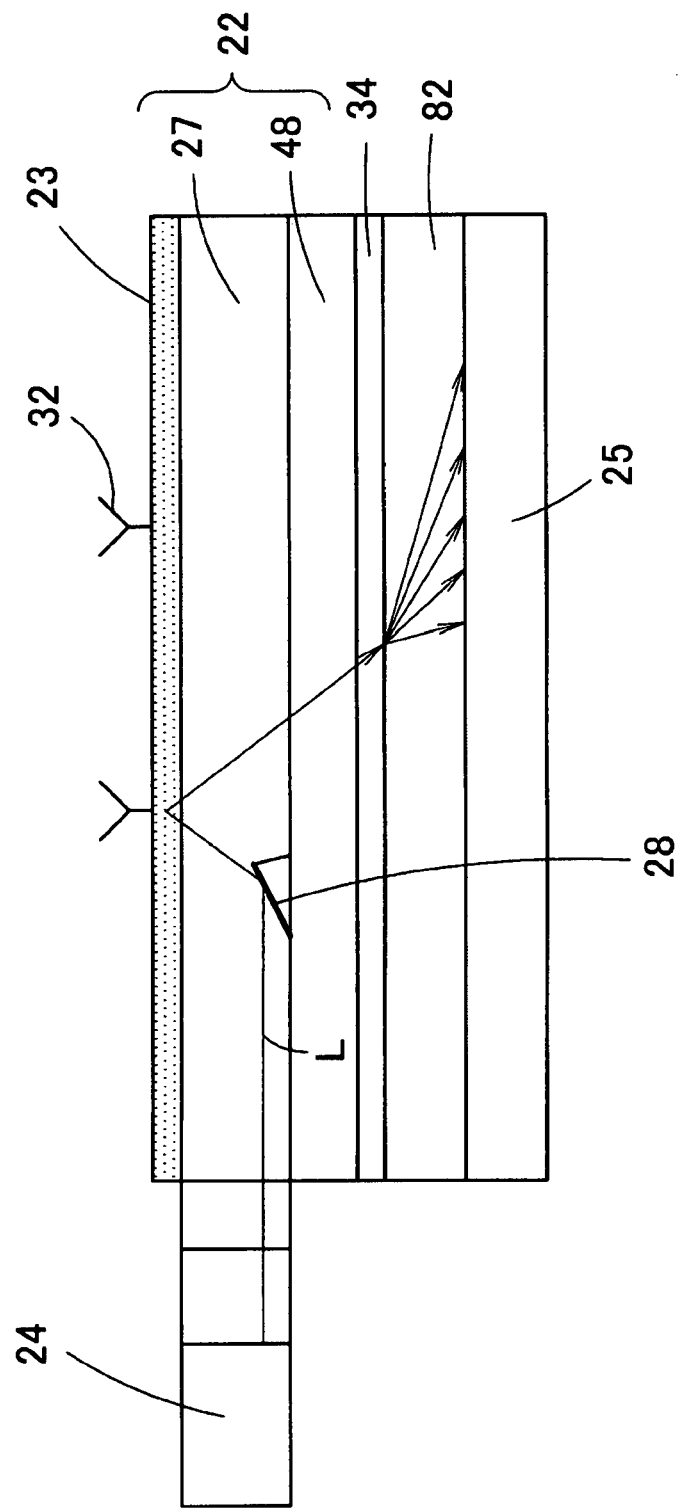
FIG. 27 shows a sectional view of the structure of a surface plasmon sensor according to an embodiment 4 of the present invention.

FIG. 27 shows a sectional view of the structure of a surface plasmon sensor 81 according to an embodiment 4 of the present invention. According to the embodiment 4, a spectral element 82 for example a diffraction grating is provided between a position in which light L reflected by a reflection surface 28 is inputted to a metal layer 23 and a light receiving element 25. For example, as shown in FIG. 27, the spectral element 82 is provided on the upper surface of the light receiving element 25. Thus, a light guide reflection plate 22 is adhered on the spectral element 82 with a matching oil 34 sandwiched between them. A light emitting unit 24 emits white light collimated only in the vertical direction in a fan-like form in a horizontal plane.

Thus, according to the above surface plasmon sensor 81, the white light is emitted from the light emitting unit 24 and the light L reflected by the reflection surface 28 is inputted to the metal layer 23 at a constant incident angle. The white light reflected by the metal layer 23 is inputted to the spectral element 82 to be dispersed into spectrum with respect to each wavelength and the light L from the spectral element 82 is inputted to different light receiving cells 25a.

Even the light L reflected by the metal layer 23 has the same incident and reflected angle in the metal layer 23, its variation in light intensity (variation in the light amount received by the light receiving cell 25a) depends on the wavelength of the light L. For example, when there is no reaction between an antibody and a antigen, a yellow component of the reflected light becomes dark because it is absorbed by plasmon resonance. Meanwhile, when there is the reaction between the antibody and the antigen, a green component of the reflected light becomes dark. In addition, although the variation in the color of the reflected light (light frequency) depends on the kind of the antibody, when the white light is emitted from the light emitting unit 24 and dispersed into spectrum by the spectral element 82, the measurement can be performed using the light L of a specific and any wavelength, so that measurement light of an optimum wavelength can be selected according to the kind of the antibody. That is, when one white light is reflected by the metal layer 23, the same effect provided when monochromatic light is inputted to the metal layer 23 at a plurality of incident angles can be provided, so that the number of surfaces at the region in which the antibody is fixed and the light L is inputted (referred to as the reflection surface region occasionally) can be reduced. Thus, according to the surface plasmon sensor 81 of the embodiment 4, since the number of reflection surfaces can be reduced, the surface plasmon sensor 81 can be further miniaturized.

Embodiment 5

Figure 28:
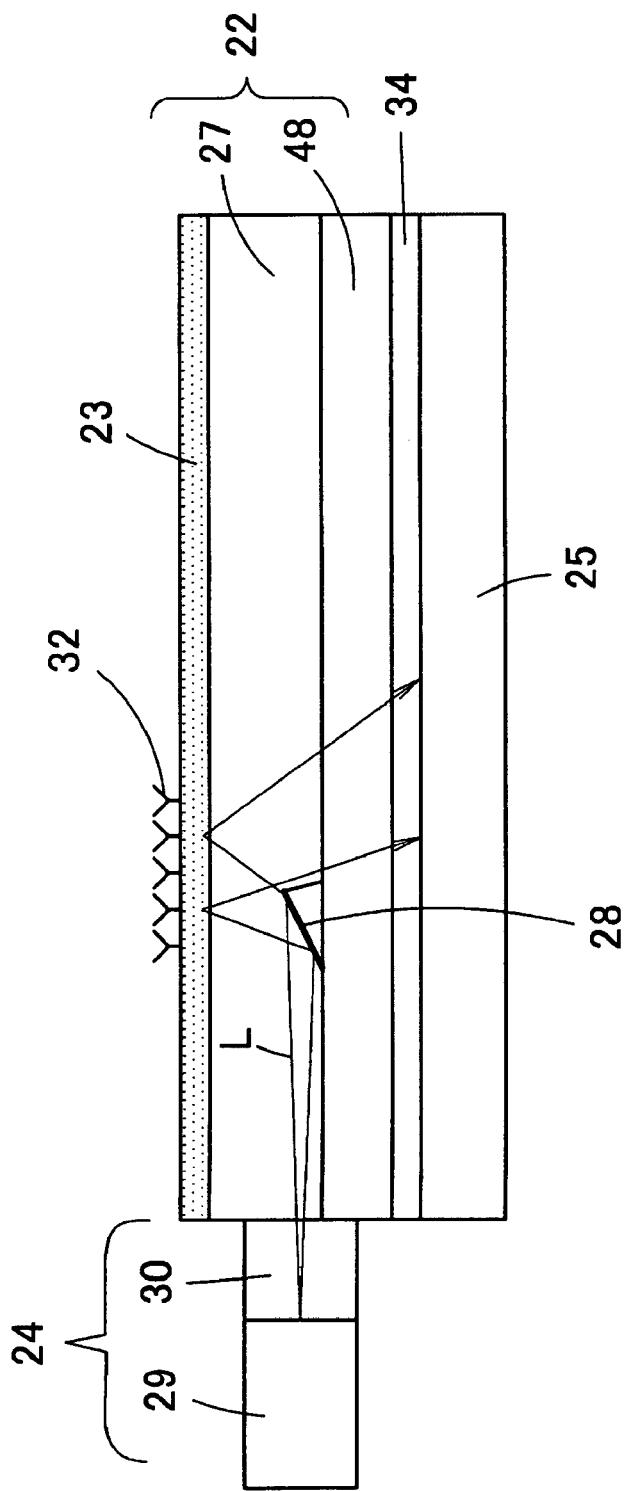
FIG. 28 shows a sectional view of the structure of a surface plasmon sensor according to an embodiment 5 of the present invention.

FIG. 28 shows a sectional view of the structure of a surface plasmon sensor 91 according to an embodiment 5 of the present invention. According to the surface plasmon sensor, a channel for flow of an inspection sample solution is not always necessary, and an inspection sample solution can be dropped from a pipette to a reflection surface region in which an antibody is fixed, for example. Therefore, in the following embodiment, the channel cover 26 is omitted except for a case where it has to be shown especially.

A light emitting unit 24 in the embodiment 5 does not comprise a collimator and includes a light source 29 and a polarizing element 30. Therefore, the light emitting unit 24 emits light L spreading in the vertical direction also. While the light L emitted from the light emitting unit 24 slightly spreads when viewed from the side direction of a light guide reflection plate 22 as shown in FIG. 29A, it largely spreads when viewed from the direction perpendicular to the upper surface of the light guide reflection plate 22 as shown in FIG. 29B. Alternatively, the light L emitted from the light emitting unit 24 may slightly spread when viewed from the side direction of the light guide reflection plate 22 as shown in FIG. 30A, and it may be emitted discretely toward each reflection surface 28 when viewed from the direction perpendicular to the upper surface of the light guide reflection plate 22 as shown in FIG. 30B.

According to the embodiment 5, since the light L emitted from the light emitting unit 24 spreads in the plane perpendicular to the upper surface of the light guide reflection plate 22, the spreading light L can be inputted to the reflection surface region, that is, the light L whose incident angles vary within a certain range can be inputted to the metal layer 23 by the one reflection surface 28. Therefore, the same effect as that in the case of the plurality of reflection surfaces having different inclined angles can be implemented with the one reflection surface 28 and detection can be implemented by the light L having incident angles that vary sequentially in one reflection surface region. As a result, while the same inspection is performed, the number of the surfaces at the reflection surface region can be reduced and the surface plasmon sensor 91 can be further miniaturized.

Figure 31:
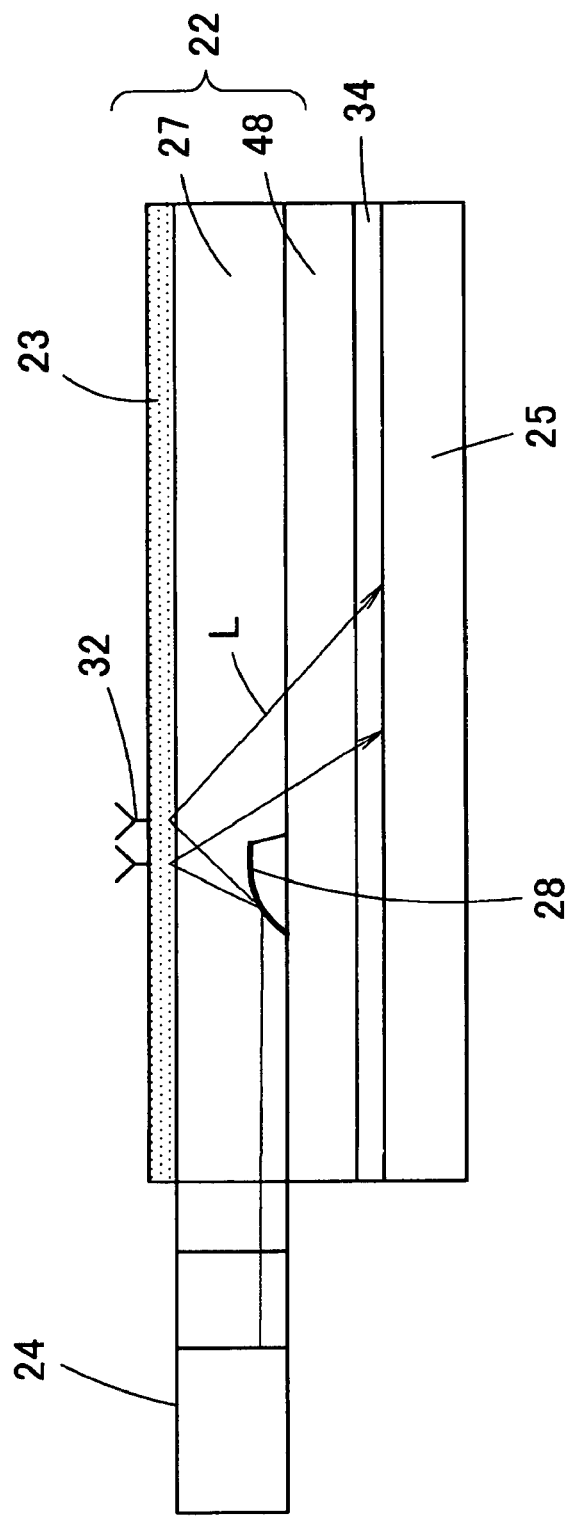
FIG. 31 shows a sectional view of the structure of a surface plasmon sensor according to a possible variation of the embodiment 5.

FIG. 31 shows a variation of the embodiment 5. According to this embodiment 5, similar to the light emitting unit 24 in the embodiment 1, a light emitting unit 24 emits light collimated in the vertical direction only in a fan-like form in a horizontal plane. Meanwhile, since a reflection surface 28 is curved like a convex mirror, similar to the embodiment 5, the radiating light L is inputted to the reflection surface region in which the antibody 32 is fixed. Thus, the same effect as that of the embodiment 5 can be provided in this variation also, and the surface plasmon sensor can be miniaturized.

Embodiment 6

Figure 32:
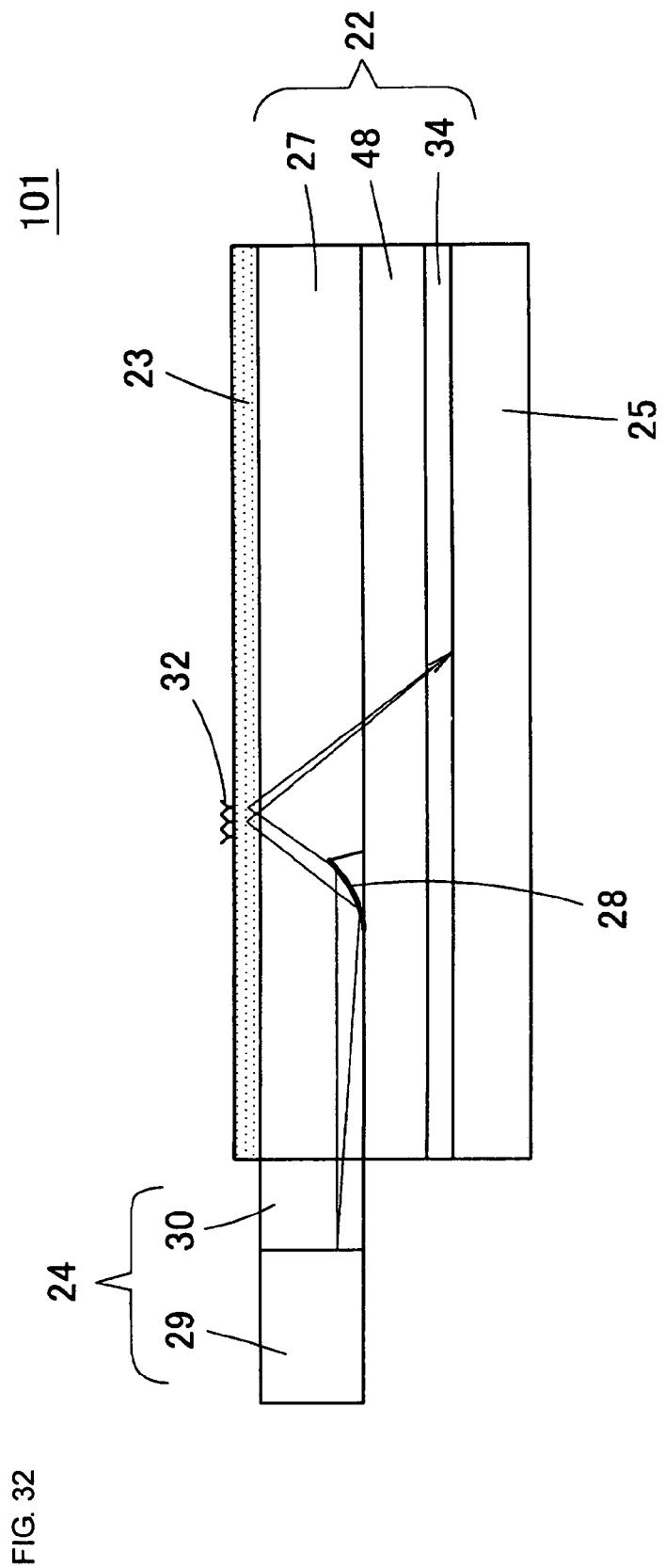
FIG. 32 shows a sectional view of the structure of a surface plasmon sensor according to an embodiment 6.

FIG. 32 shows a sectional view of the structure of a surface plasmon sensor 101 according to an embodiment 6. According to the surface plasmon sensor 101, light L slightly spreading in a plane perpendicular to a metal layer 23 is emitted from a light emitting unit 24. Meanwhile, a reflection surface 28 is curved like a concave mirror. This reflection surface 28 is designed such that after the light emitted from the light emitting unit 24 has been reflected by the reflection surface 28 and the metal layer 23, it is converged to a specific light receiving cell 25a.

Thus, according to this embodiment, even when the light L from the light emitting unit 24 spreads, the variation in incident angle of the light L inputted to the metal layer 23 can be reduced by converging the reflected light on the reflection surface 28, so that measurement precision can be improved.

In addition, the light L inputted to a certain reflection surface region at different incident angles and reflected there can be received by a specific light receiving cell 25a, so that the integration value of the intensity of the light L inputted to a certain reflection surface region at different angles and reflected there can be measured. Thus, in this embodiment also, while the same inspection is performed, the number of the surfaces at the reflection surface region can be reduced and the surface plasmon sensor 91 can be further miniaturized.

Embodiment 7

Figure 33:
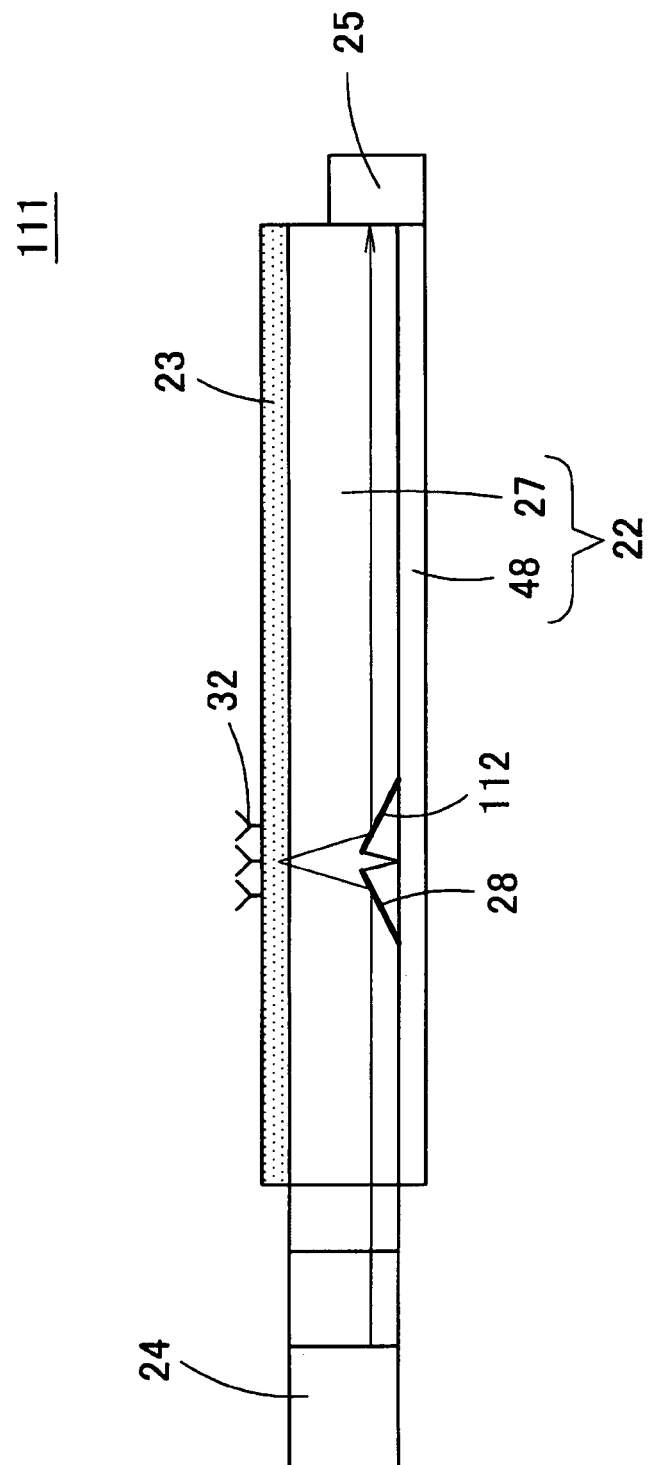
FIG. 33 shows a sectional view of the structure of a surface plasmon sensor according to an embodiment 7.

FIG. 33 shows a sectional view of the structure of a surface plasmon sensor 111 according to an embodiment 7. According to this surface plasmon sensor 111, a second reflection surface 112 is provided at the back of a reflection surface 28. The second reflection surface 112 has an inclined angle equal to that of the reflection surface 28, and inclined reversely. In addition, the second reflection surface 112 is arranged at a position that is approximately symmetric to the reflection surface 28 with respect to a perpendicular line provided at an inputted and reflected point on which the light L emitted from a light emitting unit 24 and reflected by the reflection surface 28 is inputted to a metal layer 23. The light emitting unit 24 emits light collimated in the vertical direction only in a fan-like form in a horizontal plane.

After the light L emitted from the light emitting unit 24 horizontally has been reflected by the reflection surface 28 and reflected by the metal layer 23, it is reflected by the second reflection surface 112 and its proceeding direction is changed in the horizontal direction again, reaches the end surface of the light guide reflection plate 22 opposite to the end surface on the side the light emitting unit 24 is arranged and emitted from the end of the light guide reflection plate 22 to the outside. Therefore, a light receiving element 25 is arranged at the end surface of the light guide reflection plate 22 opposite to the end surface in which the light emitting unit 24 is arranged so as to be able to receive the light L.

According to the surface plasmon sensor 111 in the embodiment 7, since the light receiving element 25 is arranged not on the lower surface of the light guide reflection plate 22 but at the end surface of the light guide reflection plate 22 like the light emitting unit 24, the surface plasmon sensor 111 can be further thinned. In addition, since the light receiving element 25 is arranged at the end surface of the light guide reflection plate 22, not an expensive CCD that is a two-dimensional light receiving element but a one-dimensional light receiving element such as a photodiode array can be used as the light receiving element 25, so that the surface plasmon sensor 111 can be provided at low cost.

Figure 34:
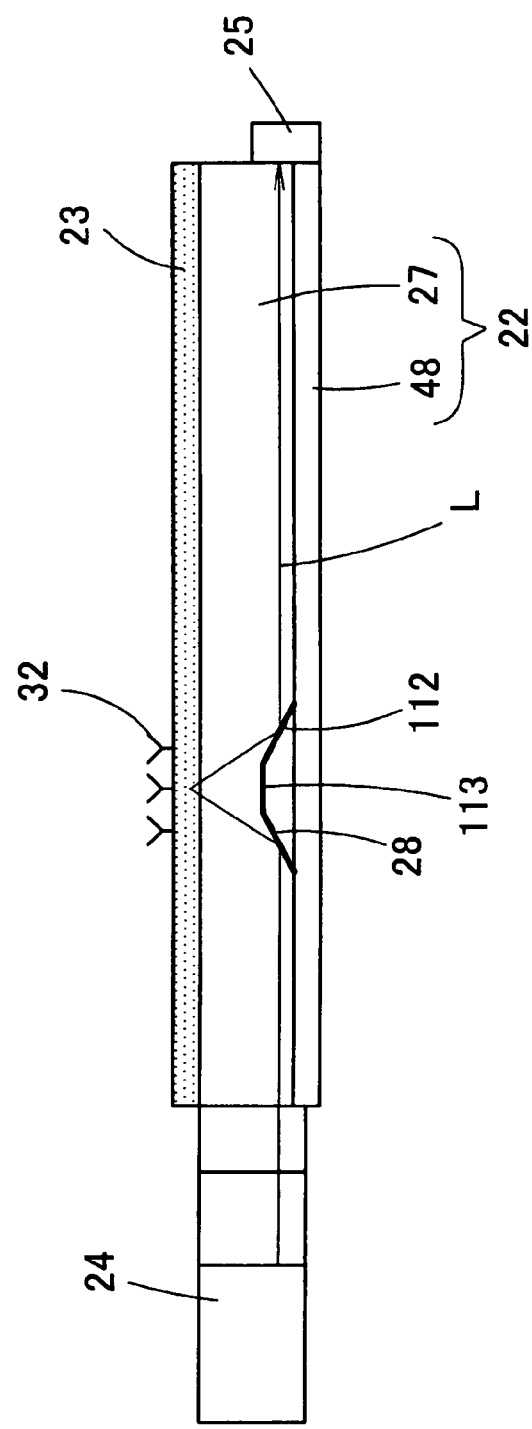
FIG. 34 shows a sectional view of the structure of a surface plasmon sensor according to a variation of the embodiment 7.

FIG. 34 shows a sectional view for explaining a surface plasmon sensor according to a variation of the embodiment 7. According to this variation, a third reflection surface 113 is formed between the upper end of a reflection surface 28 and the upper end of a second reflection surface 112, and the reflection surface 28 and the second reflection surface 112 are connected by the third reflection surface 113. According to this variation, since the reflection surface 28 and the second reflection surface 112 are connected by the third reflection surface 113, when the reflection surface 28 and the second reflection surface 112 are formed at the manufacturing step of the light guide reflection plate 22, the reflection surface can be easily manufactured.

Embodiment 8

Figure 35:
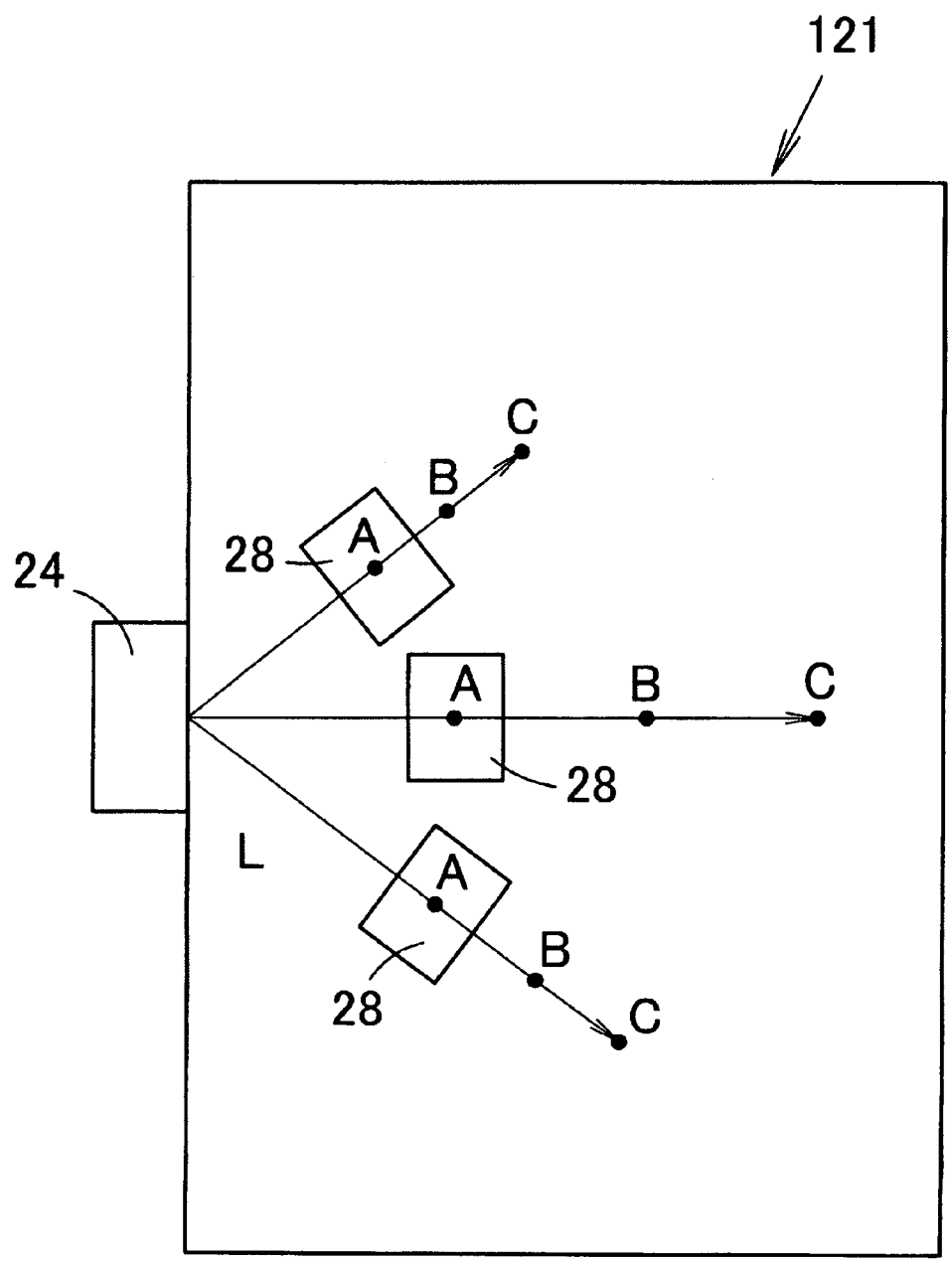
FIG. 35 shows a schematic view of a reflection point A in a reflection surface, a reflection point B in a metal layer and an incident point C on a light receiving element in the case of the embodiment 1.

FIG. 35 shows a schematic view of an inputted and reflected point A in the reflection surface 28, an inputted and reflected point B in the metal layer 23, and an inputted point C to the light receiving element 25 in the case of the embodiment 1. Since the light L emitted from the light emitting unit 24 radiates and the light L goes straight before and after reflected by the reflection surface 28 when viewed from the direction perpendicular to the upper surface of the light guide reflection plate 22, the area of the surface plasmon sensor 21 in the structure according to the embodiment 1 becomes large, so that miniaturization is limited.

Figure 36:
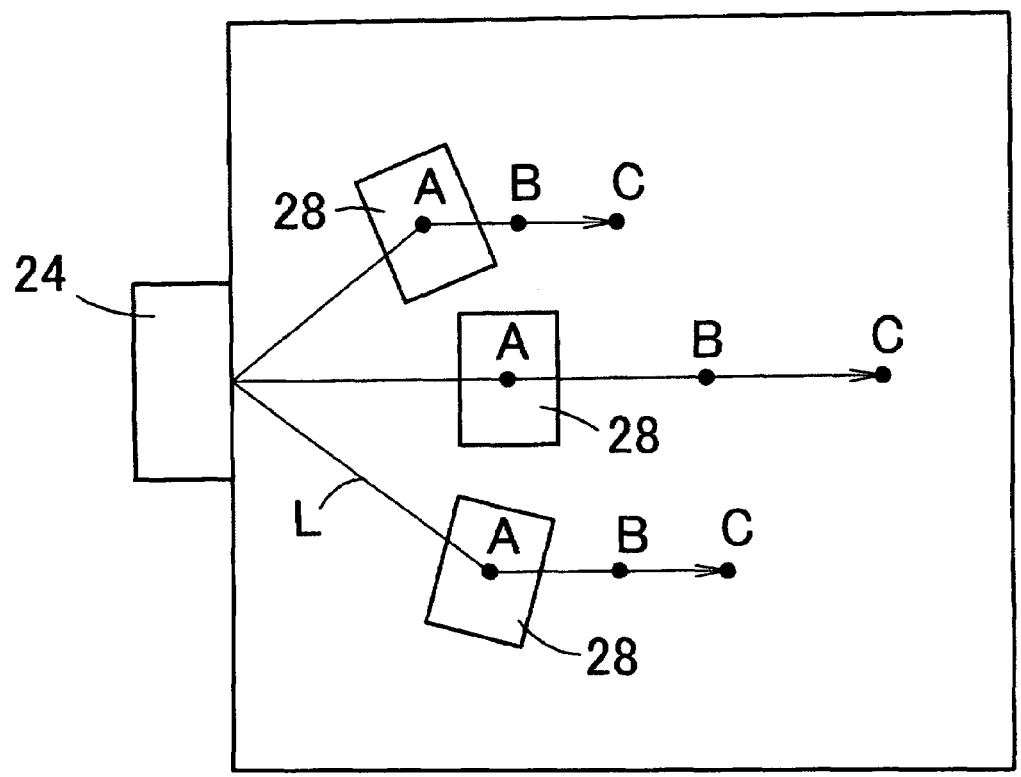
FIG. 36 shows a schematic view of a reflection point A in a reflection surface, reflection point B in a metal layer and an incident point C on a light receiving element in the surface plasmon sensor according to an embodiment 8.

Thus, according to a surface plasmon sensor 121 of an embodiment 8, a method for further miniaturizing it is proposed. FIG. 36 shows a schematic view of an inputted and reflected point A in a reflection surface 28, an inputted and reflected point B in a metal layer 23, and an inputted point C to a light receiving element 25 in the surface plasmon sensor 121 of the embodiment 8. According to the surface plasmon sensor 121 of the embodiment 8, the direction of the light L reflected by the reflection surface 28 is bent so that the reflected point in the metal layer 23 and the inputted point to a light receiving element 25 are converged to the center point when viewed from the direction perpendicular to the upper surface of a light guide reflection plate 22.

Thus, according to the above surface plasmon sensor 121, the surface plasmon sensor 121 is further miniaturized by narrowing the width of the surface plasmon sensor 121.

Figure 37:
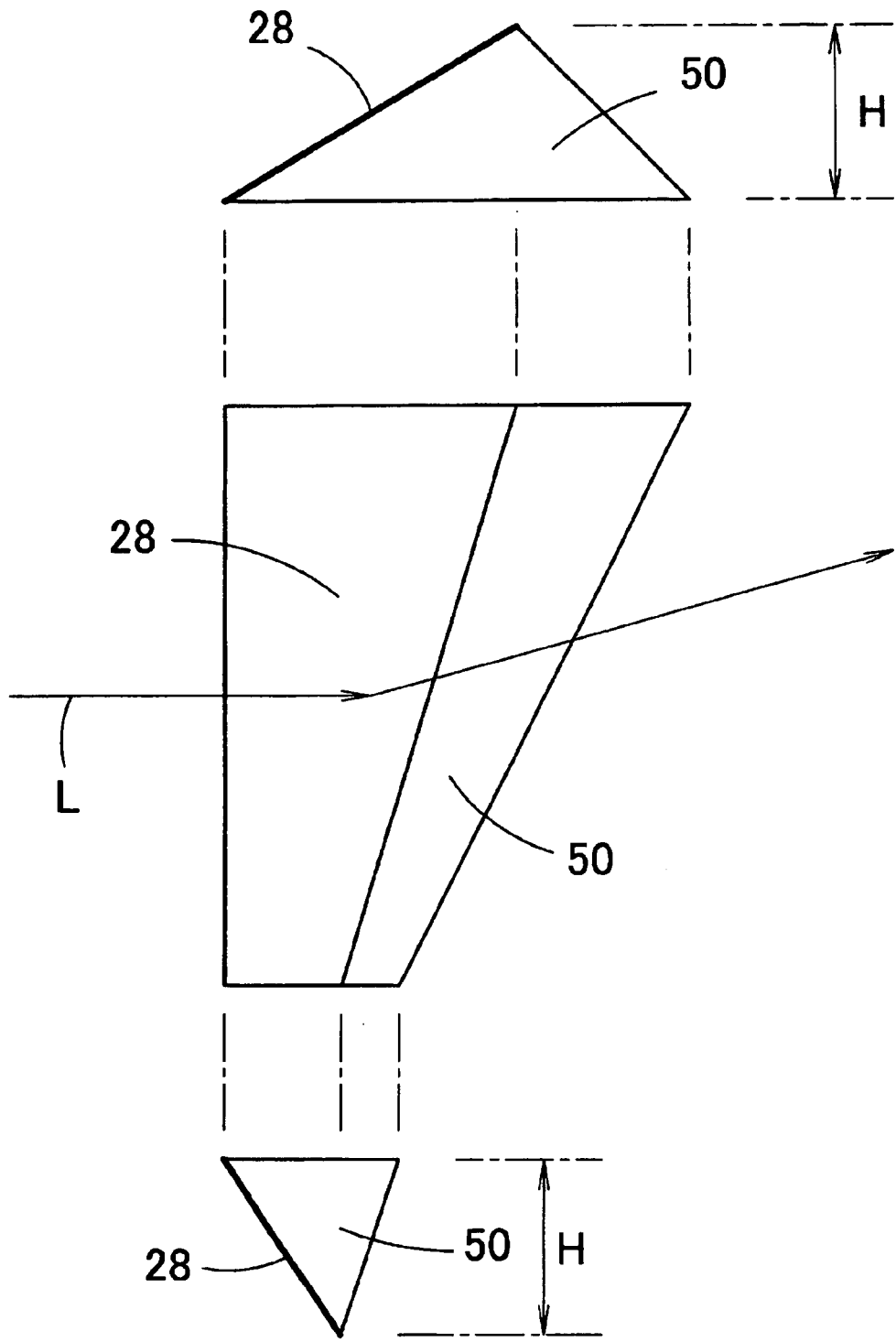
FIG. 37 shows a view of the planar configurations of a reflection surface and a projection and the configurations of both end surfaces to vary the direction of a reflected light.

In order to change the direction of the light L reflected by the reflection surface 28, the direction of the reflection surface 28 is to be changed. FIG. 37 shows the planar configurations of the reflection surface 28 and the projection 50 and configurations of the end surfaces on both sides. Although the height H of the reflection surface 28 is constant, the inclined angle of the reflection surface 28 varies along the width direction of the reflection surface 28 in FIG. 37. Therefore, as shown in FIG. 37, the light L reflected by the reflection surface 28 is bent in plane view also. According to such structure, since the inclined angle of the reflection surface 28 varies along the width direction of the reflection surface 28, the light L can be reflected at different inclined angles by the one reflection surface 28, so that the surface plasmon sensor 121 can be miniaturized.

Figure 38:
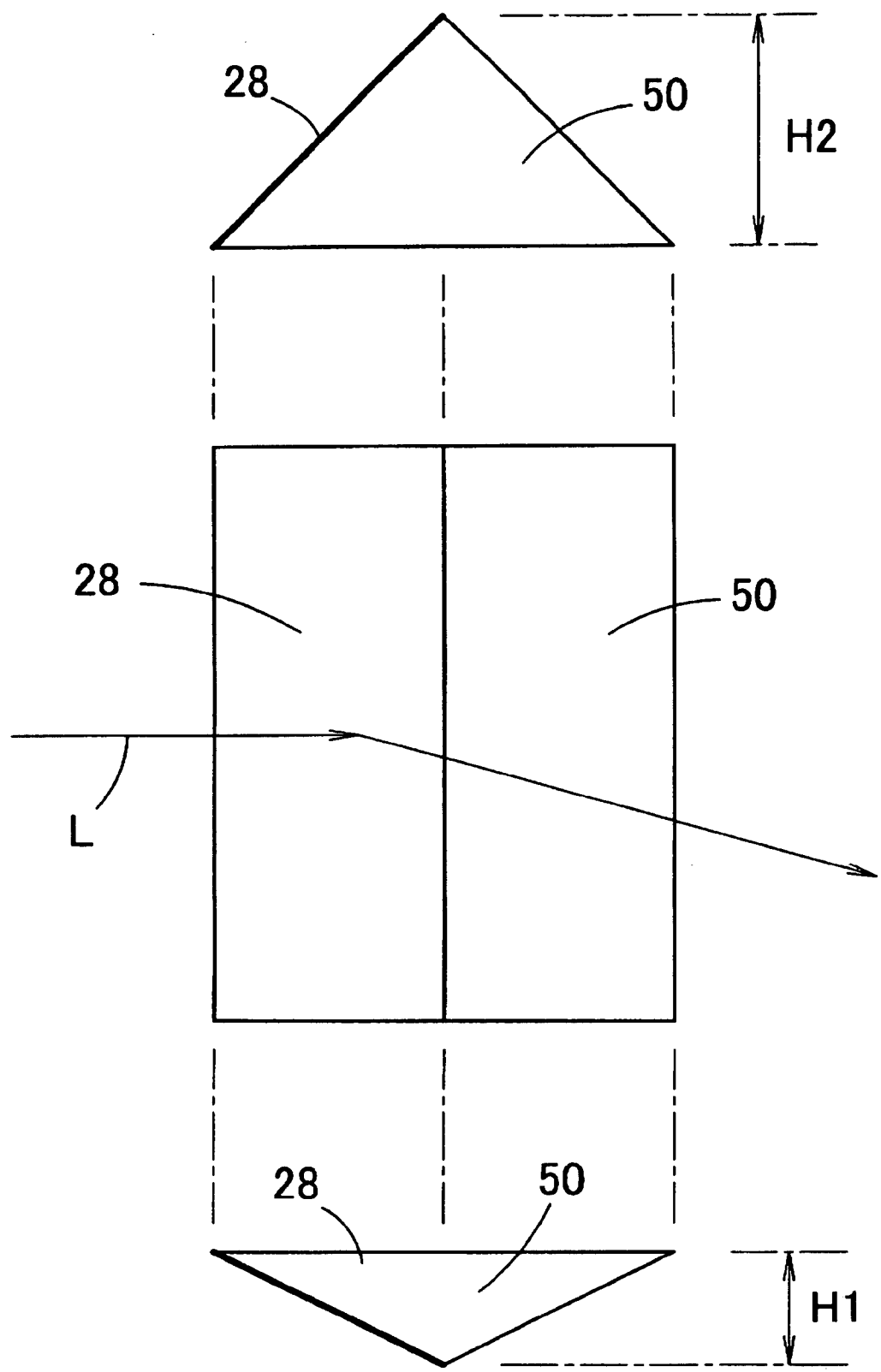
FIG. 38 shows a view of other planar configurations of the reflection surface and the projection and configurations of both end surfaces to vary the direction of a reflected light.

FIG. 38 shows the planar configurations of the reflection surface 28 and the projection 50 and configurations of the end surfaces on both sides. Although the vertical sectional configuration of any projection 50 is an isosceles triangle, the heights of the reflection surface 28 and the projection 50 vary along the width direction of the reflection surface 28, that is, the height at one end surface is H1 and the height at the other end surface is H2 (>H1) in FIG. 38. Therefore, as shown in FIG. 38, the light L reflected by the reflection surface 28 is bent in plane view also. According to such structure also, since the inclined angle of the reflection surface 28 varies along the width direction of the reflection surface 28, the light L can be reflected at different inclined angles by the one reflection surface 28, so that the surface plasmon sensor 121 can be miniaturized.

Figure 39:
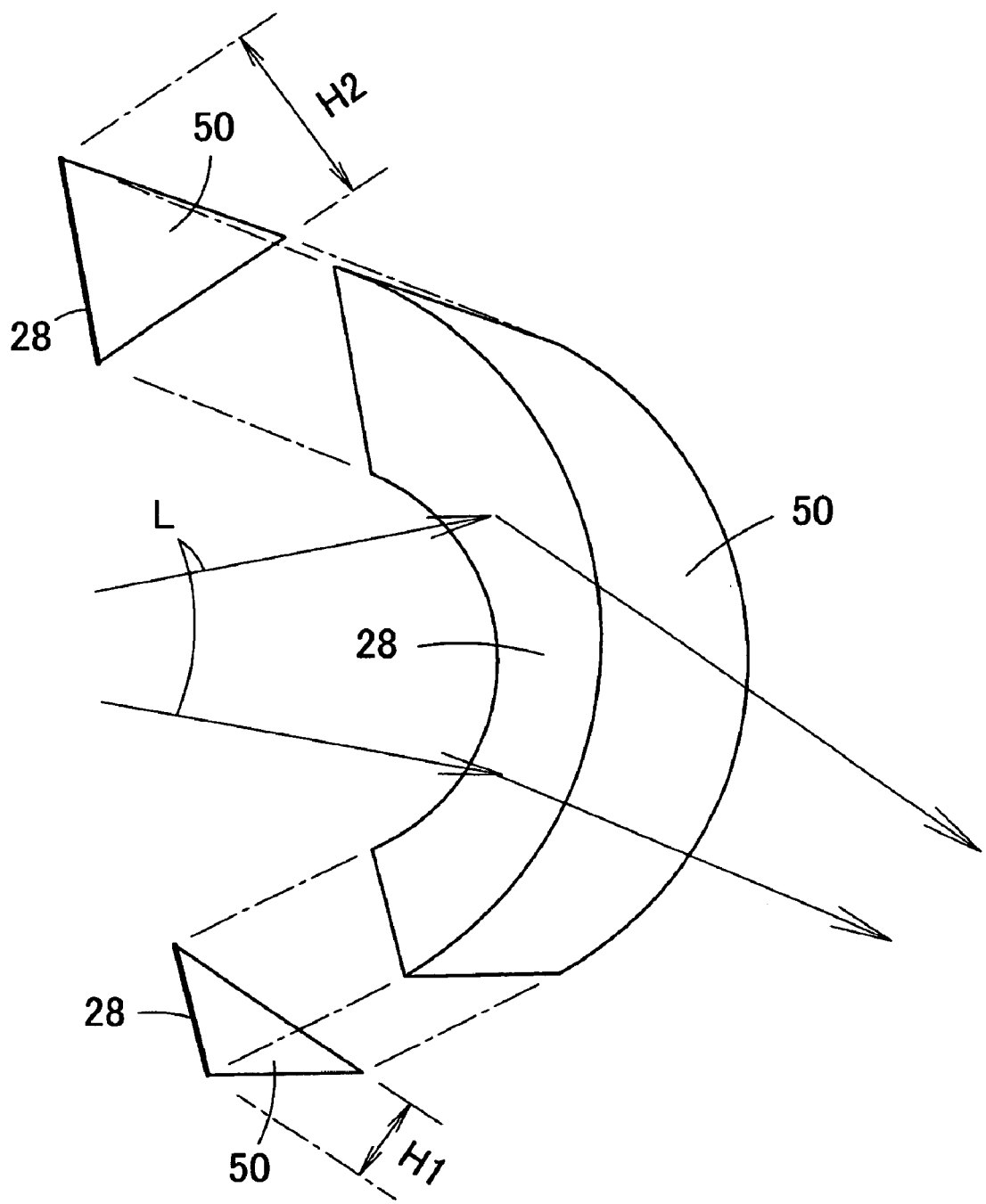
FIG. 39 shows a view of still other planar configurations of the reflection surface and the projection and configurations of both end surfaces to vary the direction of a reflected light.

Furthermore, as shown in FIG. 39, even when the light emitted from the light emitting unit 24 is diffused, the direction of the light L reflected by the reflection surface 28 can be bent and the reflected light can be converged by bending the reflection surface 28 and the projection 50.

Embodiment 9

Figure 40:
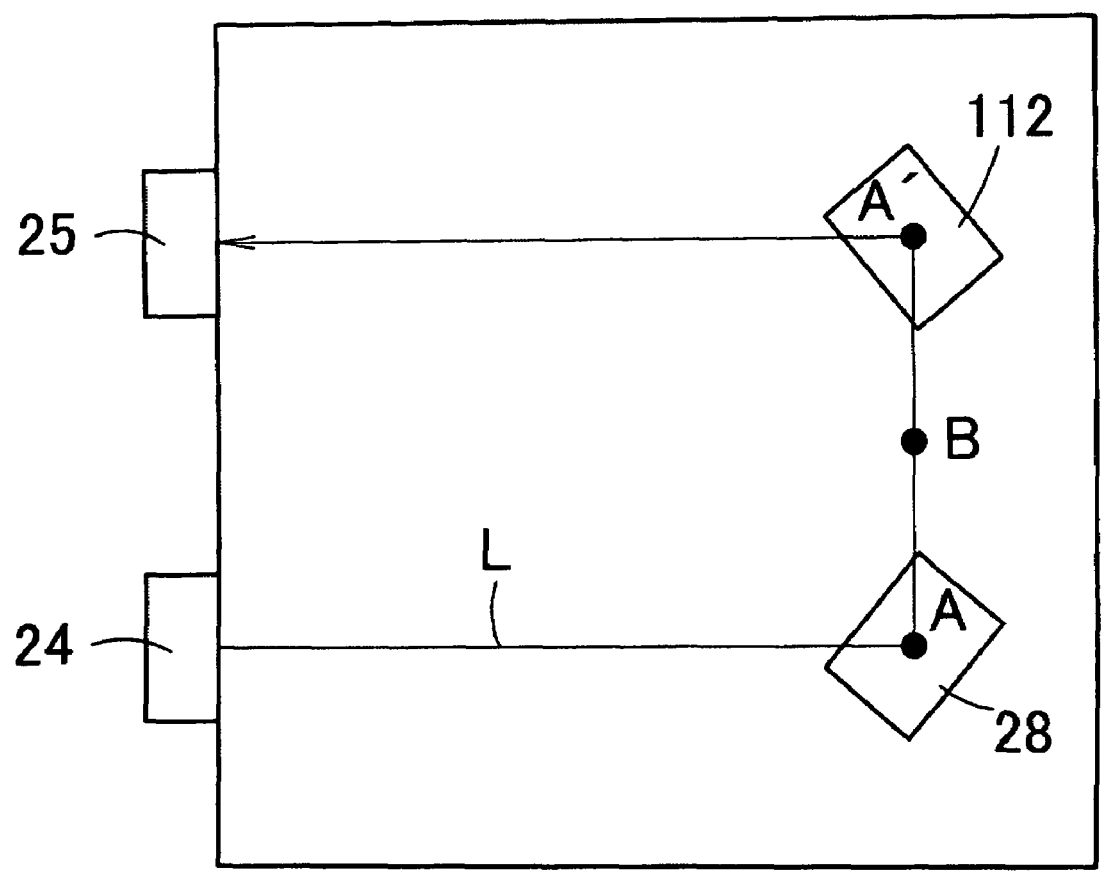
FIG. 40 shows a schematic view of a surface plasmon sensor according to an embodiment 9.

FIG. 40 shows a schematic view of a surface plasmon sensor 131 according to an embodiment 9 of the present invention. According to the embodiment 9, similar to the embodiment 7 (FIG. 33), light L from a light emitting unit 24 in the horizontal direction is inputted to a reflection surface 28, the light L reflected by the reflection surface 28 is inputted to a metal layer 23, the light L reflected by the metal layer 23 is inputted to a second reflection surface 112, the light L reflected by the second reflection surface 112 in the horizontal direction is received by a light receiving element 25 set at the end surface of a light guide reflection plate 22. In FIG. 40, a point A designates an inputted and reflected point of the light L in the reflection surface 28, a point B designates an inputted and reflected point of the light L in the metal layer 23, and a point A' designates an inputted and reflected point of the light L in the second reflection surface 112.

Furthermore, according to the surface plasmon sensor 131 in the embodiment 9, since the directions of the light L reflected by the light guide reflection plate 22 and the second reflection surface 112 are bent at an angle of 90 degrees with respect to the directions of the inputted light when viewed from the direction perpendicular to the upper surface of the light guide reflection plate 22, the light emitting unit 24 and the light receiving element 25 can be aligned on the same end surface of the light guide reflection plate 22, so that the surface plasmon sensor 131 can be easily assembled. In addition, since its length can be shortened as compared with the surface plasmon sensor 111 in the embodiment 7, the surface plasmon sensor 131 can be miniaturized.

Embodiment 10

Figure 41:
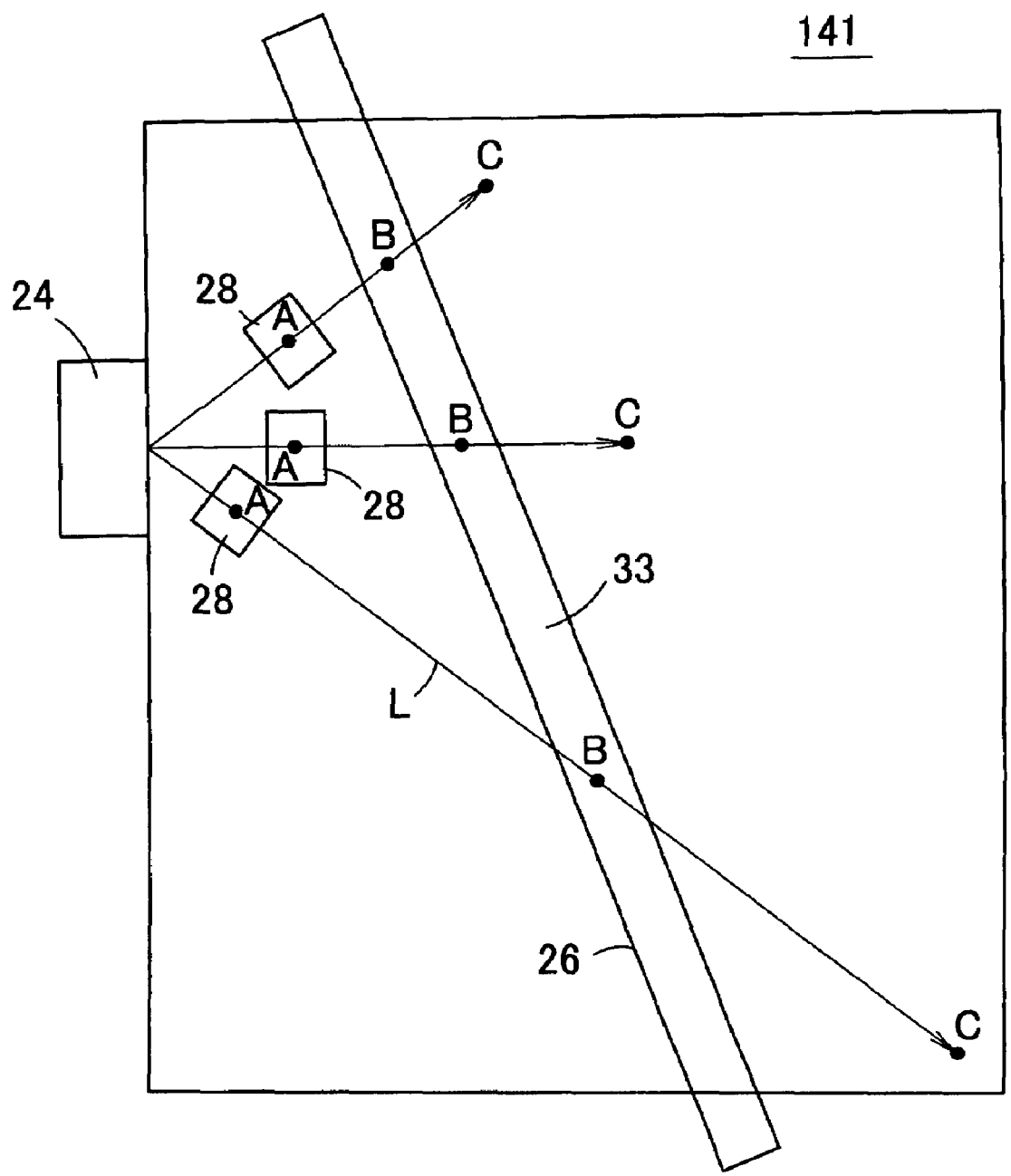
FIG. 41 shows a schematic view of a surface plasmon sensor according to an embodiment 10.

FIG. 41 shows a schematic view of a surface plasmon sensor 141 according to an embodiment 10 of the present invention. According to the surface plasmon sensor 141, a light emitting unit 24 and each reflection surface 28 are arranged so that inputted and reflected points B of light L reflected by reflection surfaces 28 may be aligned in a straight line in a metal layer 23. Thus, a narrow channel 33 is formed in a channel cover 26 so that it may pass the inputted and reflected points B of the light L in the metal layer 23.

According to the embodiment 1, since the channel 33 is formed on the whole upper surface of the metal layer 23, the sectional area of the channel 33 is large, so that the large amount of the inspection sample solution has to flow in the channel 33. Furthermore, when the inputted and reflected points B of the light L arranged arbitrarily are to be connected by a narrow channel, the channel could be curved or skewed and become a complicated form, which makes the control of the flow of the inspection sample solution difficult.

Meanwhile, according to the surface plasmon sensor 141 in the embodiment 10, since the inputted and reflected points B of the light L are aligned, the channel 33 can be narrowed and the measurement can be implemented by the small amount of the inspection sample solution. In addition, since the channel 33 for the inspection sample solution can be linear, the flow of the inspection sample solution can be easily controlled.

Figure 42:
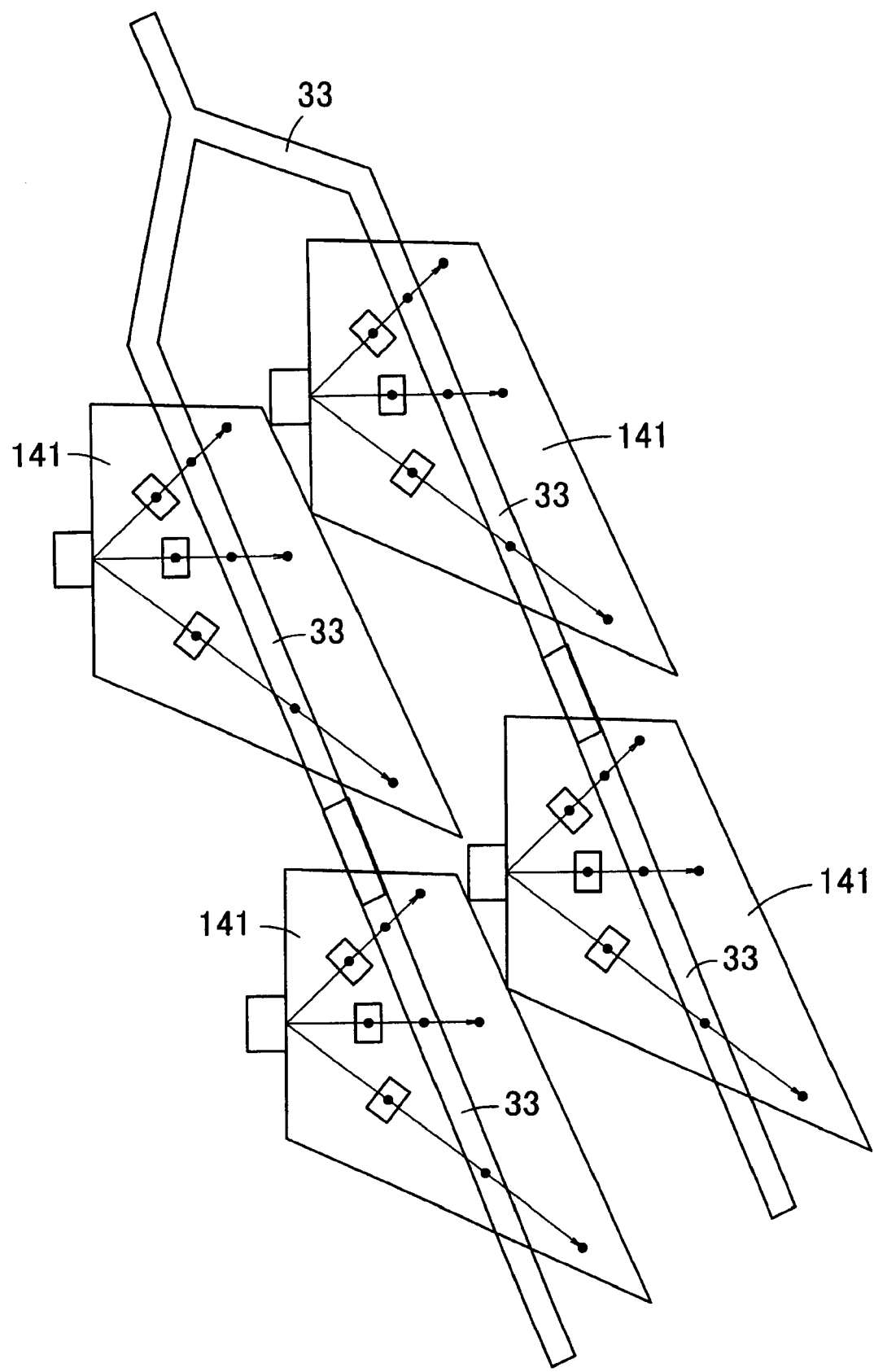
FIG. 42 shows a schematic view of a variation of the embodiment 10.

In addition, as shown in FIG. 42, when the plurality of surface plasmon sensors 141 are arranged in the same plane, and the channels 33 of the surface plasmon sensors 141 are linearly connected, or those channels 33 are arranged in parallel and connected to branched channels, the surface plasmon sensors 141 can be arrayed, so that the same inspection sample solution can be measured using different antibodies in the surface plasmon sensors 141 at the same time.

Embodiment 11

Figure 43:
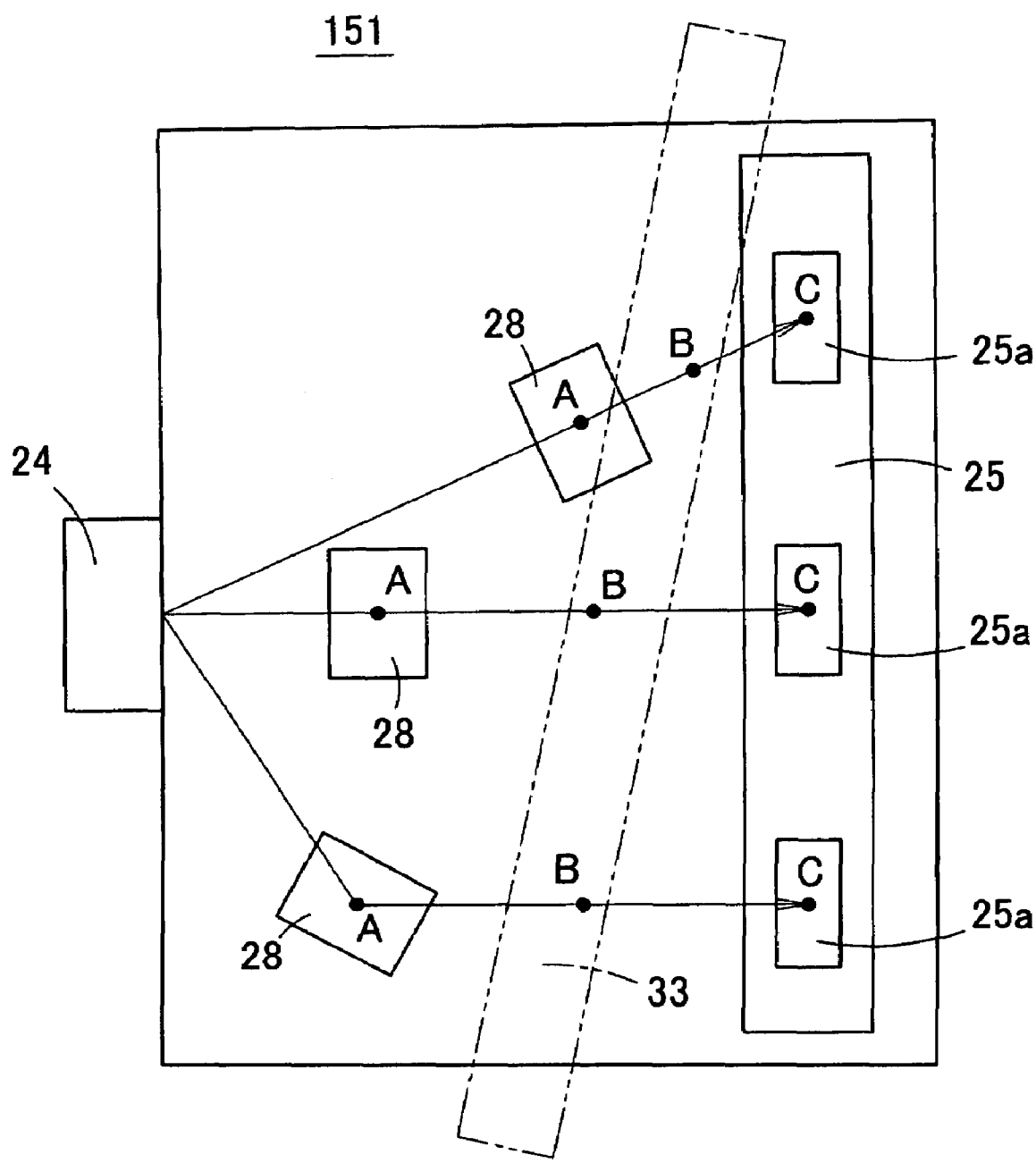
FIG. 43 shows a schematic view of a surface plasmon sensor according to an embodiment 11.

FIG. 43 shows a schematic view of a surface plasmon sensor 151 according to an embodiment 11 of the present invention. According to the surface plasmon sensor 151, a light emitting unit 24 and a reflection surface 28, etc are arranged such that inputted points C to a light receiving element 25 are aligned in a straight line at almost the same intervals. More specifically, the position and the inclined angle of the reflection surface 28 are adjusted and the direction (direction of the reflection surface 28) of the reflected light from the reflection surface 28 is adjusted so that the inputted points C of the light L to the light receiving element 25 are aligned and arranged at almost the same intervals. Thus, a one-dimensional photodiode array is provided at each inputted point C as a light receiving cell 25a (photodiode).

According to the surface plasmon sensor 151, an inexpensive one-dimensional photodiode array such as the photodiode array can be used in the light receiving element 25 instead of the CCD.

In addition, according to the surface plasmon sensor 141 shown in FIG. 14 also, since the inputted points C of the light L in the light receiving element 25 are aligned, the inexpensive one-dimensional light receiving element such as the photodiode array may be used in the light receiving element 25. In addition, according to the surface plasmon sensor 151 in FIG. 43, since the inputted and reflected points B of the light L in the metal layer 23 are not aligned, although the inputted and reflected points B may be connected by a curved narrow channel, the inputted and reflected points B may be connected by a linear channel 33 having a narrow width as much as possible and containing all of the inputted and reflected points B as shown by a phantom line in FIG. 43.

Embodiment 12

Figure 44:
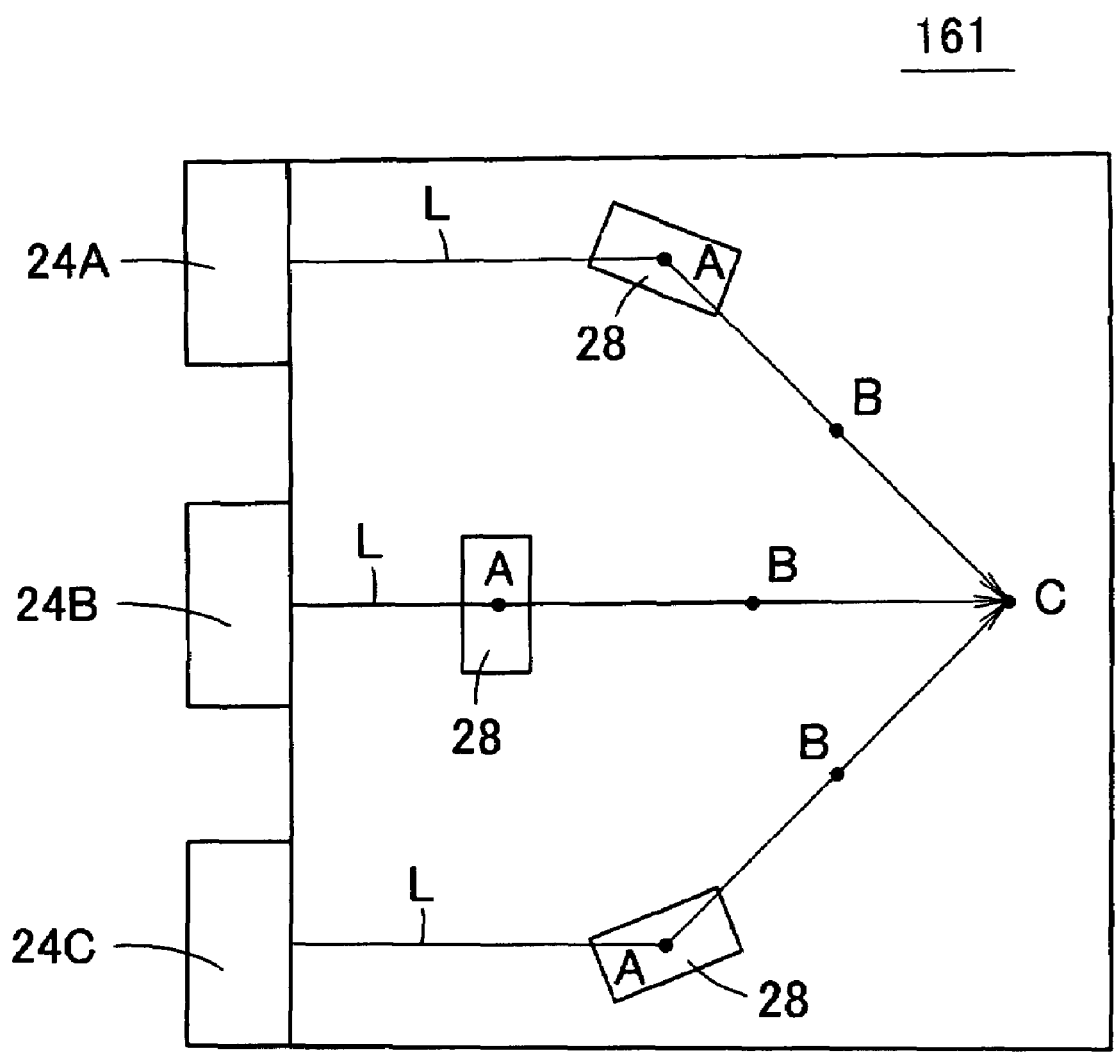
FIG. 44 shows a schematic view of a surface plasmon sensor according to an embodiment 12.

FIG. 44 shows a schematic view of a surface plasmon sensor 161 according to an embodiment 12 of the present invention. According to the surface plasmon sensor 161, a plurality of light emitting units 24A, 24B and 24C are provided on the end surface of a light guide reflection plate 22. Narrow lights L that are made parallel in a perpendicular plane and a horizontal plane with respect to the upper surface of the light guide reflection plate 22 are emitted from the light emitting unit 24. Thus, the position, inclined angle and direction of the reflection surface 28 are adjusted such that light L emitted from each light emitting unit 24, reflected by a reflection surface 28, and reflected by a metal layer 23 at each reflected angle may be inputted to one inputted point C. At the inputted point C, an inexpensive light receiving element 25 such as a photodiode is arranged.

In addition, in order to take different measurement by the light L of each optical path, the reflection surfaces 28 have different inclined angles from each other or different kinds of antibodies are fixed to the inputted and reflected points B of the light L in the metal layer 23.

Thus, according to the surface plasmon sensor 161, the light is emitted sequentially from the plurality of light emitting units such that 24A→24B →24C, for example and received by the same light receiving element 25. According to this embodiment, since one element (photodiode, for example) is used for the light receiving element 25, there are advantages that the cost of the light receiving element 25 can be inexpensive and since the same element is used, there is no measurement variation or an error in the light receiving element 25.

Embodiment 13

Figure 45:
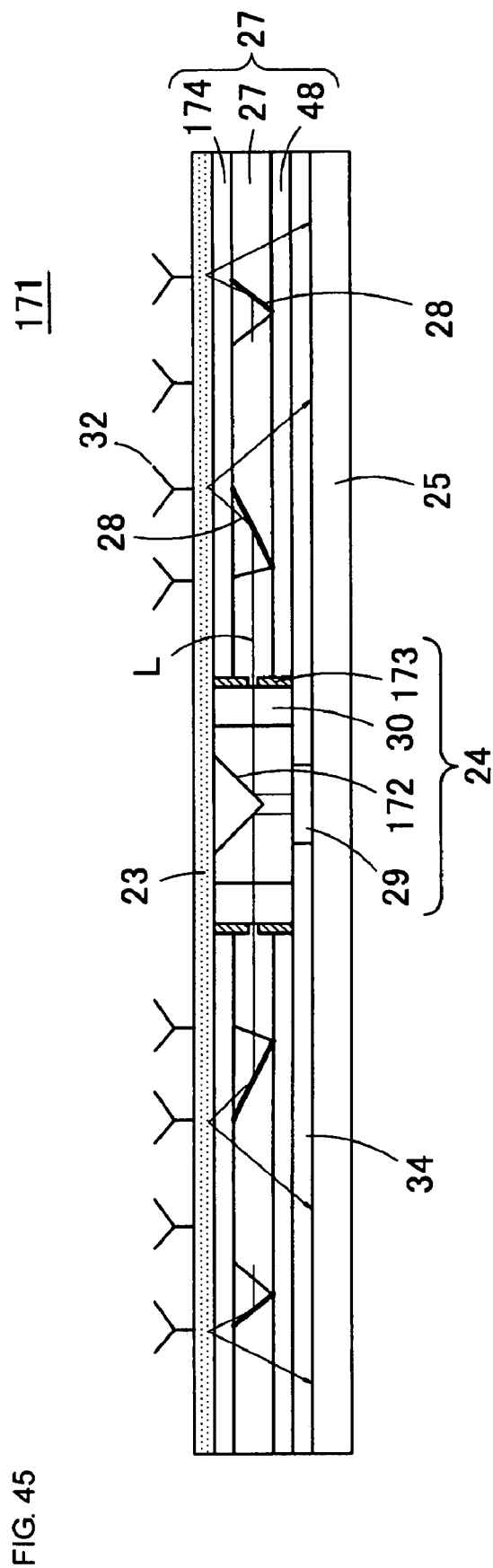
FIG. 45 shows a sectional view of the structure of a surface plasmon sensor according to an embodiment 13.
Figure 46:
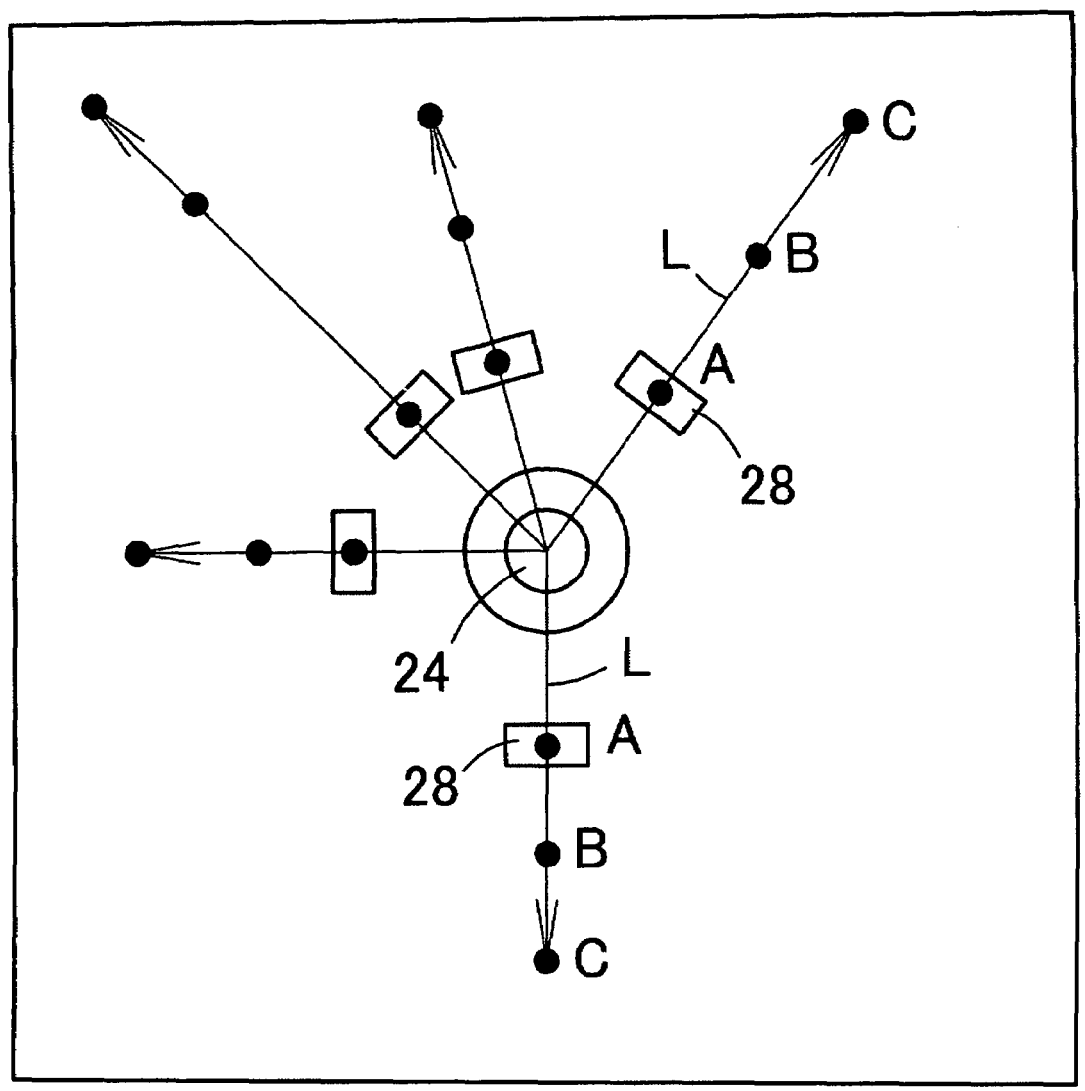
FIG. 46 shows a schematic view of the surface plasmon sensor according to the embodiment 13.

FIG. 45 shows a sectional view of the structure of a surface plasmon sensor 171 according to an embodiment 13 of the present invention, and FIG. 46 shows a schematic view of the surface plasmon sensor 171. A light emitting unit 24 of the surface plasmon sensor 171 includes a light source 29, a cone-shaped reflection plate 172, a polarizing element 30, and a light-absorbing light shielding plate 173 and arranged in the center of a light guide reflection plate 22. The light source 29 is arranged so as to emit light L (parallel light) upward, and the cone-shaped or polygonal cone-shaped reflection plate 172 having a reflection surface on its lower surface is arranged above the light source 29. The polarizing element 30 is formed in a cylindrical shape or a polygonal cylindrical shape so as to surround the cone-shaped reflection plate 172, and a slit or a small hole extending in the horizontal direction is opened in the light shielding plate 173 provided on the peripheral surface of the polarizing element 30. Therefore, when the light L is emitted upward from the light source 29, the light emitted from the light source 29 is reflected by the reflection surface of the cone-shaped reflection plate 172 and spreads to the peripheral direction and only straight polarized light in the horizontal direction or the perpendicular direction passes through the polarizing element 30. Then, when it passes through the slit or hole of the light shielding plate 173, collimated light that hardly spreads in the perpendicular direction is emitted to the whole direction or the direction in which the reflection surface 28 is arranged in the light guide reflection plate 22.

The light guide reflection plate 22 has a structure in which both upper and lower surfaces of a light guide plate 27 in which the plurality of reflection surfaces 28 are formed are sandwiched by an auxiliary substrate 174 (protection layer) and a transparent substrate 48, respectively. The light guide plate 27, the auxiliary substrate 174 and the transparent substrate 48 are all transparent and have the same refractive index. The plurality of reflection surfaces 28 are provided at appropriate positions at almost the same level as the horizontal plane in which the light L is emitted, in the light guide reflection plate 22. Here, it is to be noted that the reflection surfaces 28 are arranged so as not to overlap with each other in the emitting direction of the light L.

A metal layer 23 is formed of Au or Ag on the upper surface of the light guide reflection plate 22, an antibody 32 is fixed to a region to which the light L reflected by the reflection surface 28 is inputted.

In addition, the lower surface of the light guide reflection plate 22 is closely adhered to the upper surface of the light receiving element 25 with a matching oil 34 sandwiched between them. The light receiving element 25 includes a two-dimensional light receiving element such as a CCD.

Thus, in the surface plasmon sensor 171 also, the light emitted from the light emitting unit 24 and reflected by the reflection surface 28 is reflected by a reflection surface region to which the antibody 32 is fixed and inputted to the light receiving element 25. Thus, the intensity and variation of the light L is measured. In addition, in FIG. 46 also, reference character A designates an inputted and reflected point of the light L in the reflection surface 28, reference character B designates an inputted and reflected point of the light L in the metal layer 23, and reference character C designates an inputted point of the light L in the light receiving element 25.

According to the above structure, since the reflection surfaces 28, etc can be radially arranged centering around the light emitting unit 24, there is less wasted region in the light guide reflection plate 22, many reflection surface regions can be set for one light emitting unit 24, and more reactions between the antibody and antigen can be detected.

Figure 47:
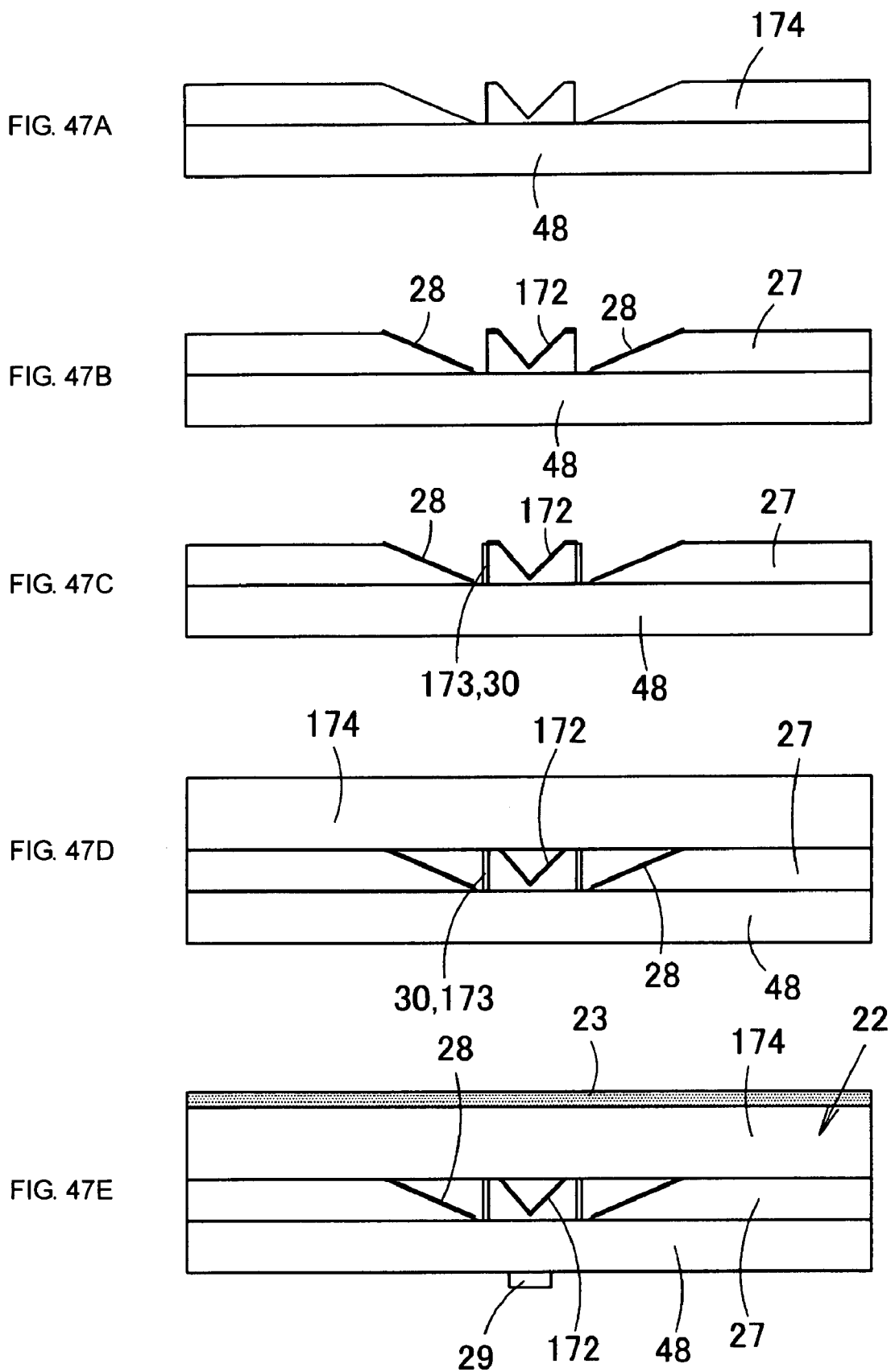
FIGS. 47A to 47E show process charts showing one example of manufacturing steps of the surface plasmon sensor in the embodiment 13.

A manufacturing method of the surface plasmon sensor 171 will be described hereinafter. FIGS. 47A to 47E show process charts showing one example of the manufacturing steps of the surface plasmon sensor 171. First, a UV cured resin is supplied to the transparent substrate 48, and this is pressed by a stamper (not shown) and cured. Thus, as shown in FIG. 47A, the light guide plate 27 having a pattern surface for forming the cone-shaped reflection plate 172 and the reflection surface 28 is formed.

Then, as shown in FIG. 47B, a metal layer film is deposited on the pattern surface for forming the cone-shaped reflection plate 172 and the reflection surface 28 on the surface of the light guide plate 27 to form the cone-shaped reflection plate 172 and the reflection surface 28.

Then, as shown in FIG. 47C, the cylindrical or polygonal polarizing element 30 and the light shielding plate 173 are provided in the periphery of the cone-shaped reflection plate 172 and then as shown in FIG. 47D, the auxiliary substrate 174 is laminated on the light guide plate 27. In addition, the space between the cone-shaped reflection plate 172 and the auxiliary substrate 174 and the space between the reflection surface 28 and the auxiliary substrate 174 may be as it is or may be filled with a transparent resin having the same refractive index as those of the light guide plate 27 and the auxiliary substrate 174 to seal the cone-shaped reflection plate 172 and the reflection surface 28.

Then, as shown in FIG. 47E, the metal layer 23 is formed on the upper surface of the auxiliary substrate 174 and the light source 29 is mounted on the center of the lower surface of the transparent substrate 48. The product manufactured as described above and shown in FIG. 47E have the matching oil 34 thinly applied to its lower surface and becomes a replacement component of the surface plasmon sensor 171.

Furthermore, the lower surface of the replacement component is set on the light receiving element 25 with the matching oil 34 sandwiched between them, whereby the surface plasmon sensor 171 is manufactured. According to the above manufacturing method, since the number of steps is reduced and an alignment operation of the reflection surface 28, etc is not needed, the surface plasmon sensor 171 can be manufactured with high accuracy.

Figure 48:
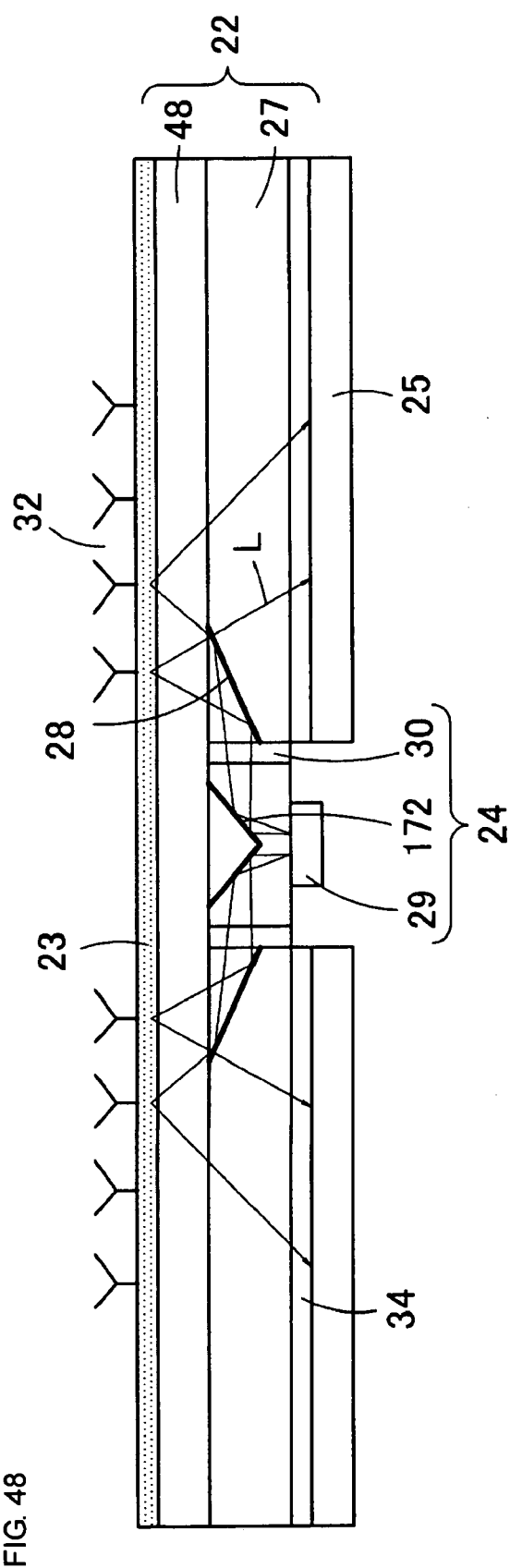
FIG. 48 shows a sectional view of a surface plasmon sensor according to a variation of the embodiment 13.

FIG. 48 shows a sectional view of a variation of the disk-shaped surface plasmon sensor 171 in the embodiment 13. According to this variation, the light shielding plate 173 is not provided in a light emitting unit 24. Therefore, light L emitted from the light emitting unit 24 spreads in a plane perpendicular to the upper surface of a light guide reflection plate 22 and the light L reflected by a reflection surface 28 enters the reflection surface region of a metal layer 23 while scattering, and the light L reflected there is received by a light receiving cell 25a in accordance with the reflected angle at the reflection surface region. In addition, a light guide plate 27 having the reflection surface 28 is provided on the lower surface of a transparent substrate 48 in the light guide reflection plate 22 in this embodiment.

According to this variation, since the divergent light from the light emitting unit 24 is used, the light L having different reflected angle can be measured at one reflection surface region in the metal layer 23, so that the number of surfaces of the reflection surface region can be reduced.

Figure 49A:
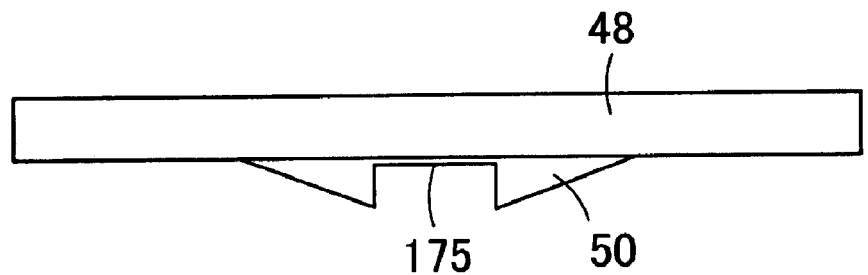
FIGS. 49A to 49D show process charts to explain manufacturing steps of the surface plasmon sensor according to the variation of the embodiment 13.

FIGS. 49A to 49D show process charts that explain the steps of manufacturing the surface plasmon sensor according to the one or more embodiments of the present invention. As shown in FIG. 49A, a projection 50 is formed to form the reflection surface 28 on the lower surface of the transparent substrate 48 by the stamper and a recession 175 is formed to mount the light emitting unit 24 in the center of the lower surface of the transparent substrate 48.

Figure 49B:
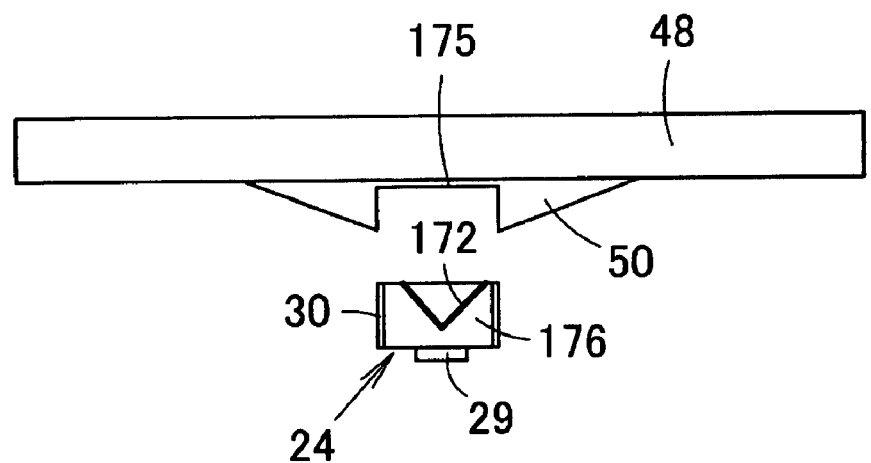

Then, as shown in FIG. 49B, the light emitting unit 24 is fit in the recession 175. The light emitting unit 24 is to be manufactured previously at separate steps by providing a cone-shaped or polygonal cone-shaped reflection plate 172 on the upper surface of a column-shaped or polygonal column-shaped transparent resin block 176, mounting a light source 29 on the lower surface of the transparent resin block 176, and providing a polarizing element 30 on the peripheral surface of the transparent resin block 176.

Figure 49C:
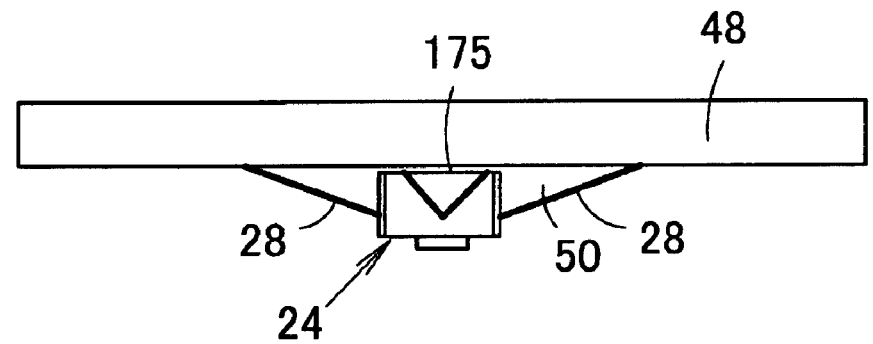

Then, as shown in FIG. 49C, the reflection surface 28 is formed by forming a metal film by deposition, etc on the inclined surface of the projection 50.

Figure 49D:
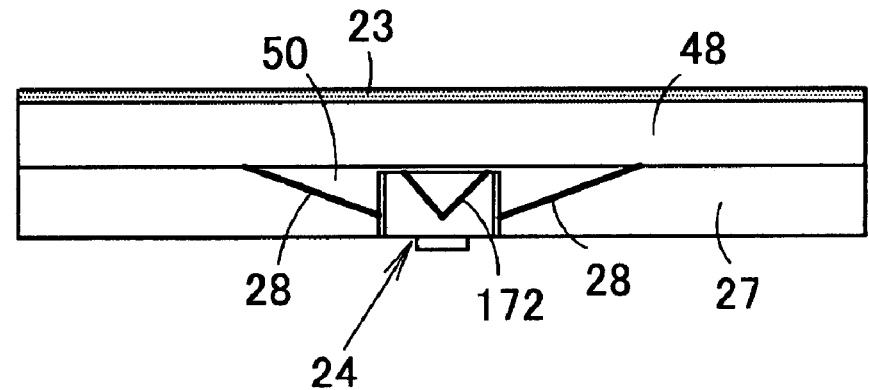

Then, as shown in FIG. 49D, the metal layer 23 including metals such as Au or Ag is formed on the upper surface of the transparent substrate 48, and the light guide plate 27 is formed on the lower surface of the transparent substrate 48 with a transparent resin and the reflection surface 28 is sealed between the light guide plate 27 and the projection 50.

Embodiment 14

Figure 50:
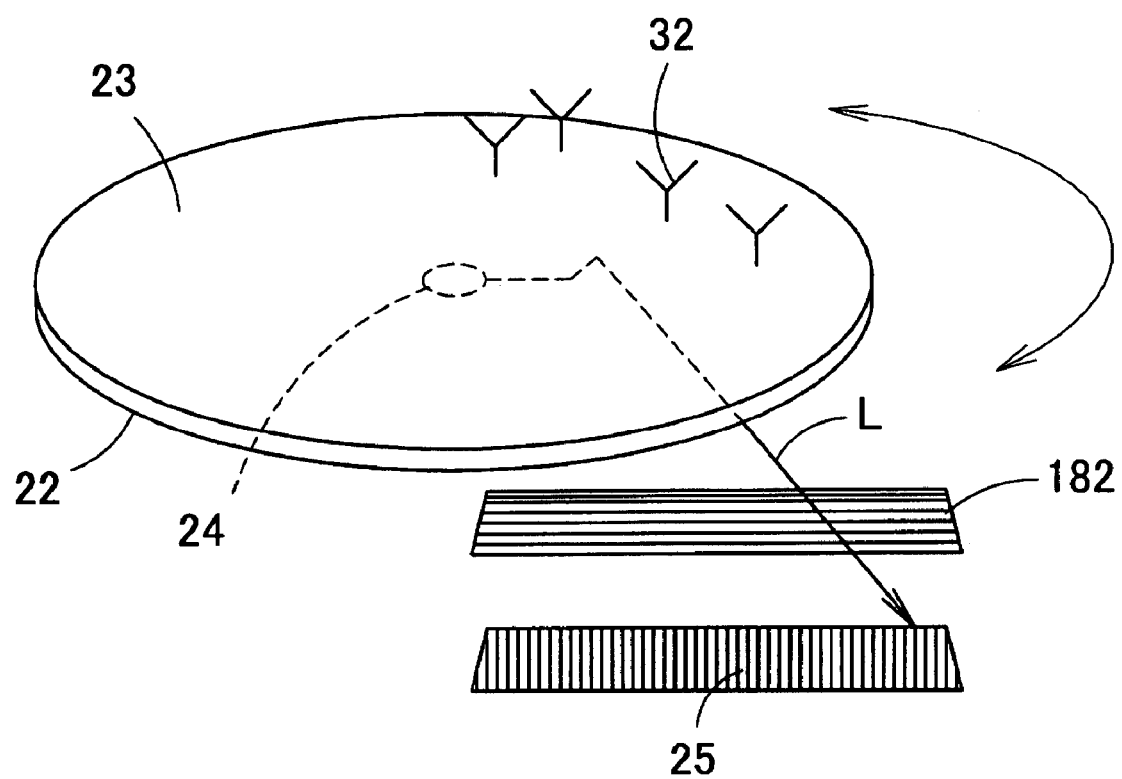
FIG. 50 shows a schematic perspective view of a surface plasmon sensor according to an embodiment 14.

FIG. 50 shows a schematic perspective view of a surface plasmon sensor 181 according to an embodiment 14 of the present invention. According to the surface plasmon sensor 181, as described in the embodiment 13, a light guide reflection plate 22 on which a metal layer 23 is formed is rotated by a rotation driving device (not shown) using for example, a motor, etc. A light receiving element 25 is a one-dimensional light receiving element such as a photodiode array, etc, and it is arranged on the lower surface of the light guide reflection plate 22 in a resting state along its radius direction. A light emitting unit 24 used in this case emits radiating light in the plane perpendicular to the metal layer 23, while it emits hardly radiating light in the plane parallel to the metal layer 23.

Thus, according to the surface plasmon sensor 181, measurement is taken by rotating the light guide reflection plate 22 on which an antibody 32 is fixed to the metal layer 23. Although only the light L entering from just above the light receiving element 25 is received by the light receiving element 25, since the light L for measurement is emitted from the whole lower surface of the light guide reflection plate 22, the measurement is taken on the whole surface of the metal layer 23 after the light guide reflection plate 22 is rotated one time.

In addition, a polarizing element 182 is arranged on the light receiving element 25 such that only the light L (polarized light) entering from just above the light receiving element 25 is transmitted. Since polarized direction of the light L entering from the direction other than that from just above the light receiving element 25 does not coincide with that of the polarizing element 182, it is not likely to pass through the polarizing element 182 and not likely to be received by the light receiving element 25, so that the measurement precision of the polarizing element 182 is improved.

According to this embodiment, since it is not necessary to provide the light receiving element 25 so as to correspond to the whole surface of the metal layer 23, the light receiving element 25 can be inexpensive. Furthermore, since the same light receiving element 25 and polarizing element 182 can be used for measurements in the various directions, the measurement is prevented from varying.

Figure 51:
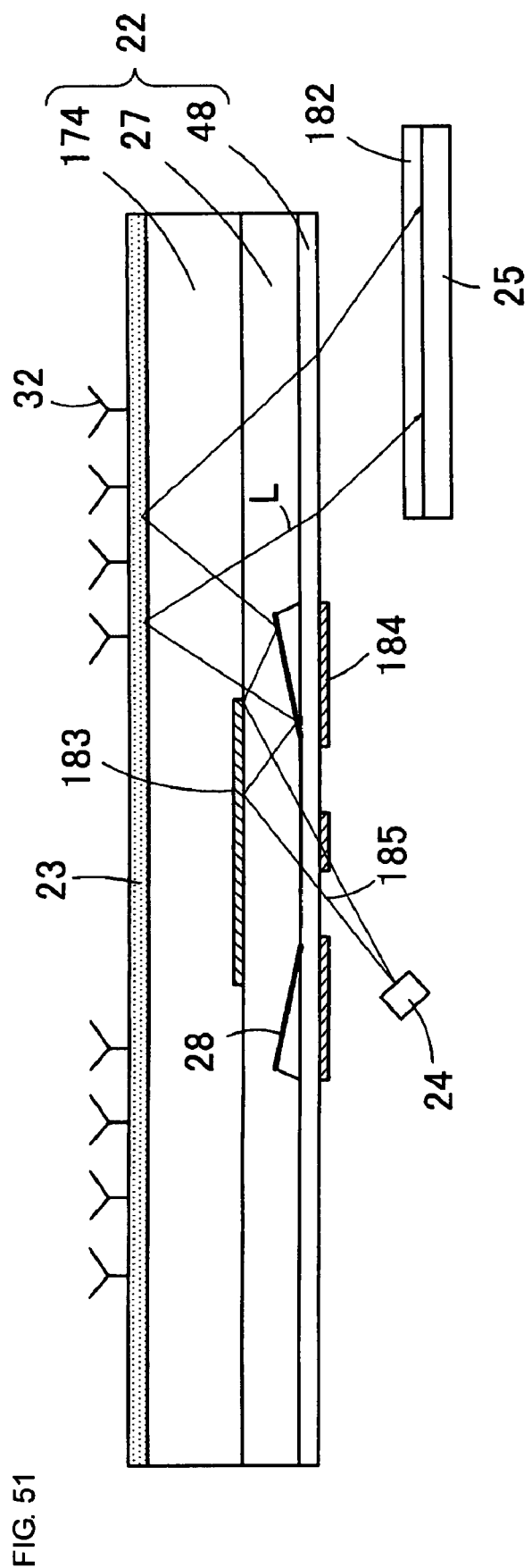
FIG. 51 shows a sectional view of a variation of the embodiment 14.

FIG. 51 shows a sectional view of a variation of the embodiment 14. According to this variation, a light shielding plate 184 formed of a light-absorbing material is provided in the center of the lower surface of a light guide reflection plate 22, and a radiating slit 185 is formed in the light shielding plate 184. In addition, a mirror 183 is provided in the center of the light guide reflection plate 22. Thus, light L is emitted diagonally upward from the light emitting unit 24 to the rotating light guide reflection plate 22.

Thus, when the light L is emitted diagonally upward from the light emitting unit 24, the light L passes through the slit 185 and inputted to the light guide reflection plate 22 and it is reflected by the mirror 183 and inputted to the reflection surface 28. Then, similar to the case of the embodiment 14, the light L reflected by the reflection surface 28 is inputted to the reflection surface region of the metal layer 23, and the light L reflected by the reflection surface region passes through the polarizing element 182 and received by the light receiving element 25. Then, while the light guide reflection plate 22 on which the metal layer 23 is formed is rotated, the measurement is sequentially performed in the reflection surface regions.

According to the variation, since the light emitted from the light emitting unit 24 does not spread in the whole direction, but it is emitted only forward like in the embodiment 14, the light L having higher intensity in the center of the light emitting unit 24 can be effectively used. In addition, as shown in FIG. 51, when the light L emitted from the light emitting unit 24 is diverged a little, measurements at different reflected angles in the reflection surface region can be implemented by the light L reflected by the one reflection surface 28 at the same time. In addition, to prevent the light L from being totally reflected by the lower surface of the transparent substrate 48, a matching oil having a refractive index smaller than the transparent substrate 48 is applied to the lower surface of the transparent substrate 48.

Embodiment 15

Figure 52:
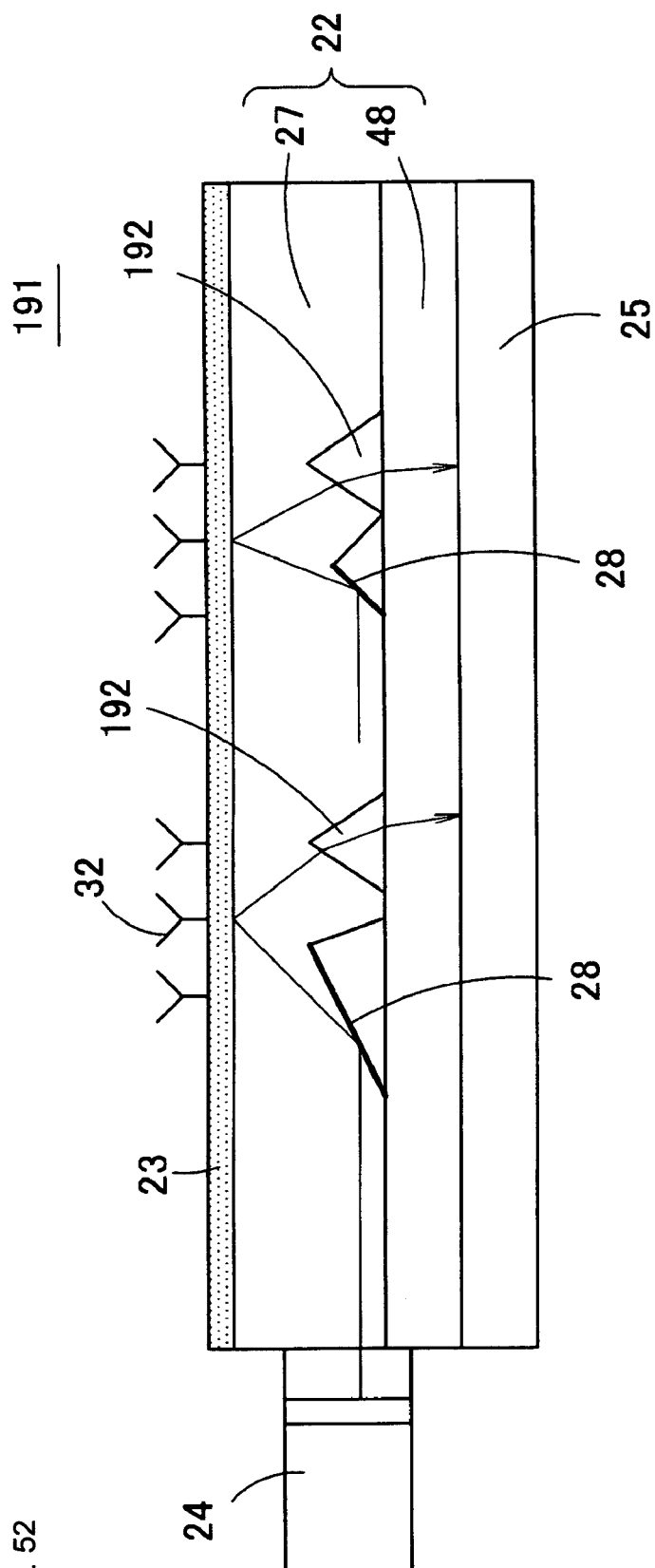
FIG. 52 shows a sectional view of a surface plasmon sensor according to an embodiment 15.
Figure 53A:
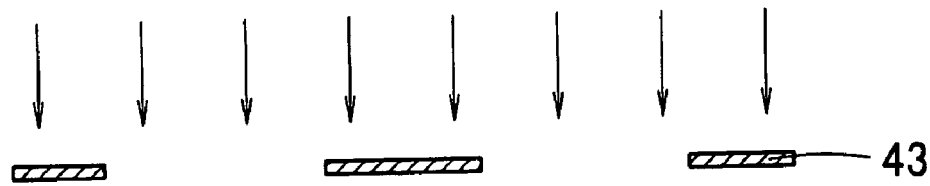
FIGS. 53A to 53D show process charts showing manufacturing steps of a stamper according to the embodiment 15.
Figure 53B:
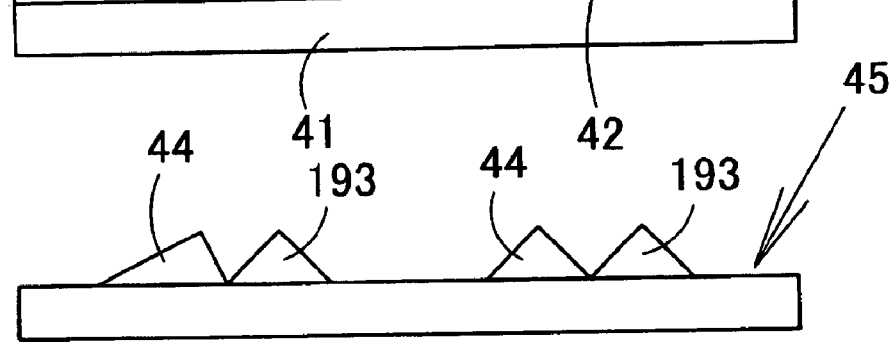
Figure 53C:
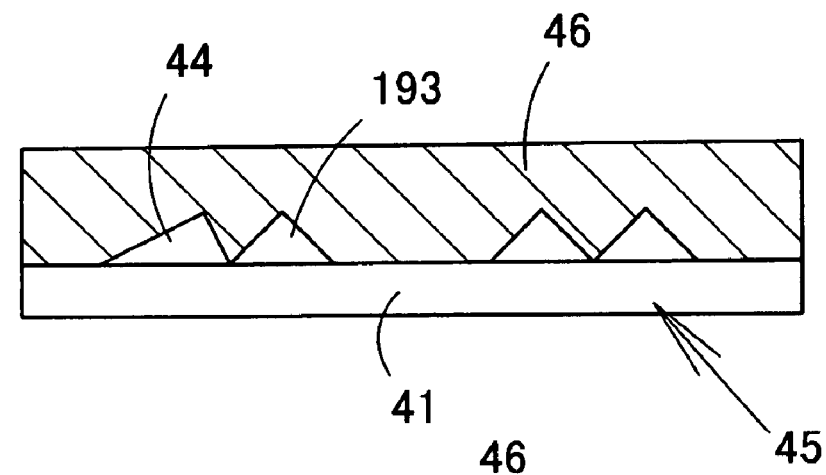
Figure 53D:
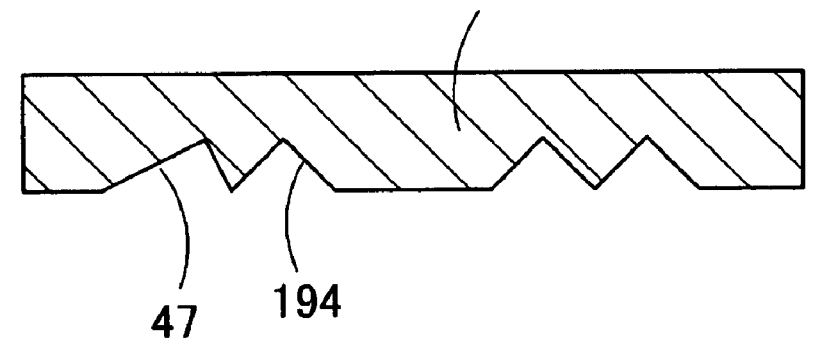

FIG. 52 shows a sectional view of a surface plasmon sensor 191 according to an embodiment 15 of the present invention. According to the surface plasmon sensor 191, a deflection part 192 in the shape of a triangular prism is provided at the back of a reflection surface 28. The deflection part 192 is formed of a transparent resin having a refractive index smaller than that of a light guide plate 27 and a transparent substrate 48. Each deflection part 192 is arranged such that light L reflected by the reflection surface 28 positioned anterior to it is reflected by a metal layer 23 and then passes through the deflection part 192, and it is formed such that the angle of the light L after passed through the deflection part 192, formed with the perpendicular line on the upper surface of the light receiving element 25 is smaller than that of the light before pass through the deflection part 192. A light emitting unit 24 emits the light collimated in the vertical direction only in a fan-like form in a horizontal plane.

Therefore, according to the surface plasmon sensor 191 of the embodiment 15, since the incident angle of the light L inputting to the light receiving element 25 can be reduced by means of the deflection part 192, even when there is no matching oil between a light guide reflection plate 22 and a light receiving element 25, the light L is prevented from being totally reflected by the lower surface of the light guide reflection plate 22. As a result, according to this embodiment, it is not necessary to apply the matching oil that is hard to handle, to the lower surface of the light guide reflection plate 22.

FIGS. 53A to 53D and FIGS. 54A to 54D show process charts showing one example of the manufacturing steps of the light guide reflection plate 22 according to the embodiment 15. Although this manufacturing steps are almost the same as those described with reference to FIGS. 9 and 10, according to this embodiment, since a model 193 of the deflection part 192 is formed as well as the model 44 of the projection 50 in step in FIG. 53B, there is formed a recession 194 for forming the deflection part 192 as well as a recession 47 for forming the projection in the lower surface of a stamper 46 in FIG. 53D.

Figure 54A:
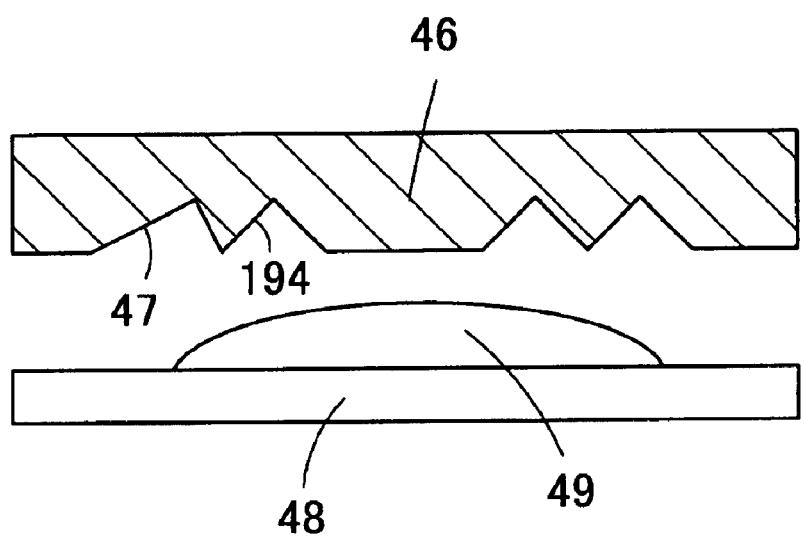
FIGS. 54A to 54D show process charts showing manufacturing steps of a light guide reflection plate in the embodiment 15 using the stamper manufacture in FIG. 53.
Figure 54B:
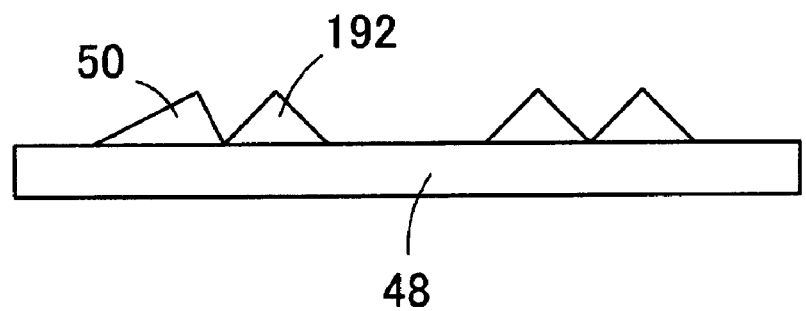
Figure 54C:
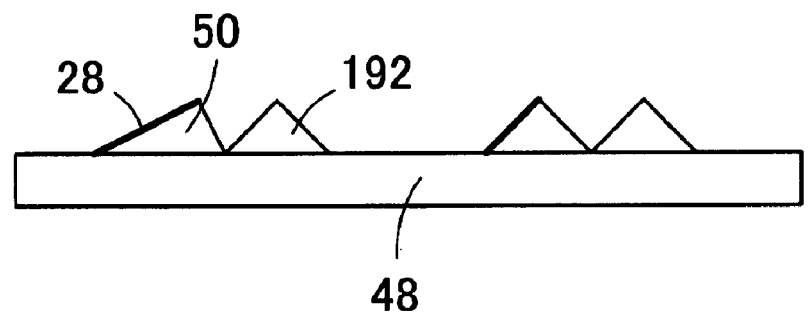
Figure 54D:
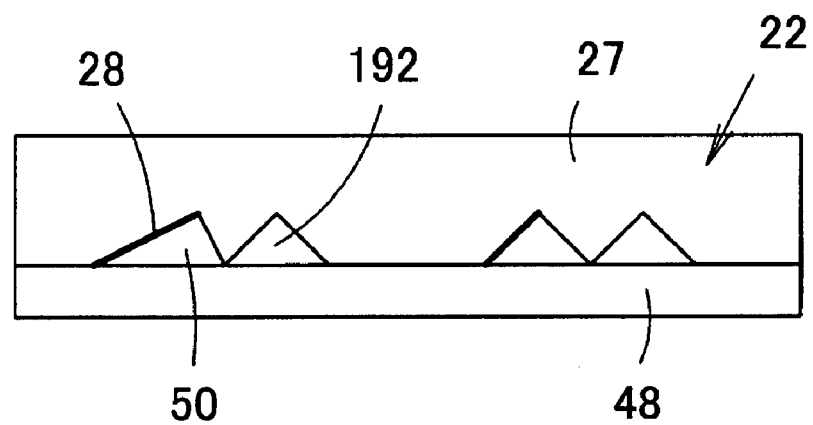

In addition, since a UV cured resin 49 having a refractive index smaller than those of the transparent substrate 48 and the light guide plate 27 is used in FIG. 54A, the deflection part 192 having the refractive index smaller than the light guide plate 27 is formed in the light guide reflection plate 22 at the steps in FIGS. 54B to 54D.

Figure 55:
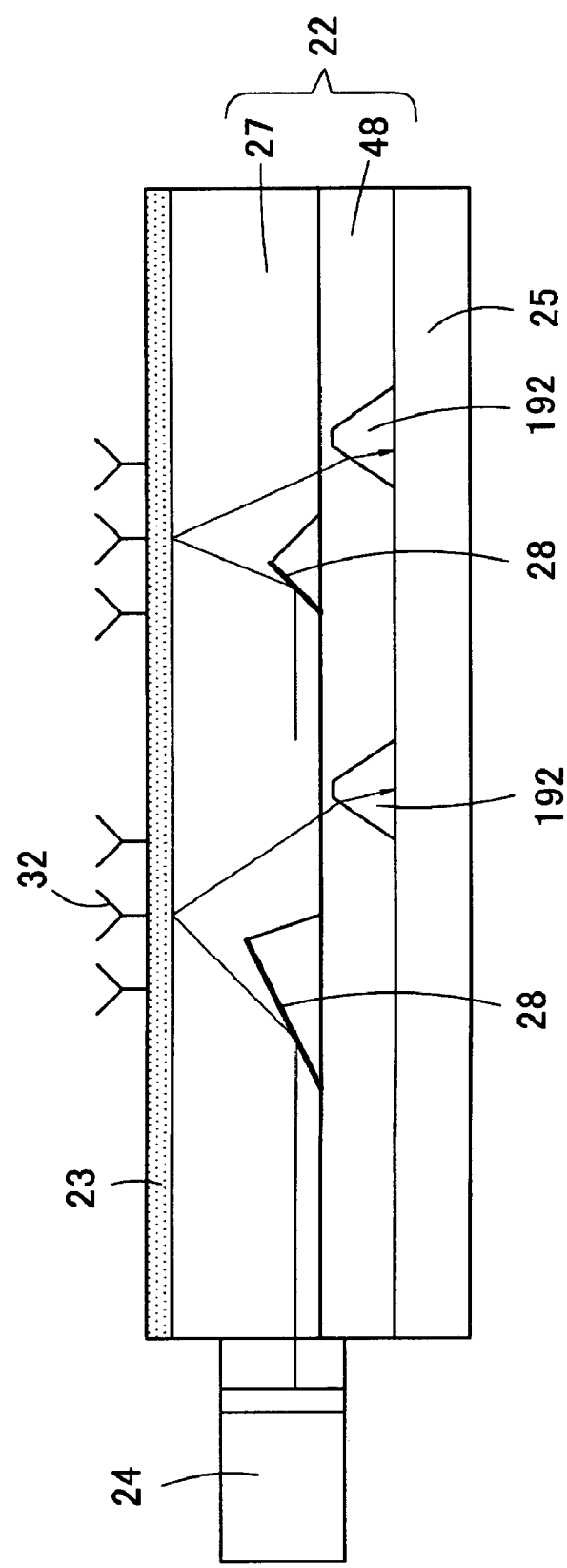
FIG. 55 shows a sectional view of a variation of the embodiment 15.

FIG. 55 shows a sectional view of a variation of the embodiment 15. According to this variation, a deflection part 192 is formed by a recession (air layer) having a trapezoidal section in the lower surface of a transparent substrate 48. A light emitting unit 24 emits light collimated in the vertical direction only in a fan-like form in a horizontal plane.

Figure 56:
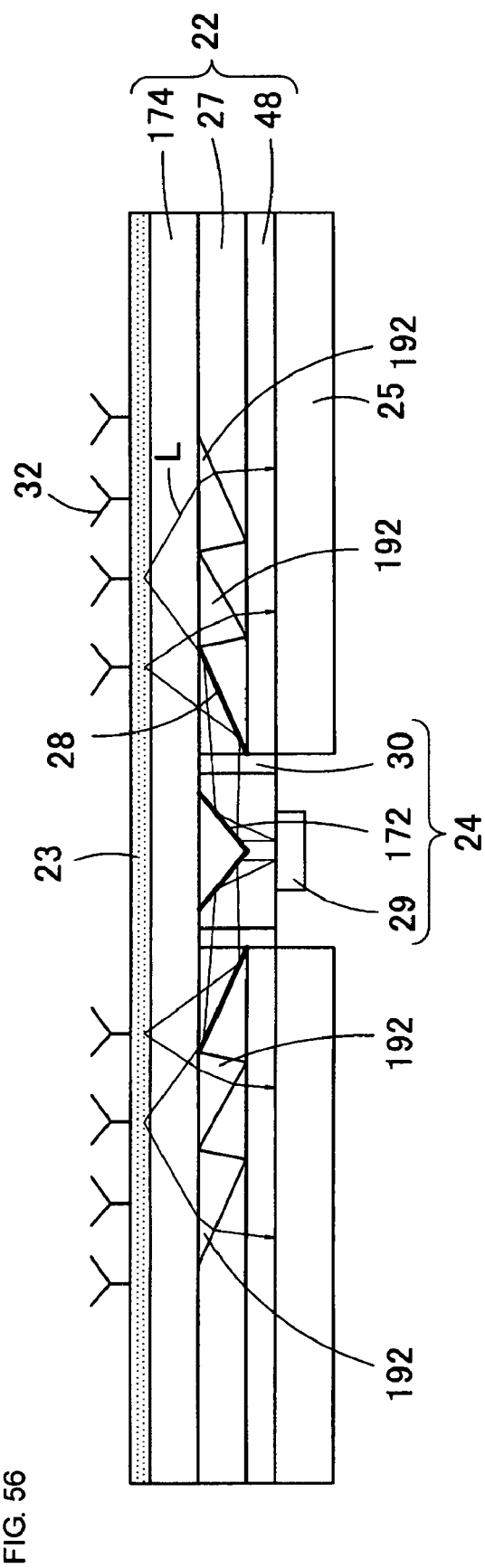
FIG. 56 shows a sectional view of another variation of the embodiment 15.
Figure 57A:
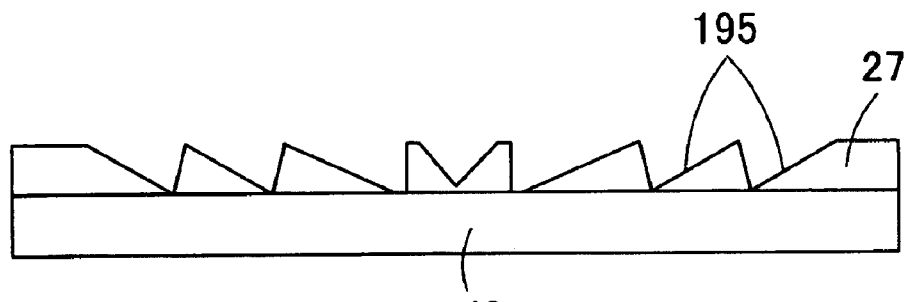
FIGS. 57A to 57E show process charts showing manufacturing steps of the surface plasmon sensor according to another variation of the embodiment 15.
Figure 57B:
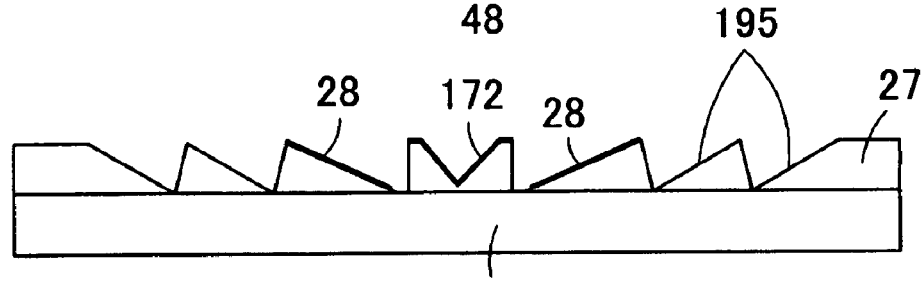
Figure 57C:
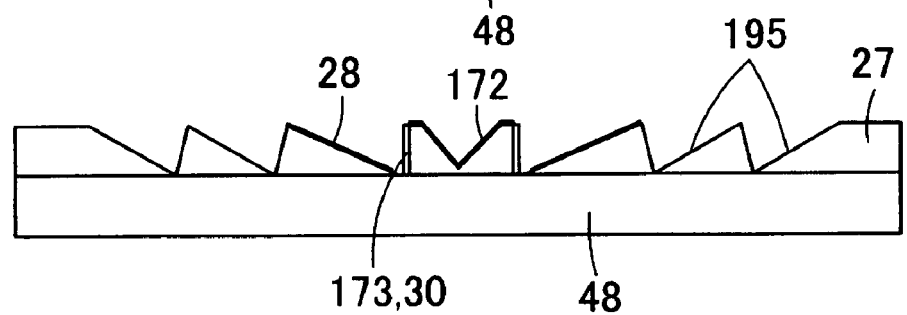
Figure 57D:
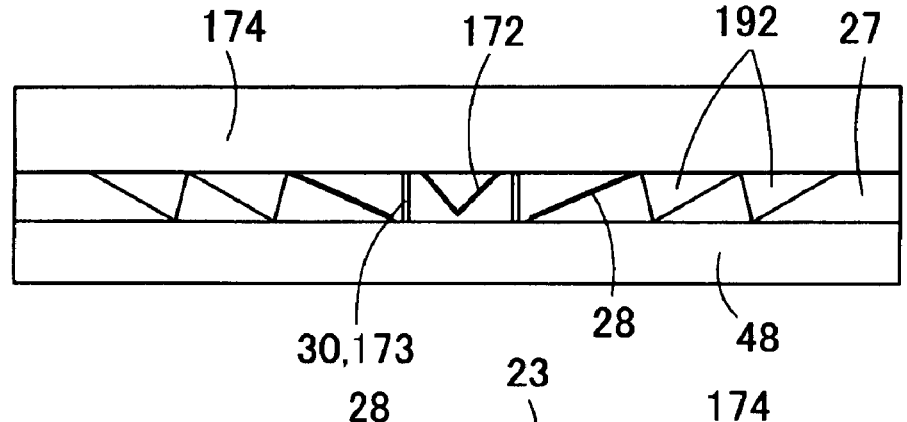
Figure 57E:
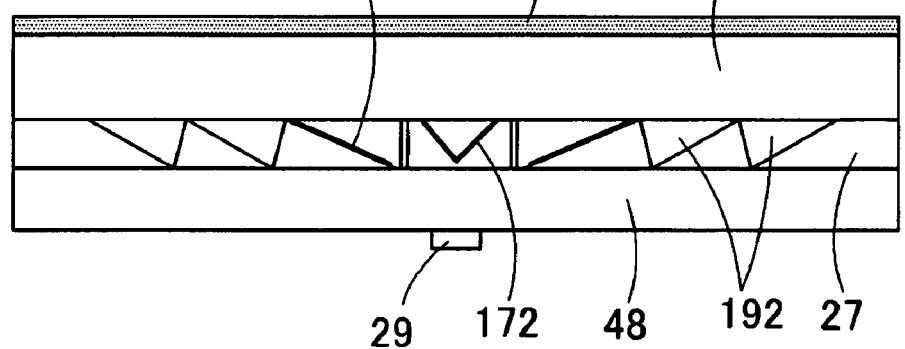
Figure 58A:
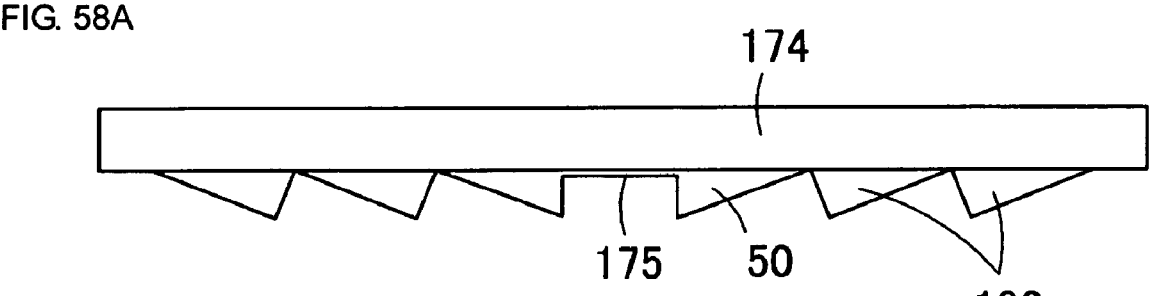
FIGS. 58A to 58D show process charts showing another manufacturing steps of the surface plasmon sensor according to another variation of the embodiment 15.
Figure 58B:
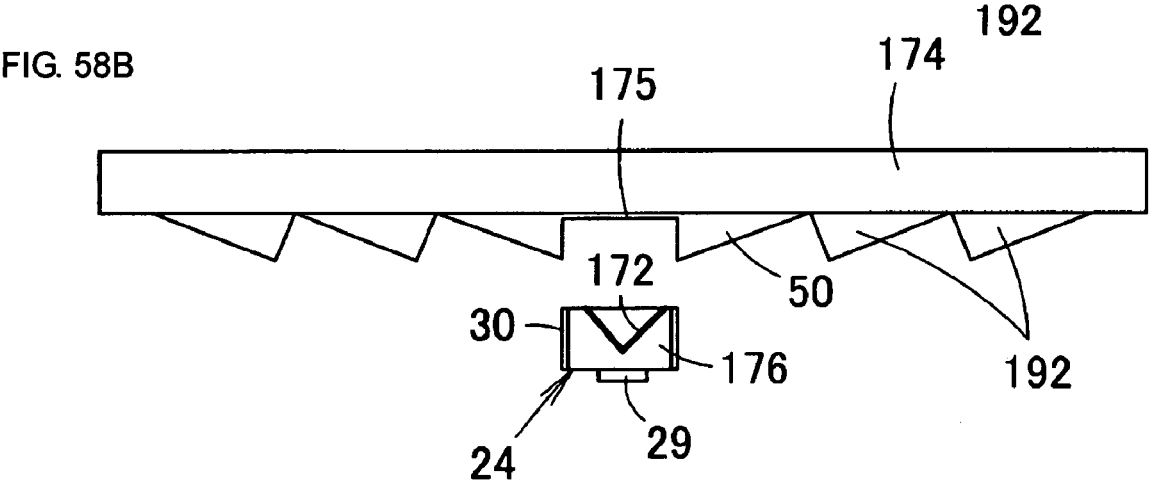
Figure 58C:
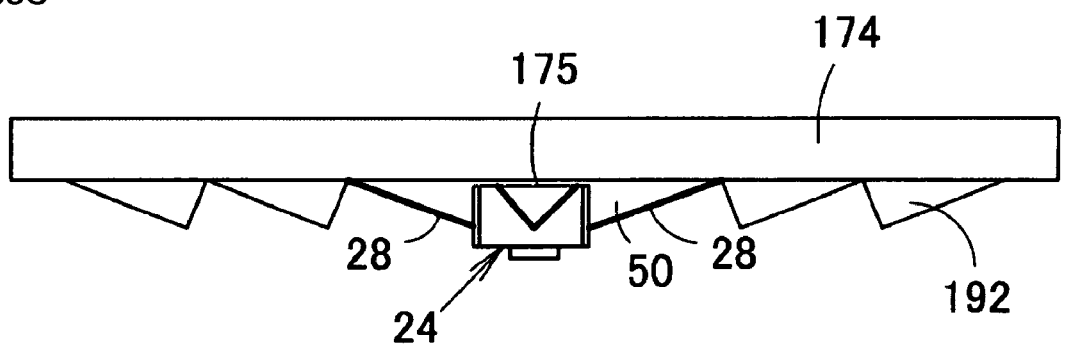
Figure 58D:
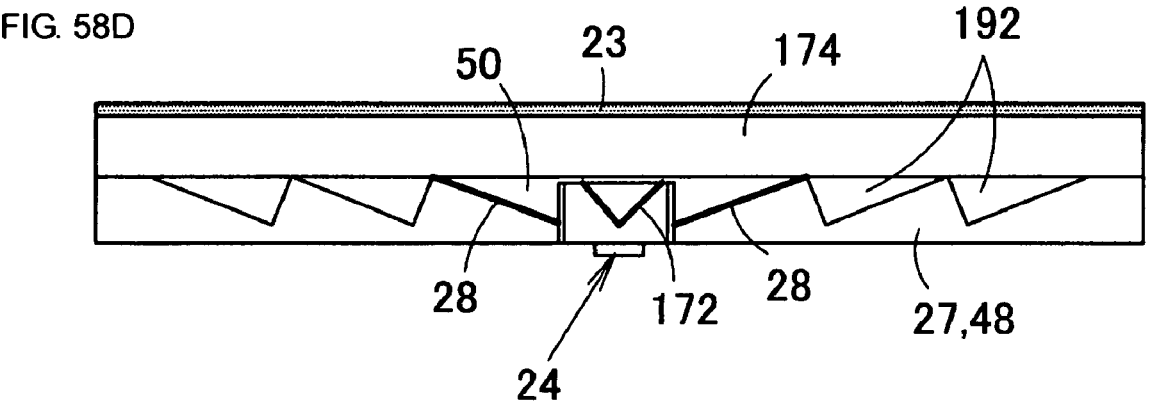

FIG. 56 shows a sectional view of another variation of the embodiment 15. According to this variation, a matching oil is not needed because a deflection part 192 is provided in the surface plasmon sensor shown in FIG. 48. However, according to this variation, the deflection part 192 is formed of a transparent resin having a refractive index higher than that of a light guide plate 27. A light emitting unit 24 emits light spreading in the vertical direction to whole directions in a horizontal plane.

In addition, when the light emitted from the light emitting unit 24 is diverged like in this variation or the embodiment shown in FIG. 48, the light reflected by the metal layer 23 largely spreads. In this case, when the directions of the whole lights are to be bent by one deflection part 192 having the triangular prism section, the deflection part 192 becomes thick, which increases the thickness of the surface plasmon sensor. Therefore, according to this variation, the deflection area 192 is prevented from becoming thick by arranging the plurality of deflection parts 192 having the triangular prism sections.

Furthermore, FIGS. 57A to 57E show process charts showing the manufacturing steps of the surface plasmon sensor according to the variation shown in FIG. 56. Although the manufacturing steps are almost the same as those shown in FIG. 47, when the light guide plate 27 is formed on the upper surface of a transparent substrate 48 in the step in FIG. 57A, a recession 195 for forming the deflection part 192 in the light guide plate 27 is formed and the deflection part 192 is formed by filling the recession 195 with a transparent resin having a refractive index higher than those of the transparent substrate 48 and the light guide plate 27 at the step in FIG. 57D.

FIGS. 58A to 58D show process charts showing other steps for manufacturing the surface plasmon sensor according to the variation shown in FIG. 56. Although the manufacturing steps are almost the same as those shown in FIG. 49, the deflection part 192 is formed, together with the projection 50, on the lower surface of an auxiliary substrate 174 by a transparent resin having a refractive index higher than those of the transparent substrate 48, the light guide plate 27 and the auxiliary substrate 174 at the step in FIG. 58A. In addition, the light guide plate 27 and the transparent substrate 48 are formed at the same step.

Figure 59:
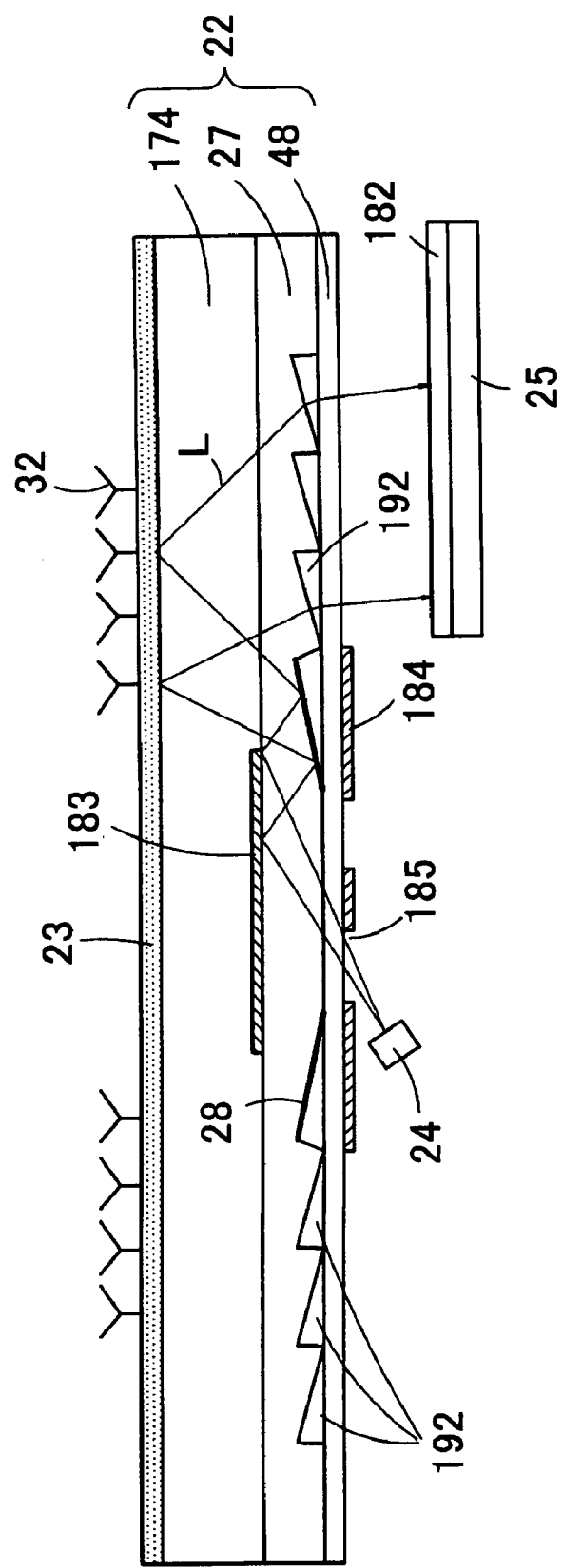
FIG. 59 shows a sectional view of still another variation of the embodiment 15.

FIG. 59 shows a sectional view of still another variation of the embodiment 15. According to this variation, a plurality of deflection parts 192 having the shape of triangular prism are provided with a transparent resin or cavities having a refractive index smaller than the light guide plate 27 in the surface plasmon sensor shown in FIG. 51. Although the deflection part 192 is provided in the whole region through which the light passes in this variation also, a light guide reflection plate 22 is prevented from becoming thick by dividing the deflection part 192. While a light emitting unit 24 emits radiating light in the plane perpendicular to a metal layer 23, it emits hardly spreading light in the plane parallel to the metal layer 23.

Embodiment 16

Figure 60:
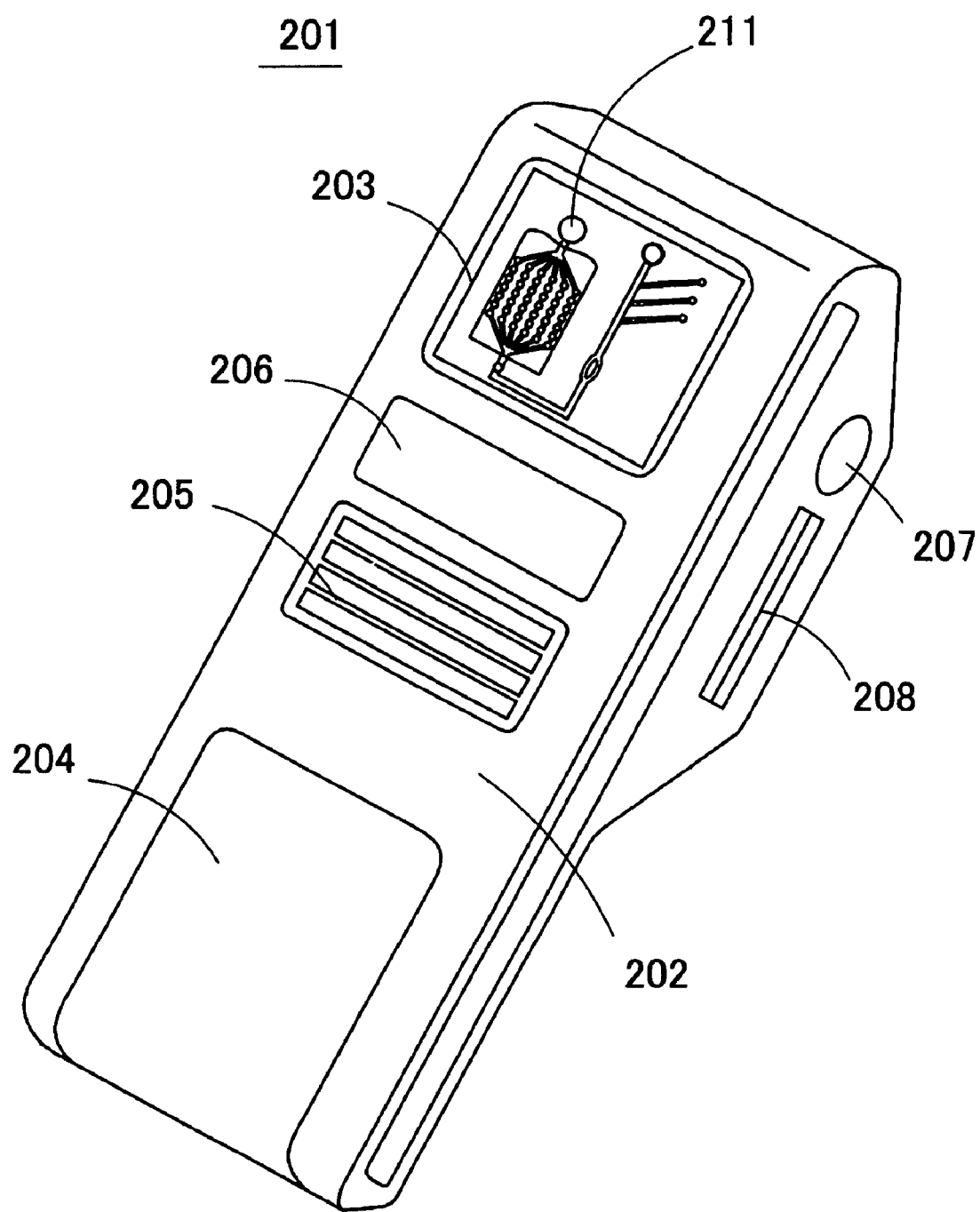
FIG. 60 shows a perspective view of a flow-type analyzer according to an embodiment 16.

FIG. 60 shows an outside perspective view of a flow-type analyzer 201 according to one or more embodiments of the present invention. The flow-type analyzer 201 incorporates a surface plasmon sensor 203 according to one or more embodiments of the present invention at the upper part of a casing 202 and includes a power supply 204 such as a dry battery at the lower part of the casing 202, and has an operation switch 205 for starting an analyzing process, above the power supply 204. In addition, a liquid crystal display 206 for displaying the guide of an operation method, the progress of the analyzing process, analyzed result, etc is provided above the operation switch 205. Furthermore, this flow-type analyzer 201 incorporates a small printer and when a printing switch 207 on the side is pressed, the analyzed result, etc are printed out from a print result outlet 208 provided beside the switch.

Figure 61:
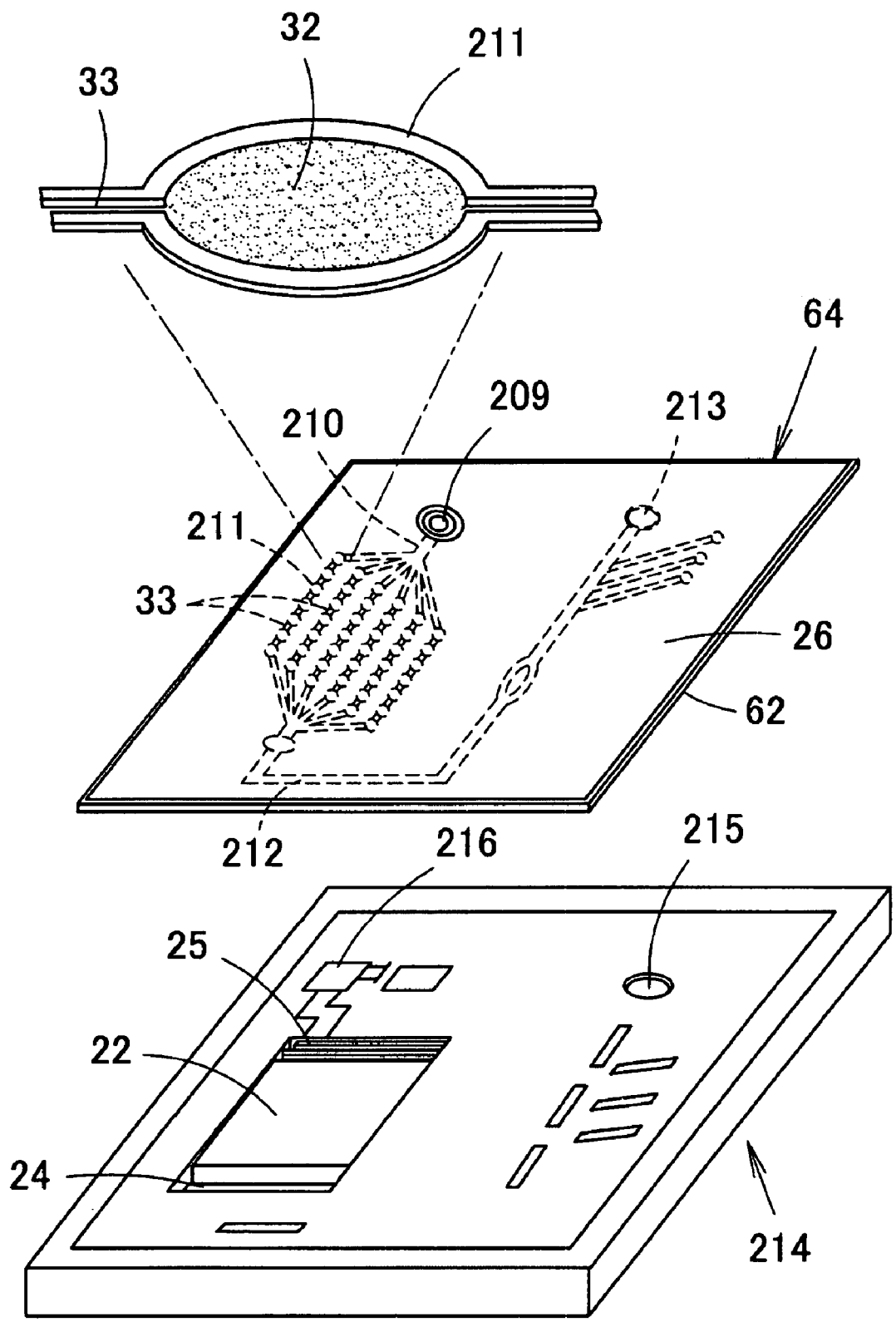
FIG. 61 shows an exploded perspective view of the structure of a surface plasmon sensor incorporated in the above flow-type analyzer shown in FIG. 60.

FIG. 61 shows an exploded perspective view of the structure of the surface plasmon sensor 203 incorporated in the flow-type analyzer 201. According to the surface plasmon sensor 203, a replacement component 64 can be detachably set on a sensor body 214 and only the sensor body 214 is fixed to the casing 202.

The replacement component 64 has a structure in which a channel cover 26 is set on an auxiliary substrate 62 on which a metal layer 23 is formed. A sample solution supply port 209 for supplying a sample solution is provided in the channel cover 26, and a sample solution discharge port 213 for discharging the sample solution after inspected is provided in the auxiliary substrate 62. A supply tube 210 (sample solution supply path), channels 33, a discharge tube 212 (sample solution supply path) are formed between the auxiliary substrate 62 and the channel cover 26, and one end of the supply tube 210 is communicated with the sample solution supply port 209. The other end of the supply tube 210 is connected to the channels 33, and the other ends of the channels 33 are connected to the discharge tube 212, and the other end of the discharge tube 212 is connected to the sample solution discharge port 213. An antibody holder 211 for positioning and holding an antibody 32 is arranged at a position through which the channel 33 passes, and the channel 33 is communicated with the antibody holder 211. Thus, after the sample solution inputted from the upstream channel 33 has spread in the antibody holder 211, it is discharged from the downstream channel 33.

A light emitting unit 24, a light guide reflection plate 22 and a light receiving element 25 are provided in the sensor body 214, and a controller 216 for controlling the flow-type analyzer 201 is also provided. Furthermore, the sensor body 214 is provided with a pump 215 for pumping out the sample solution to the sample solution supply path and the channels 33, and a collecting tank 217 (refer to FIG. 62) for collecting the sample solution after inspected. The replacement component 64 is set on the sensor body 214 such that the region on which the channel 33 and the antibody holder 211 are provided is overlapped on the light guide reflection plate 22 with a thin matching oil layer sandwiched between them and the sample solution discharge port 213 is connected to the pump 215.

Figure 62:
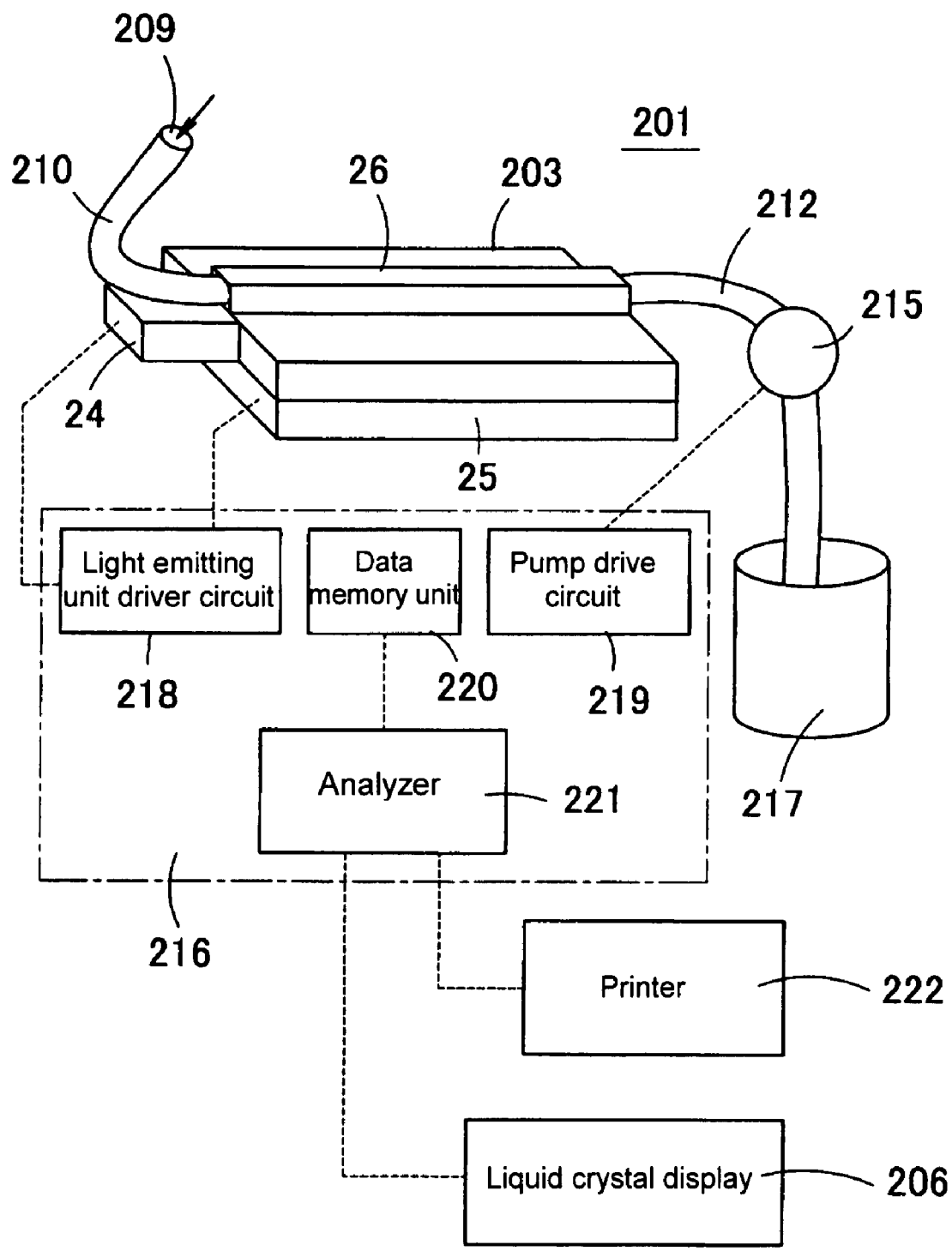
FIG. 62 shows a schematic view of the above flow-type analyzer shown in FIG. 60.

FIG. 62 shows a schematic view to explain the operation of the flow-type analyzer 201. The controller 216 includes a light emitting unit driver circuit 218, a pump drive circuit 219, a data memory unit 220, and an analyzer circuit 221. The light emitting unit driver circuit 218 controls the light emitting unit 24, the pump drive circuit 219 controls the pump 215, and the data memory unit 220 stores measured data from the light receiving element 25.

Thus, when the sample solution to be inspected is supplied from the sample solution supply port 209 and the pump 215 is driven, the sample solution supplied from the sample solution supply port 209 is suctioned by the pump 215 and flows at a constant flow rate, and the sample solution supplied from the supply tube 210 to the channel 33 branches off into each channel 33. At this time, when an antigen that is specifically coupled to the antibody fixed to the antibody holder 211 is contained in the sample solution, the antigen is coupled to the antibody. Then, the sample solution that has passed through the channel 33 is discharged from the sample solution discharge port 213 through the discharge tube 212 and discharged into the collecting tank 217 through the pump 215 in the sensor body 214. At this time, the controller 216 turns on the light emitting unit 24 by the light emitting unit drive circuit 218 to emit light to the light guide reflection plate 22 and reads the light intensity from the light receiving cell 25a in the light receiving element 25 and stores it in the data memory unit 220.

The analyzer circuit 221 determines whether there is an object to be measured such as a antigen or not and calculates the coupled amount of the object and a time variation of the coupled amount based on the measured data stored in the data memory unit 220 and outputs the result to the liquid crystal display 206. In addition, when the print switch 207 is pressed, the measured result is outputted from the printer 222 and a printed sheet comes out of the print result outlet 208. After the measurement, the replacement component 64 is removed from the sensor body 214 and abandoned.

Embodiment 17

Figure 63:
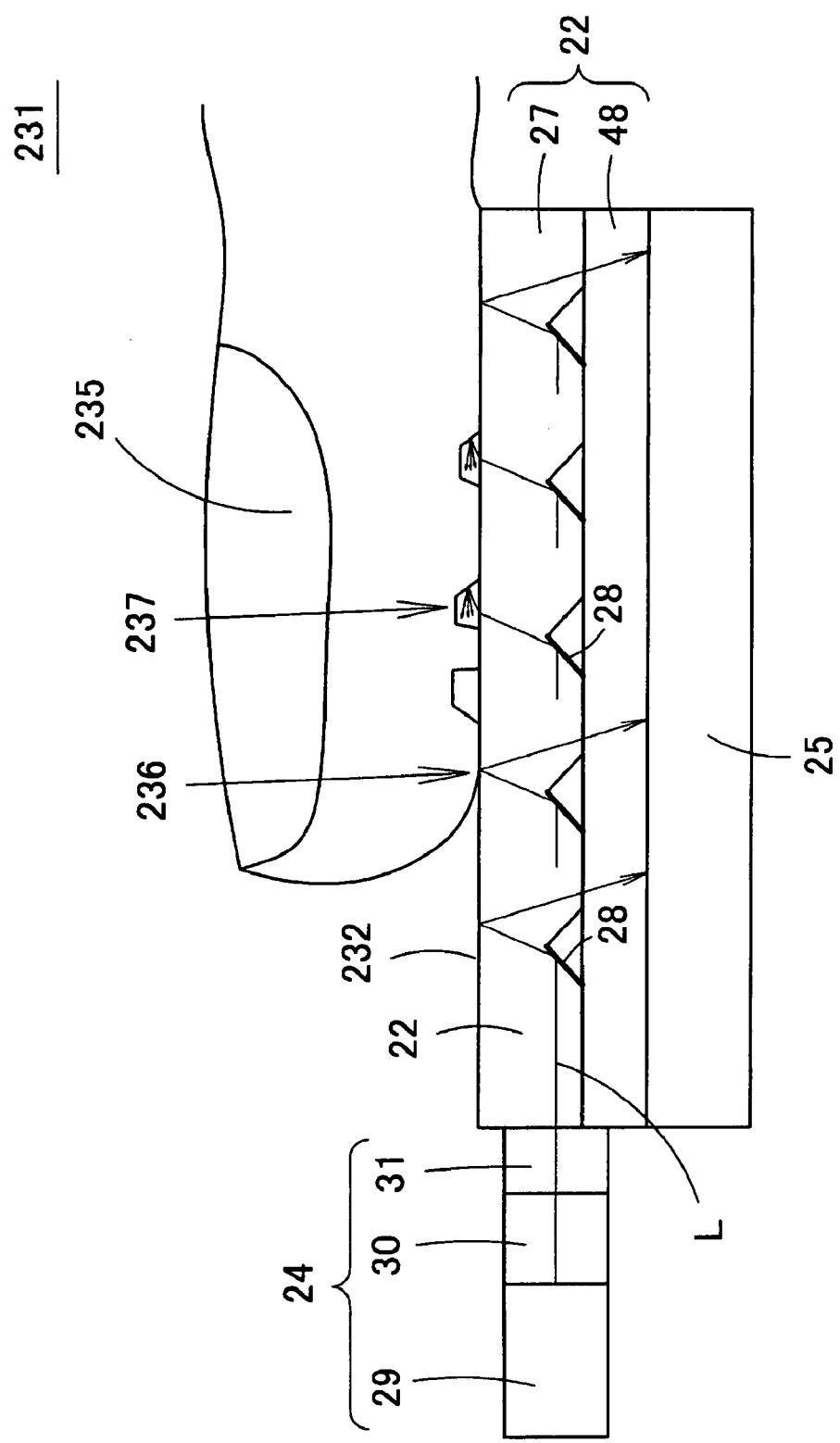
FIG. 63 shows a schematic view of a fingerprint recognition device according to an embodiment 17.

FIG. 63 shows a schematic view of a fingerprint recognition device 231 according to an embodiment of the present invention. The fingerprint recognition device 231 is provided such that a light guide reflection plate 22 is put on a light receiving element 25 including a two-dimensional light receiving element such as a CCD or a photodiode array, and the upper surface of the light guide reflection plate 22 is a fingerprint surface 232. Many fine reflection surfaces 28 are arranged in the light guide reflection plate 22 such that they form a checkered pattern when viewed from the direction perpendicular to the fingerprint surface 232, and an opening for passing light L is provided between the reflection surface 28 and the reflection surface 28. The inclined angle of the reflection surface 28 is equal. In addition, a light emitting unit 24 emits light collimated in the vertical direction only in a fan-like form in a horizontal plane (refer to FIG. 5 or 6) and arranged such that light emitting surface is at the same level as that of the reflection surface 28.

Figure 64B:
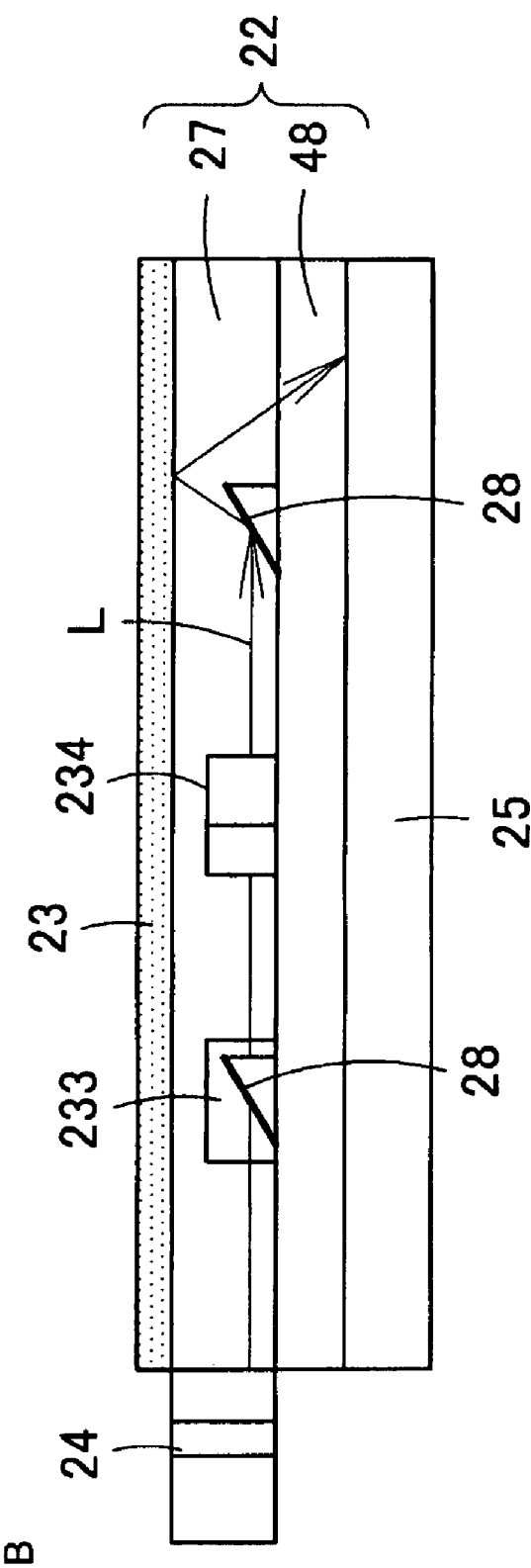

In addition, when the reflection surfaces 28 are relatively densely arranged like the surface plasmon sensor 231, the light L is interrupted by the reflection surface 28 positioned closer to the light emitting unit 24 and not likely to reach the rear reflection surface 28. Thus, according to the fingerprint recognition device 231, as shown in FIG. 64, light guiding reflection surfaces 233 and 234 are formed by forming cavities in a light guide plate 27. When the light L is reflected by the light guiding reflection surfaces 233 and 234, it diverts the reflection surface 28 positioned closer to the light emitting unit 24 so that the light L is inputted to the rear reflection surface 28 in the front direction.

Thus, when the fingerprint is recognized by the fingerprint recognition device 231, as shown in FIG. 63, a finger tip 235 is put on the fingerprint surface 232 of the fingerprint recognition device 231 and then the ball of the finger is pressed closely. When the light is emitted from the light emitting unit 24 in this state, the light reflected by the reflection surface 28 reaches the fingerprint surface 232. Here, when a convex 236 of the fingerprint is closely attached to the fingerprint surface 232 at the inputted point of the light, the light L is reflected here and received by the light receiving element 25. In addition, when a concave 237 of the fingerprint is closely attached to the fingerprint surface 232 at the inputted point of the light, the light inputted here reaches the concave 237 through the fingerprint surface 232 and scattered here and absorbed. Thus, the light L is hardly reflected by the light receiving element 25 at the position of the concave 237. Therefore, in the light receiving element 25, the light receiving amount varies depending on the contour pattern of the fingerprint and the fingerprint pattern is acquired in detail by the different pattern of the light receiving amount.

The light receiving amount pattern is sent to a determining device (not shown) and the determining device determines whether the fingerprint matches with a previously registered fingerprint or not.

According to the above fingerprint recognition device 231, the fingerprint can be illuminated by a few light sources 29, so that there can be provided the fingerprint recognition device 231 that is thin and has a few components.

In addition, as described in the embodiment 8, since the direction of the light reflected (reflected direction) by the reflection surface can be adjusted relatively freely by the configuration of the reflection surface, the light guiding reflection surface 234 of the light guiding reflection surfaces 233 and 234 shown in FIG. 64 can be omitted.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A surface plasmon sensor comprising:
    a light guide reflection plate comprising:
        a plurality of projections disposed on a first surface, and
        a plurality of first reflection surfaces disposed on the plurality of projections,
            wherein the plurality of projections are positioned in a non-overlapping manner on a horizontal plane of the first surface, and
            wherein each first reflection surface is inclined at a different angle to the first surface;
    a surface plasmon resonance layer, comprising a metal layer, formed on the first surface of the light guide reflection plate;
    a light emitting unit comprising a light source disposed on an end surface of the light guide reflection plate; and a light receiving element disposed on a second surface of the light guide reflection plate opposite the first surface, wherein the light guide reflection plate is configured to transmit light emitted by the light source, wherein the plurality of first reflection surfaces are configured to reflect the light to the surface plasmon resonance layer, wherein the metal layer is configured to reflect the light reflected by the plurality of first reflection surfaces, wherein the light guide reflection plate is configured to transmit the light reflected by the metal layer and emit the light out of the second surface to the light receiving element, and wherein the light receiving element is configured to receive the light reflected by the metal layer.

2. The surface plasmon sensor according to claim 1, wherein the light guide reflection plate further comprises at least one second reflection surface, paired with the at least one first reflection surface, the at least one first reflection surface is inclined toward the light source, the at least one second reflection surface is inclined away from the light source, and the at least one second reflection surface is configured to reflect the light reflected by the metal layer to the light receiving element.

3. The surface plasmon sensor according to claim 1, wherein the at least one first reflection surface is curved.

4. The surface plasmon sensor according to claim 1, wherein a spectral device is provided between the second surface of the light guide reflection plate and the light receiving element.

5. The surface plasmon sensor according to claim 1, further comprising a plurality of light emitting units, wherein the plurality of light emitting units comprise a plurality of light sources capable of emitting light sequentially, the light guide reflection plate comprises a plurality of first reflection surfaces, each of the plurality of first reflection surfaces are configured to reflect light emitted from a different light source of the plurality of light sources to the metal layer such that the light is reflected by the metal layer to a common inputted point in the light receiving element.

6. The surface plasmon sensor according to claim 1, wherein the light guide reflection plate comprises a plurality of first reflection surfaces, the light source is configured to emit light in a plane parallel to the surface plasmon resonance layer, and the plurality of first reflection surfaces are configured to reflect the light emitted by the light source to the metal layer such that the light is reflected by the metal layer to different points on the light receiving element, the different points being aligned in a straight line.

7. The surface plasmon sensor according to claim 1, wherein a deflection part is disposed between the metal layer and the light receiving element, in a light path of the light reflected by the metal layer, and the deflection part is configured to deflect the light path such that the incident angle of the light entering the light receiving element is decreased.

8. The surface plasmon sensor according to claim 1, wherein a light shielding plate for shielding light is disposed in the light guide reflection plate, and a hole for transmitting the light for measurement is provided in the light shielding plate.

9. The surface plasmon sensor according to claim 1, wherein a biomolecular recognition substance is fixed to the surface plasmon resonance layer.

10. A surface plasmon sensor comprising:

a light guide reflection plate comprising:

a plurality of projections disposed on a first surface, and a plurality of first reflection surfaces disposed on the plurality of projections, wherein the plurality of projections are positioned in a non-overlapping manner on a horizontal plane of the first surface, and wherein each first reflection surface is inclined at a different angle to the first surface;

a surface plasmon resonance layer, comprising a metal layer, formed on the first surface of the light guide reflection plate;

a light emitting unit comprising a light source disposed in a center of the light guide reflection plate; and a light receiving element disposed on a second surface of the light guide reflection plate opposite the first surface, wherein the light guide reflection plate is configured to transmit light emitted by the light source, wherein the plurality of first reflection surfaces are configured to reflect the light to the surface plasmon resonance layer, wherein the metal layer is configured to reflect the light reflected by the plurality of first reflection surfaces, wherein the light guide reflection plate is configured to transmit the light reflected by the metal layer and emit the light out of the second surface to the light receiving element, and wherein the light receiving element is configured to receive the light reflected by the metal layer.

11. The surface plasmon sensor according to claim 10, wherein the light guide reflection plate further comprises at least one second reflection surface, paired with the at least one first reflection surface, the at least one first reflection surface is inclined toward the light source, the at least one second reflection surface is inclined away from the light source, and the at least one second reflection surface is configured to reflect the light reflected by the metal layer to the light receiving element.

12. The surface plasmon sensor according to claim 10, wherein the light guide reflection plate is configured to rotate around a rotation axis which passes through the light source and is perpendicular to the surface plasmon resonance layer.

13. The surface plasmon sensor according to claim 10, wherein the light guide reflection plate is configured to rotate around a rotation axis perpendicular to the surface plasmon resonance layer, the light receiving element is arranged along the second surface in a radial direction, and the light source is disposed at the center of the light guide reflection plate and is inclined towards light receiving element.

14. A flow-type analyzer comprising:

a surface plasmon sensor;

a flow path; and a sample supply path and a pump for flowing an inspection sample solution to the flow path, the surface plasmon sensor comprising:

a light guide reflection plate comprising;

a plurality of projections disposed on a first surface, and a plurality of first reflection surfaces disposed on the plurality of projections, wherein the plurality of projections are positioned in a non-overlapping manner on a horizontal plane of the first surface, and wherein each first reflection surface is inclined at a different angle to the first surface;

a surface plasmon resonance layer, comprising a metal layer, formed on the first surface of the light guide reflection plate;

a light emitting unit comprising a light source disposed on an end surface of the light guide reflection plate; and a light receiving element disposed on a second surface of the light guide reflection plate opposite the first surface, wherein the light guide reflection plate is configured to transmit light emitted by the light source, wherein the plurality of first reflection surfaces are configured to reflect the light to the surface plasmon resonance layer, wherein the metal layer is configured to reflect the light reflected by the plurality of first reflection surfaces, wherein the light guide reflection plate is configured to transmit the light reflected by the metal layer and emit the light out of the second surface to the light receiving element, and wherein the light receiving element is configured to receive the light reflected by the metal layer, wherein the flow path is formed on a surface of the surface plasmon layer opposite to the light guide reflection plate.

15. The flow-type analyzer according to claim 14, wherein the plurality of first reflection surfaces are configured to reflect the light to points on the metal layer that form a line corresponding to the flow path on the metal layer.

16. The flow-type analyzer according to claim 14, wherein the surface plasmon resonance layer is formed by depositing a metal film on a transparent auxiliary substrate, and the surface plasmon resonance layer and the flow path are detachably mounted on the first surface of the light guide reflection plate.

* * * * *